US011697822B2

(12) United States Patent
Darvey et al.

(10) Patent No.: US 11,697,822 B2
(45) Date of Patent: Jul. 11, 2023

(54) BLUE ALEURONE AND OTHER SEGREGATION SYSTEMS

(71) Applicants: KWS SAAT SE & Co. KGaA, Einbeck (DE); THE UNIVERSITY OF SYDNEY, Sydney (AU); GLOBAL CROP INNOVATIONS PTY. LTD., Cawdor (AU)

(72) Inventors: Norman Darvey; Peng Zhang, Sydney (AU); Richard Trethowan, Sydney (AU); Chong Mei Dong, Sydney (AU); Jacob Lage, Comberton (GB); Nicholas Bird, Mulbarton (GB); Christopher Tapsell, Oakham (GB); Aaron Hummel, St. Louis, MO (US)

(73) Assignees: KWS SAAT SE & Co. KGaA, Einbeck (DE); THE UNIVERSIYY OF SYDNEY, Sydney (AU); GLOBAL CROP INNOVATIONS PTY. LTD., Cawdor (AU)

( * ) Notice: Subject to any disclaimer, the term of this patent is extended or adjusted under 35 U.S.C. 154(b) by 374 days.

(21) Appl. No.: 16/643,277

(22) PCT Filed: Aug. 29, 2018

(86) PCT No.: PCT/EP2018/073282
§ 371 (c)(1),
(2) Date: Feb. 28, 2020

(87) PCT Pub. No.: WO2019/043082
PCT Pub. Date: Mar. 7, 2019

(65) Prior Publication Data
US 2020/0255856 A1    Aug. 13, 2020

Related U.S. Application Data

(60) Provisional application No. 62/610,727, filed on Dec. 27, 2017, provisional application No. 62/551,599, filed on Aug. 29, 2017.

(51) Int. Cl.
*C12N 15/82* (2006.01)

(52) U.S. Cl.
CPC ................. *C12N 15/8289* (2013.01)

(58) Field of Classification Search
CPC ................. A01H 1/06; A01H 6/4678
See application file for complete search history.

(56) References Cited

U.S. PATENT DOCUMENTS

| 4,918,006 | A | 4/1990 | Ellar et al. |
|---|---|---|---|
| 4,945,050 | A | 7/1990 | Sanford et al. |
| 5,240,855 | A | 8/1993 | Tomes |
| 5,268,463 | A | 12/1993 | Jefferson |
| 5,316,931 | A | 5/1994 | Donson et al. |
| 5,322,783 | A | 6/1994 | Tomes et al. |
| 5,324,646 | A | 6/1994 | Buising et al. |
| 5,478,369 | A | 12/1995 | Albertsen et al. |
| 5,563,055 | A | 10/1996 | Townsend et al. |
| 5,589,367 | A | 12/1996 | Donson et al. |
| 5,599,670 | A | 2/1997 | Jefferson |
| 5,736,369 | A | 4/1998 | Bowen et al. |
| 5,866,785 | A | 2/1999 | Donson et al. |
| 5,879,918 | A | 3/1999 | Tomes et al. |
| 5,886,244 | A | 3/1999 | Tomes et al. |
| 5,889,190 | A | 3/1999 | Donson et al. |
| 5,889,191 | A | 3/1999 | Turpen |
| 5,932,782 | A | 8/1999 | Bidney |
| 5,981,840 | A | 11/1999 | Zhao et al. |
| 6,265,640 | B1 | 7/2001 | Albertsen et al. |
| 6,300,543 | B1 | 10/2001 | Cass et al. |
| 7,098,388 | B2 | 8/2006 | Albertsen et al. |
| 7,517,975 | B2 | 4/2009 | Albertsen et al. |
| 7,612,251 | B2 | 11/2009 | Albertsen et al. |
| 7,919,676 | B2 | 4/2011 | Albertson et al. |
| 2002/0081614 | A1 | 6/2002 | Case et al. |
| 2003/0021776 | A1 | 1/2003 | Rebar et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0188987 | A1 | 8/2006 | Guschin |
| 2006/0246567 | A1 | 11/2006 | Rebar et al. |
| 2008/0182332 | A1 | 7/2008 | Cai et al. |
| 2010/0291048 | A1 | 11/2010 | Holmes et al. |

(Continued)

FOREIGN PATENT DOCUMENTS

| CN | 106520785 A | 3/2017 |
|---|---|---|
| EP | 0329308 A2 | 8/1989 |

(Continued)

OTHER PUBLICATIONS

T. R. Endo, "The gametocidal chromosome as a tool for chromosome manipulation in wheat", Chromosome Research, vol. 15, No. 1, Jan. 2007, pp. 67-75.
Pioneer Hi-Bred International, Inc.: "Seed Production Technology (SPT), Process DP-32138-1", May 2001.
International Search Report and Written Opinion dated Oct. 25, 2019, issued in corresponding Application No. PCT/EP2018/073282.
Aufsaftz et al., "RNA-directed DNA methylation in *Arabidopsis*", Proc. Nat'l. Acad. Sci., 2002, vol. 99, Suppl. 4, pp. 16499-16506.
Baim et al., "A chimeric mammalian transactivator based on the lac repressor that in regulated by temperature and Isopropyl β-D-thlogalactopyranoside", Proc. Natl., Acad. Sci., 1991, vol. 88, pp. 5072-5076.

(Continued)

*Primary Examiner* — Russell Kallis
(74) *Attorney, Agent, or Firm* — Troutman Pepper Hamilton Sanders LLP

(57) ABSTRACT

The present invention relates to materials and methods for creating and maintaining a cereal plant line for the production of a hybrid cereal plant, that include for example, and not limitation, using the BLue Aleurone (BLA) system.

20 Claims, 18 Drawing Sheets

Specification includes a Sequence Listing.

(56) References Cited

U.S. PATENT DOCUMENTS

| | | | |
|---|---|---|---|
| 2011/0145940 A1 | 6/2011 | Voytas et al. |
| 2011/0239315 A1 | 9/2011 | Bonas et al. |
| 2011/0269234 A1 | 11/2011 | Doyon |
| 2013/0123484 A1 | 5/2013 | Liu et al. |
| 2015/0152398 A1 | 6/2015 | Doudna et al. |
| 2016/0145631 A1 | 5/2016 | Voytas et al. |
| 2016/0201084 A1 | 7/2016 | Albertsen et al. |

FOREIGN PATENT DOCUMENTS

| | | | |
|---|---|---|---|
| EP | 0737749 A1 | 10/1996 | |
| WO | 90/08828 | 8/1990 | |
| WO | 90/08829 A1 | 8/1990 | |
| WO | 1992/001366 A1 | 2/1992 | |
| WO | WO 93/13649 | * 1/1993 | ............ A01H 1/02 |
| WO | 93/13649 A1 | 7/1993 | |
| WO | 1998/051142 A1 | 11/1998 | |
| WO | 02/057308 A2 | 7/2002 | |
| WO | 2002/052924 A2 | 7/2002 | |
| WO | 2002/059269 A2 | 8/2002 | |
| WO | WO 02/059269 | * 11/2002 | |
| WO | 2003/057848 A2 | 7/2003 | |
| WO | 03/078619 A1 | 9/2003 | |
| WO | 2004/031346 | 4/2004 | |
| WO | 2005/105989 | 11/2005 | |
| WO | 2006/097784 | 9/2006 | |
| WO | 2006/097853 | 9/2006 | |
| WO | 2006/097854 | 9/2006 | |
| WO | 2010/079430 A1 | 7/2010 | |
| WO | 2011/017293 A2 | 2/2011 | |
| WO | 2016/021973 A1 | 2/2016 | |
| WO | 2016/048891 A1 | 3/2016 | |
| WO | 2016/196655 | 12/2016 | |
| WO | 2016/205749 | 12/2016 | |

OTHER PUBLICATIONS

Bevan, "Binary Agrobacterium vectors for plant transformation", Nucleic Acids Research, 1984, vol. 12, No. 22, pp. 8711-8721.
Boulton et al., "Specificity of Agrobacterium mediated delivery of maize streak virus DNA to members of the Gramineae", Plant Molecular Biology, 1989, vol. 12, pp. 31-40.
Burstein et al., "New CRISPR-Cas systems from uncultivated microbes", Nature, 2017, vol. 542, pp. 237-241.
Bytebier et al., "T-DNA organization in tumor cultures and transgenic plants of the monocotyledon Asparagus officinalis", Proc. Natl. Acad. Sci, 1987, vol. 84, pp. 5345-5349.
Cenci et al., Construction and characterization of a half million clone BAC library of durum wheat (*Triticum turgidum* ssp. durum), Theor. Appl. Genet, 2003, vol. 107, No. 5, pp. 931-939.
Chames et al., "In vivo selection of engineered homing endonucleases using double-strand break induced homologous recombination", Nucleic Acids Research, 2005, vol. 33, No. 20, e178, 10 pages.
Chen et al., "A highly sensitive selection method for directed evolution of homing endonucleases", Nucleic Acids Research, 2005, vol. 33, No. 18, e154, 7 pages.
Chevalier et al., "Design, Activity, and Structure of a Highly Specific Artificial Endonuclease", Molecular Cell, 2002, vol. 10, pp. 895-905.
Christian et al., "Targeting DNA Double-Strand Breaks with TAL Effector Nucleases", Genetics, 2010, vol. 186, pp. 757-761.
Christopherson et al., "Ecdysteroid-dependent regulation of genes in mammalian ceils by *Drosophila ecdysone* receptor and chimeric transactivators", Proc. Natl. Acad. Sci., vol. 89, 1992, pp. 6314-6318.
Christou et al., "Parameters Influencing Stable Transformation of Rice Immature Embryos and Recovery of Transgenic Plants using Electric Discharge Particle Acceleration", Annals of Botany, 1995, vol. 75, No. 4, pp. 407-413.
Christou et al., "Stable Transformation of Soybean Callus by DNA-Coated Gold Particles", Plant Physiol., 1988, vol. 87, pp. 671-674.

Crossway et al., "Integration of foreign DNA following microinjection of tobacco mesophyil protoplasts", Mol. Gen. Genet., 1986, vol. 202, pp. 179-185.
Degenkolb et al., "Structural Requirements of Tetracycline-Tet Repressor Interaction: Determination of Equilibrium Binding Constants for Tetracycline Analogs with the Tet Repressor", Antimicrobial Agents and Chemotherapy, 1991, vol. 35, No. 8, pp. 1591-1595.
Deuschle e al., "Regulated expression of foreign genes in mammalian ceils under the control of coliphage T3 RNA polymerase and lac repressor", Proc. Natl. Acad. Sci., 1989, vol. 86, pp. 5400-5404.
Deuschle et al., "RNA Polymerase II Transcription Blocked by *Escherichia coli* Lac Repressor", Science, 1990, vol. 248, No. 4954, pp. 480-483.
D'Halluin et al., "Transgenic Maize Plants by Tissue Electroporation", The Plant Cell, 1992, vol. 4, pp. 1495-1505.
Endo, "Two types of gametocidai chromosome of Aegilops sharonensis and Ae. Longissima", Jpn. J. Genet., 1985, vol. 60, pp. 125-135.
Epinat et al., "A novel engineered meganuclease induces homologous recombination in yeast and mammalian cells", Nucleic Acids Research, 2003, vol. 31, No. 11, pp. 2952-2962.
Fraley et al., "Expression of bacterial genes in plant cells", Proc. Nat'l. Acad. Sci., 1983, vol. 80, pp. 4803-4807.
Fuerst et al., "Transfer of the inducible lac repressor / operator systems from *Escherichia coli* to a vaccinia virus expression vector", Proc. Natl. Acad. Sci. USA, 1989, vol. 86, pp. 2549-2553.
Gallie, "Introduction of mRNA to plant protoplasts using polyethylene glycol", Plant Cell Reports, 1993, vol. 13, pp. 119-122.
Gossen et al., "Tight control of gene expression in mammalian cells by tetracycline-responsive promoters", Proc. Natl. Acad. Sci. USA, 1992, vol. 89, pp. 5547-5551.
Gould et al., "Transformation of *Zea mays* L. Using Agrobacterium tumefaciens and the Shoot Apex", Plant Physiol., 1991, vol. 95, pp. 426-434.
Hepler et al., "Nuclear concentration and mitotic dispersion of the essential cell cycle protein, p13suc1, examined in living cells", Proc. Natl. Acad. Sci. USA, 1994, vol. 91, pp. 2176-2180.
Hernalsteens et al., "An Agrobacterium-transformed cell culture from the monocot Asparagus officinalis", The EMBO Journal, 1984, vol. 3, No. 13, pp. 3039-3041.
Horsch et al., "Inheritance of Functional Foreign Genes in Plants", 1984, Science, vol. 233, pp. 496-498.
Horsch et al., "A Simple and General Method for Transferring Genes into Plants", Science, 1985, vol. 227, No. 4691, pp. 1229-1231.
Hush et al., "Quantification of microtubule dynamics in living plant cells using fluorescence redistribution after photobleaching", Journal of Cell Science, 1994, vol. 107, pp. 775-784.
Jinek et al., "A Programmable Dual-RNA-Guided DNA Endonuclease in Adaptive Bacterial Immunity", Science, 2012, vol. 337, No. 6096, pp. 816-821.
Jurica et al., "Homing endonucleases: structure, function and evolution", Cell. Mol. Life Sci., 1999, vol. 55, pp. 1304-1326.
Kaeppler et al., "Silicon carbide fiber-mediated DNA delivery into plant cells", Plant Cell Reports, 1990, vol. 9, pp. 415-418.
Kaeppler et al., "Silicon carbide fiber-mediated transformation of plant cells", Theor Appl Genet, 1992, vol. 84, pp. 560-566.
Keen et al., "Structure of Two Pectate Lyase Genes from Erwinia chrysanthemi EC16 and Their High-Level Expression in *Escherichia coli*", Journal of Bacteriology, 1986, vol. 168, No. 2, pp. 595-606.
Klein et al., "Genetic Transformation of Maize Cells by Particle Bombardment", Plant Physiol., 1989, vol. 91, pp. 440-444.
Klein et al., "Transfer of foreign genes into intact maize cells with high-velocity microprojectiles", Proc. Natl. Acad. Sci. USA, 1988, vol. 85, pp. 4305-4309.
Fossati et al., "A male sterile mutant in Triticum aestivum", Wheat Information Service, 1970, vol. 30, pp. 8-10.
Klindworth et al., "Chromosomal Location of Genetic Male Sterility Genes in Four Mutants of Hexaplold Wheat", Crop Sci., 2002, vol. 42, pp. 1447-1450.
Kynast et al., "Fate of multicentric and ring chromosomes induced by a new gametocidal factor located on chromosome 4Mg of Aegilops geniculata", Chromosome Research, 2000, vol. 8, pp. 133-139.

(56) References Cited

OTHER PUBLICATIONS

Labow et al., "Conversion of the lac Repressor into an Allosterically Regulated Transcriptional Activator for Mammalian Cells", Molecular and Cellular Biology, 1990, vol. 10, No. 7, pp. 3343-3356.
Li et al., "TAL nucleases (TALNs): hybrid proteins composed of TAL effectors and FokI DNA-cleavage domain", Nucleic Acids Research, 2010, vol. 39, No. 1, pp. 359-372.
Li et al., "An improved rice transformation system using the biolistic method", Plant Cell Reports, 1993, vol. 12, pp. 250-255.
Lucas et al., "Rapid evolution of the DNA-binding site in LAGLIDADG homing endonucleases", Nucleic Acids Research, 2001, vol. 29, No. 4, pp. 960-969.
Makarova et al., "An updated evolutionary classification of CRISPR-Cas systems", Nature Rev. Microbiol., 2015, vol. 13, No. 11, pp. 722-736.
McLean et al., "Expression in *Escherichia coli* of a Cloned Crystal Protein Gene of *Bacillus thuringiensis* subsp. Israelensis", Journal of Bacteriology, 1987, vol. 169, No. 3, pp. 1017-1023.
Morbitzer et al., "Regulation of selected genome loci using de novo-engineered transcription activator-like effector (TALE)-type transcription factors", PNAS, 2010, vol. 107, No. 50, pp. 21617-21622.
Gruen et al., "An in vivo selection system for homing endonuclease activity", Nucleic Acids Research, 2002, vol. 30, No. 7, e29, 6 pages.
Oliva et al., "Evidence that Tetracycline Analogs Whose Primary Target is Not the Bacterial Ribosome Cause Lysis of *Escherichia coli*", Antimicrobal Agents and Chemotherapy, 1992, vol. 35, No. 5 pp. 913-919.
Ishida et al., "High efficiency transformation of maize (*Zea mays* L.) mediated by Agrobacterium tumefaciens", Nature Biotechnology, 1996, vol. 14, pp. 745-750.
Paszkowski et al., "Direct gene transfer to plants", The EMBO Journal, 1984, vol. 3, No. 12, pp. 2717-2722.
Reines et al., "Elongation factor SII-dependent transcription by RNA polymerase II through a sequence-specific DNA-binding protein", Proc. Natl. Acad. Sci. USA, 1993, vol. 90, pp. 1917-1921.
Reznikoff, "The lactose operon-controlling elements: a complex paradigm", Molecular Microbiology, 1992, vol. 6, No. 17, pp. 2419-2422.
Riggs et al., "Stable transformation of tobacco by electroporation: Evidence for plasmid concatenation", Proc. Natl. Acad. Sci. USA, 1986, vol. 83, pp. 5602-5606.
Roberts et al., "A nomenclature for restriction enzymes, DNA methyltransferases, homing endonucleases and their genes", Nucleic Acids Research, 2003, vol. 31, No. 7, pp. 1805-1812.
Roberts et al., "REBASE: restriction enzymes and methyltransferases", Nucleic Acids Research, 2003, vol. 31, No. 1, pp. 418-420.
Rosen et al., "Homing endonucleases I-CreI derivatives with novel DNA target specificities", Nucleic Acids Research, 2006, vol. 34, No. 17, pp. 4791-4800.
Rubnitz et al., "The Minimum Amount of Homology Required for Homologous Recombination in Mammalian Cells", Molecular and Cellular Biology, 1984, vol. 4, No. 11, pp. 2253-2258.
Scheid et al., "Two regulatory levels of transcriptional gene silencing in *Arabidopsis*", PNAS, 2002, vol. 99, No. 21, pp. 13659-13662.
Scholze et al., "TAL effector-DNA specificity", Virulence, 2010, vol. 1, issue 5, pp. 428-432.
Sears, "An Induced mutant with homoeologous pairing in common wheat", Canadian Journal of Genetics and Cytology, 1977, vol. 19, No. 4, pp. 585-593.
Endo et al., "Physical mapping of a male-fertility gene of common wheat", The Japanese Journal of Genetics, 1991, vol. 66, No. 3, pp. 291-295.
Seligman et al., "Mutations altering the cleavage specificity of a homing endonuclease", Nucleic Acids Research, 2002, vol. 30, No. 17, pp. 3870-3879.
Sijen et al., "Transcriptional and posttranscriptional gene silencing are mechanistically related", Current Biology, 2001, vol. 11, No. 6, pp. 436-440.
Singh et al., "Cytological characterization of transgenic soybean", Theor Appl Genet, 1998, vol. 96, pp. 319-324.
Smith et al., "A combinatorial approach to create artificial homing endonucleases cleaving chosen sequences", Nucleic Acids Research, 2006, vol. 34, No. 22, e149, 12 pages.
Tucker et al., "Molecular Identification of the wheat male fertility gene Ms1 and its prospects for hybrid breeding", Nature Communications, 2017, vol. 8, Article No. 869, 10 pages.
Waninge et al., "Chromosome Numbers in Pugley's Male Sterile Wheat", Euphytica, 1968, vol. 17, pp. 378-380.
Waterhouse et al., "Exploring Plant Genomes by RNA-Induced Gene Silencing", Nature Reviews Genetics, 2003, vol. 4, pp. 29-38.
Weising et al., "Foreign Genes in Plants: Transfer, Structure, Expression, and Applications", Annu. Rev. Genet., 1988, vol. 22, pp. 421-477.
Wyborskl et al., "Analysis of Inducers of the *E. coil* lac repressor system in mammalian cells and whole animals", Nucleic Acids Research, 1991, vol. 19, No. 17, pp. 4647-4653.
Yarranton, "Inducible vectors for expression in mammalian cells", Current Opinion Biotechnology, 1992, vol. 3, pp. 506-511.
Zambetti et al., "A mutant p53 protein is required for maintenance of the transformed phenotype in cells transformed with p53 plus ras cDNAs", Proc. Natl. Acad. Sci. USA, 1992, vol. 89, pp. 3952-3956.
Li et al., "ThMYC4E, candidate Blue aleurone 1 gene controlling the associated trait in *Triticum aestivum*", PLOS One, 2017, vol. 12, No. 7, p. e0181116; 13 pages.

\* cited by examiner

Figure 1
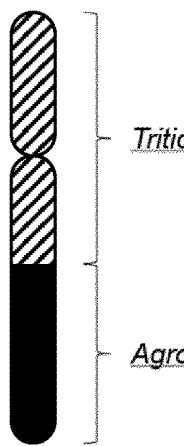
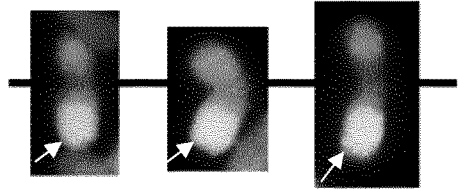
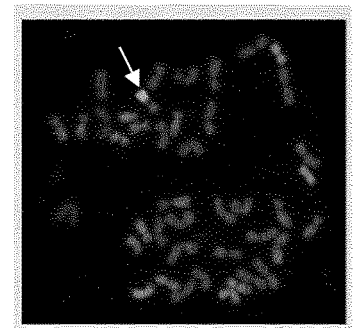
4AgL(blue)/4BoL/4BoS(restorer)
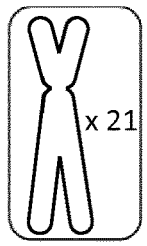
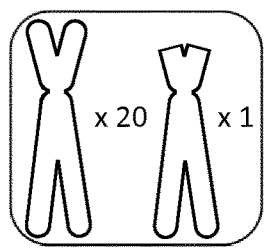
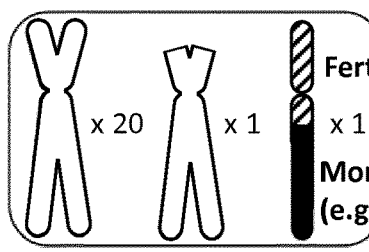
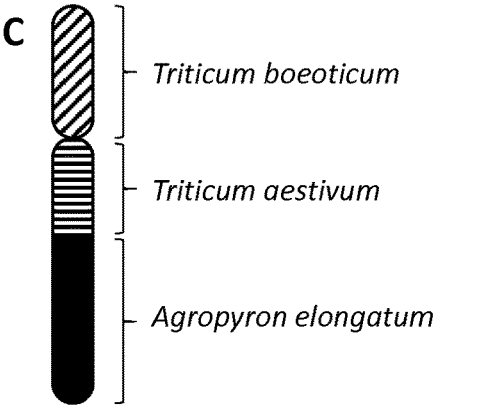
T4BoS(restorer).4BL-4AgL(blue)

Figure 4
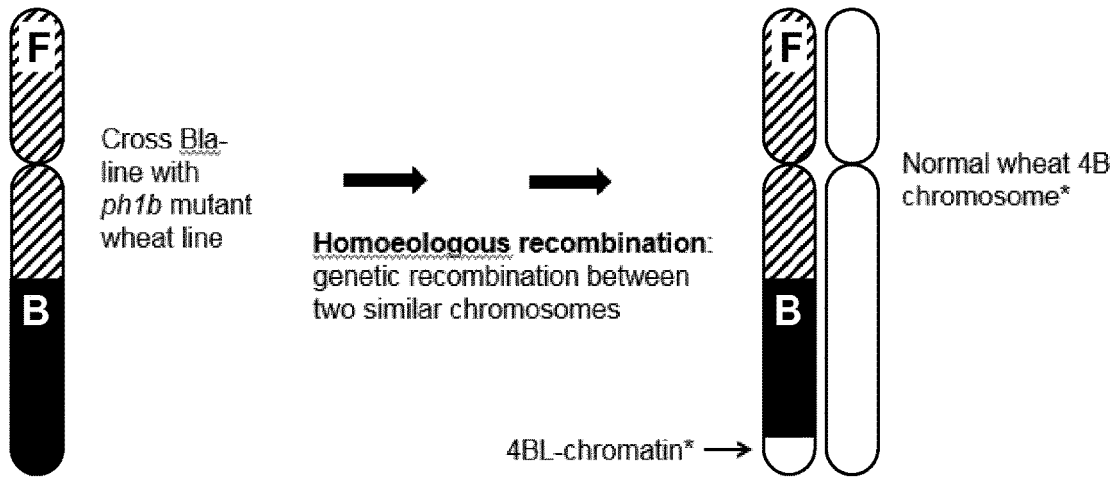
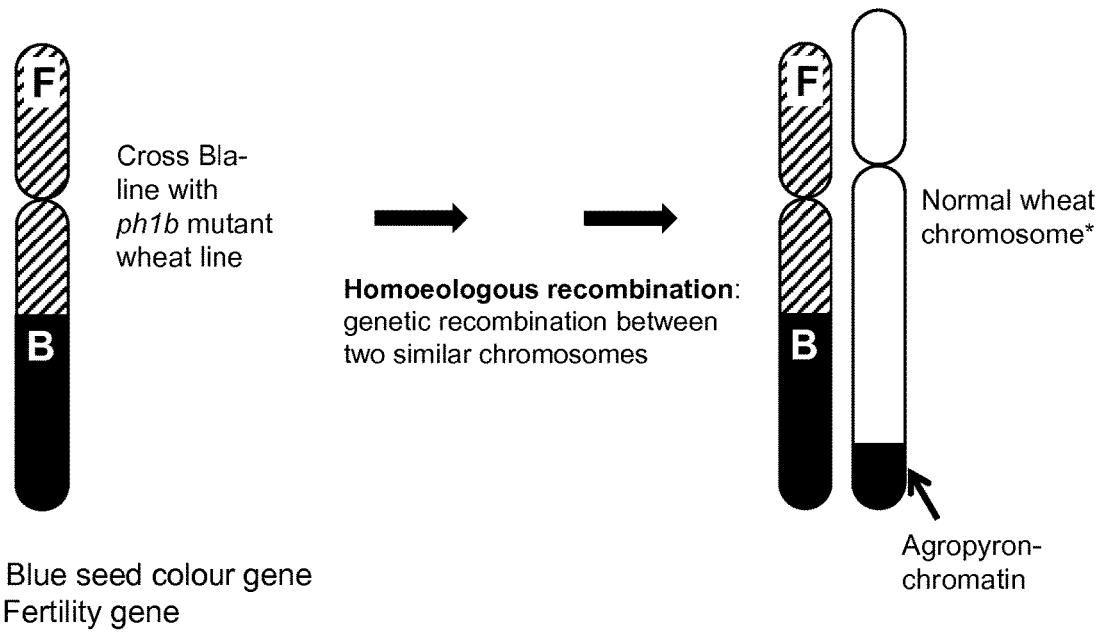

Figure 5

| Cross 1 | Bla-line | x | Disomic addition 2C$^c$ |
|---|---|---|---|
| | 21"+B' (*msms*) | | 21" +2C$^{c"}$ (*MsMs*) |

| | | action | phenotype | chromosome # |
|---|---|---|---|---|
| F1 possibilities: | 21" +2C$^{c'}$ (*Msms*) | Discard | White fertile | 43 |
| | 21" +B' +2C$^{c'}$ (*Msms*) | Keep | Blue fertile | 44 |

| Cross 2 | F1 from Cross 1 | x | Bla-line |
|---|---|---|---|
| | 21" +B' +2C$^{c'}$ (*Msms*) | | 21" +B' (*msms*) |

| | | action | phenotype | chromosome # |
|---|---|---|---|---|
| F1 possibilities: | 21" (*Msms*) | Discard | White fertile | 42 |
| | 21" (*msms*) | Discard | White sterile | 42 |
| | 21"+B' (*Msms*) | Discard | Blue fertile | 43 |
| | 21" +B' (*msms*) | Keep | Blue fertile | 43 |
| | 21" +2C$^{c'}$ (*Msms*) | Discard | White fertile | 43 |
| | 21" +2C$^{c'}$ (*msms*) | Discard | White sterile | 43 |
| | 21" +B' +2C$^{c'}$ (*Msms*) | Discard | Blue fertile | 44 |
| | 21" +B' +2C$^{c'}$ (*msms*) | Discard | Blue fertile | 44 |

Self    **21" +B' (*msms*)**

| F2 possibilities | 21" (*msms*) | Discard | White sterile | 42 |
|---|---|---|---|---|
| | 21" +B' (*msms*) | Keep | Blue fertile | 43 |

Self    **21" +B' (*msms*)**

| F3 possibilites | 21" (*msms*) | Discard F2:3 populations with >0 fertile plants | | |
|---|---|---|---|---|
| | 21" +B' (*msms*) | | | |

Figure 6

Starting material  21"+ B' (*msms*)
    *Irradiate (175, 200, 225 and 250 Gy) to produce M0 seeds*
    planting M0 seeds and self fertilizing Harvesting all M1 seeds (M1 seed population) from individual M0 plants

M1 seed population
  white seeds grow into 100% sterile plants when self fertilizing → Keep Population
  white seeds grow into <100% sterile plants when self fertilizing → Discard Population Growing plants from the blue seeds of kept M1 seed population and self fertilizing for generating the M2 seed population

M2 seed population
  if white seeds grow into 100% sterile plants when self fertilizing → Keep Population
  if white seeds grow into <100% sterile plants when self fertilizing → Discard Population Cytological determination of a rearrangement in the monosomic chromosome of at least one blue seed

Figure 7

| Cross | Double blue Bla-line 21"+B" (Ph1Ph1) | x | | ph1b-mutant line 21"(ph1bph1b) | |
|---|---|---|---|---|---|
| | | | action | phenotype | chromosome # |
| F1 | 21"+B' (Ph1ph1b) | | Keep | Blue | 43 |
| Self-fertilizing plants grown from F1 seeds | 21"+B' (Ph1bph1b) | | | | |

Select blue seed and ph1bph1b

Self-fertilizing plants grown from said blue seeds and calculate segregation ratio of harvested seeds

| | F2 possibilities | 21" +B' (ph1bph1b) | Discard | 1 blue : 3 white | 43 |
|---|---|---|---|---|---|
| | | 21" (ph1bph1b) | Keep | ~1-3 blue : 1 white | 42 |

Figure 9

| Line | Oligo FISH Results | Chromosome Composition |
|---|---|---|
| Double blue Bla-lines used as control for the original alien chromosome (BoAg) | | |
| DB AR13 | 42; 1 pair of T1RS.1BL; 1 pair of 4D was substituted by 1 pair of BoAg | 20"+BoAg(4D)" |
| DB AR5 | 44; 1 pair of BoAg | 21"+BoAg" |
| Parental lines involved | | |
| White AR6 | 42 | 21" |
| White AR23-6 | 42 | 21" |
| White R33-1-1 | 42; 1 pair of T1RS.1BL | 21" |
| Angas *ph1b* | 42 | |
| | 42; 1 normal 4D, 1 modified 4D | |
| Pavon *ph1b* | 42; 1 copy of 4B; 1 normal 4D, 1 modified 4D; l pair of normal 3D; 1 T3DS.3DL-6AL?; 1 normal 6A, 1 T6AS.6AL-3DL | |
| Selfed seed | | |
| 149-3-1 | 42; 1 pair of T1RS.1BL; 1 copy of 1A; 1 copy of BoAg | 20"+1A'+BoAg' |
| 149-3-2 | 44; 1 pair of T1RS.1BL; 1 copy of 1A; 3 copies of 5B; 1 pair of BoAg | 19"+1A'+5B'''+BoAg" |
| 149-3-3 | 44; 1 pair of T1RS.1BL; 1 copy of 1A; l pair of normal 7A, 1 copy of mod. 7A; 1 pair of BoAg | 19"+1A'+7A"+7A (mod)'+BoAg" |
| 149-3-4 | 41; 1 pair of T1RS.1BL; 1 copy of 1A; 1 copy of 4B; 1 copy of BoAg | 19"+1A'+4B'+BoAg' |
| 149-4-3 | 42; 1 pair of T1RS.1BL; 1 copy of T4BS.4BL-BoAgL; 1 copy of BoAg | 20"+T4BS.4BL-4AgL'+BoAg' |
| 149-4-6 | 43; 1 pair of T1RS.1BL; 1 copy of 4B; 1 pair of BoAg | 20"+4B'+BoAg" |
| 149-4-7 | 44; 1 pair of T1RS.1BL; 1 copy of 4B; 3 copie of 3D; 1 copy of normal BoAg, 1 copy of mod. BoAg | 19"+4B'+3D'''+BoAg'+T4DS?-4BoS.4BoL-4AgL' |
| 149-4-8 | 43; 1 pair of T1RS.1BL; 1 copy of BoAg | 21"+BoAg' |
| 168-4-1 | 44; 1 pair of T1RS.1BL; 3 copies of 4D; 1 copy of BoAg | 20"+4D'''+BoAg' |
| 168-4-2 | 43; 1 pair of T1RS.1BL; 1 copy of BoAg | 21"+BoAg' |
| 168-4-3 | 43; 1 pair of T1RS.1BL; 1 copy of BoAg | 21"+BoAg' |
| 168-4-5 | 43; 1 pair of T1RS.1BL; 1 copy of BoAg | 21"+BoAg' |
| P5-4-2-1 | 42; 1 pair of T1RS.1BL; 1 pair of 4D was substituted by 1 pair of BoAg | 20"+BoAg(4D)" |
| P5-4-2-2 | 42; 1 pair of T1RS.1BL; 1 pair of 4D was substituted by 1 pair of BoAg; 1 norml 4B, 1 mod. 4B | 19"+BoAg(4D)"+4B'+T4BS.4BL-?' |
| P5-4-2-3 | 42; 1 pair of T1RS.1BL; 1 copy of 4D; 1 copy of BoAg; 1 norml 4B, 1 mod. 4B; 1 norml 5B, 1 mod. 5B | 18"+4D'+BoAg'+4B'+T4BS.4BL-?'+5B'+T5BS.5BL-?' |
| P5-4-2-4 | 42; 1 pair of T1RS.1BL; 1 copy of 4D; 1 copy of BoAg | 20"+4D'+BoAg' |
| Crossed seed | | |
| A-1 | 42; 1 copy of T1RS.1BL, 1 copy of 1B; 1 copy of 4D; 1 copy of BoAg | 20"+4D'+BoAg' |
| A-2 | 43; 1 copy of T1RS.1BL, 1 copy of 1B; 1 pair of normal 6A, 1 mod. 6A; 1 copy of 1D; 3 copies of 2D; 1 copy of 4D, 1 copy of mod. 4D; 1 copy of 6D; 1 copy of BoAg | 17"+6A?'+1D'+2D'''+4D'+4D (mod)'+6D'+BoAg' |
| A-3 | 42; 1 copy of T1RS.1BL, 1 copy of 1B; 1 copy of 4D; 1 copy of BoAg | 20"+4D'+BoAg' |
| A-4 | 42; 1 copy of T1RS.1BL, 1 copy of 1B; 1 copy of 4D; 1 copy of BoAg | 20"+4D'+BoAg' |
| B-2 | 43; 1 copy of T1RS.1BL, 1 copy of 1B; 1 copy of BoAg | 21"+BoAg" |
| B-3 | 42; 1 copy of T1RS.1BL, 1 copy of 1B; 1 copy of 4D; 1 copy of BoAg | 20"+4D'+BoAg' |
| B-4 | 42; 1 copy of T1RS.1BL, 1 copy of 1B; 1 copy of 4D; 1 copy of BoAg | 20"+4D'+BoAg' |
| B-5 | 42; 1 copy of T1RS.1BL, 1 copy of 1B; 1 copy of 4D; 1 copy of BoAg | 20"+4D'+BoAg' |
| C-1 | 42; 1 pair of T1RS.1BL; 1 copy of 4D; 1 copy of BoAg | 20"+4D'+BoAg' |
| C-2 | 42; 1 pair of T1RS.1BL; 1 copy of 4D; 1 copy of BoAg | 20"+4D'+BoAg' |
| C-3 | 42; 1 pair of T1RS.1BL; 1 copy of 4D; 1 copy of BoAg | 20"+4D'+BoAg' |
| C-4 | 42; 1 pair of T1RS.1BL; 1 copy of 4D; 1 copy of BoAg | 20"+4D'+BoAg' |
| E-1 | 43; 1 copy of T1RS.1BL, 1 copy of 1B; 1 telo of BoAgL | 21"+ telo BoAgL' |
| E-2 | 42; 1 copy of mod. T1RS.1BL, 1 copy of 1B; 1 copy of 4B; 1 copy of normal 1D, 1 copy of mod. 1D; 1 copy of mod. BoAg | 18"+1B'+T1RS.1BL-1DL'+4B'+1D'+T1DS.1DL-1BL'+T4DS?-4BoS.4BoL-4AgL' |
| F-1 | 44; 1 pair of T1RS.1BL; 1 pair of normal 3B, 1 mod. 3B; 1 copy of 4B; 3 copies of 6D; 1 copy of BoAg | 18"+3B"+3B (mod)'+4B'+6D'''+BoAg' |
| F-2 | 44; 1 pair of T1RS.1BL; 1 copy of 4B; 1 copy of BoAg | 20"+4B'+BoAg' |
| G-1 | 42; 1 copy of T1RS.1BL, 1 copy of 1B; no BoAg | 21" |
| G-2 | 43; 1 copy of T1RS.1BL, 1 copy of 1B; 1 copy of BoAg | 21"+BoAg" |
| H-2 | 43; 1 copy of T1RS.1BL, 1 copy of 1B; 1 copy of BoAg | 21"+BoAg" |
| H-4 | 43; 1 copy of T1RS.1BL, 1 copy of 1B; 1 copy of BoAg | 21"+BoAg" |
| H-5 | 43; 1 copy of T1RS.1BL, 1 copy of 1B; 1 copy of BoAg | 21"+BoAg" |

Figure 11
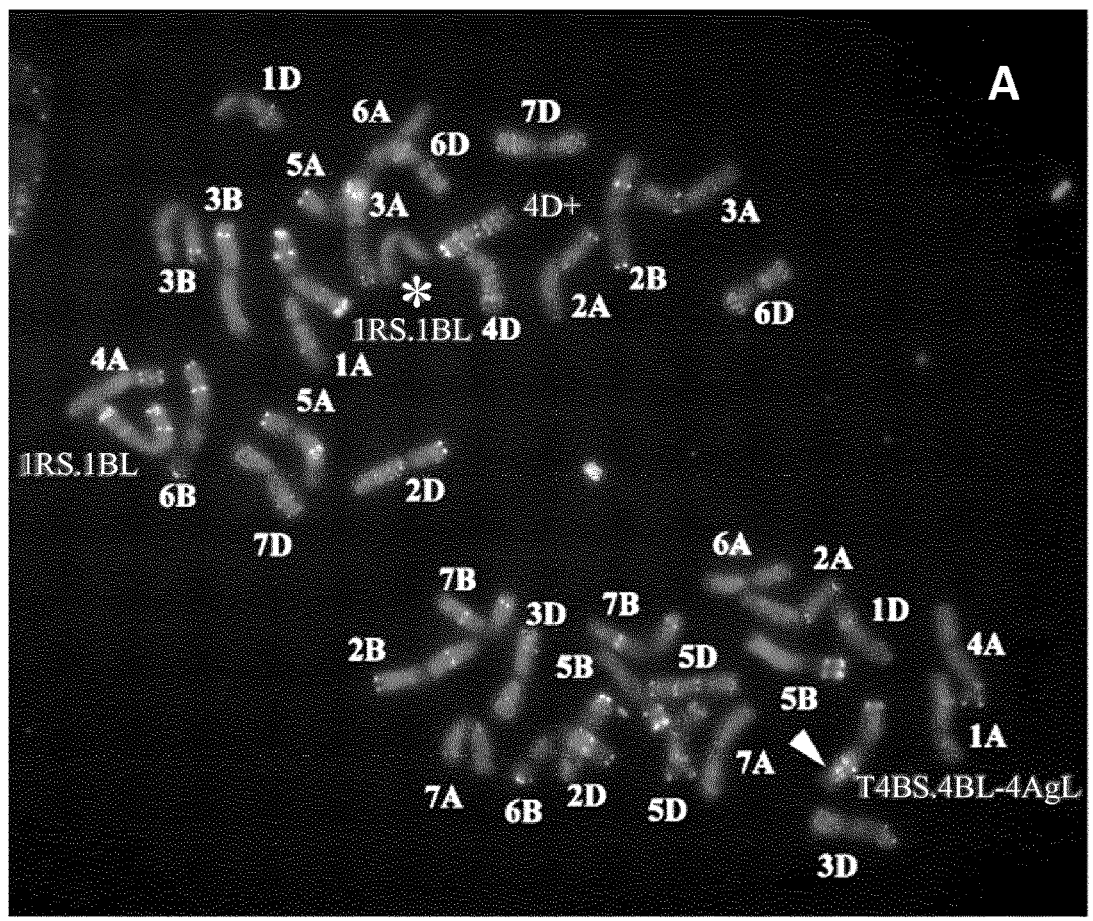
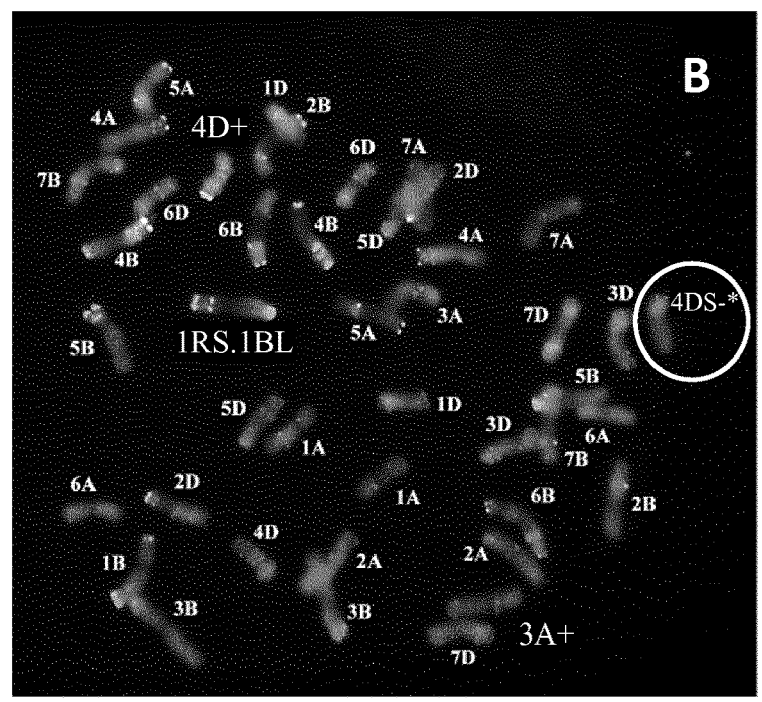

Alien chromosome  Line P4-8-1  Line 50-2  Line 50-3

Figure 15
A
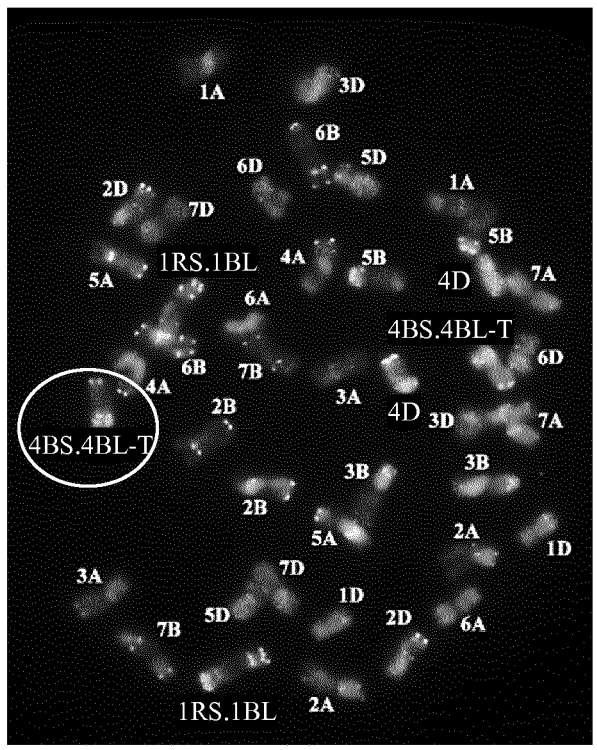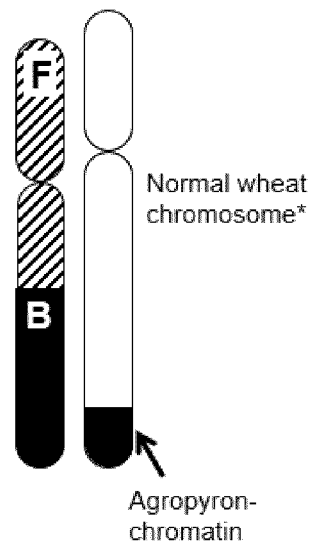
B
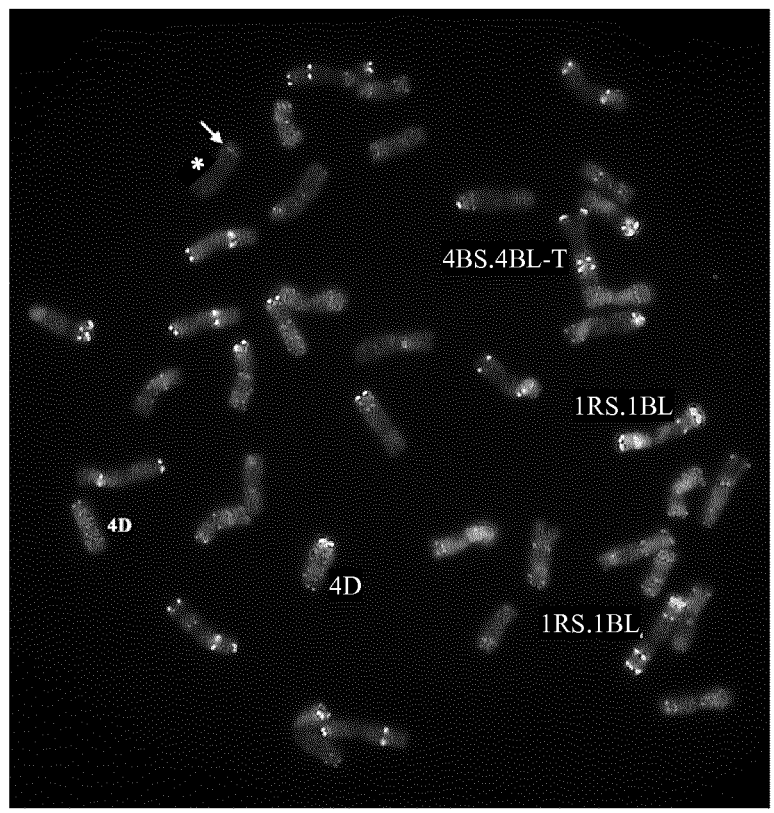

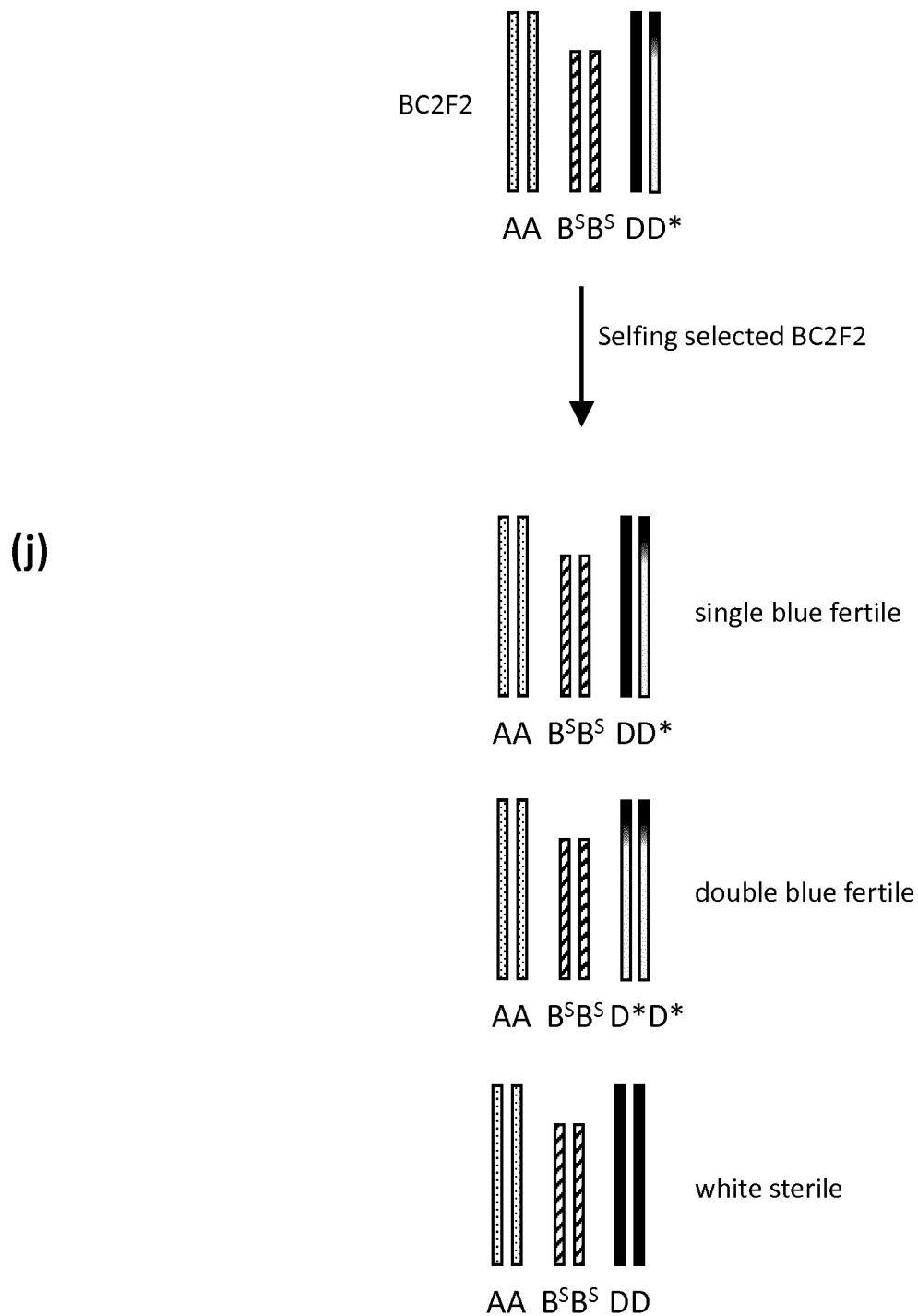

BLUE ALEURONE AND OTHER SEGREGATION SYSTEMS

CROSS-REFERENCE TO RELATED APPLICATIONS

This application is a U.S. National Phase of International Patent Application No. PCT/EP2018/073282, filed on Aug. 29, 2018, which claims priority to U.S. Provisional Application No. 62/551,599, filed Aug. 29, 2017 and U.S. Provisional Application No. 62/610,727, filed Dec. 27, 2017. The entire contents of these applications are incorporated herein by reference in their entirety.

BACKGROUND OF THE INVENTION

1. Technical Field

This invention relates to materials and methods for creating and maintaining a cereal plant line for the production of a hybrid cereal plant, that include for example, and not limitation, using the BLue Aleurone (BLA) system.

2. Background and Related Art

Essential for any hybrid system is the production of male-sterile female parents. WO 92/01366 A1 from Pacific Seeds Pty. Ltd. discloses a male sterility system which allows the maintenance of male sterility that can be used in the production of hybrid cereal plants, in particular hybrid wheat plants (FIG. 1B). Male sterility can be achieved by possessing a homozygous deletion on the short arm of chromosome 4B in wheat. The deletion typically used is the well-known 'Probus' deletion (Fossati A, Ingold M. 1970. A male sterile mutant in *Triticum aestivum*. Wheat Inform Serv 30:8-10). Recently, the ms1 gene located in the region concerned by the deletion has been identified as the causative gene. If this gene is deleted physically or knocked out/down by a mutation or targeted modification (e.g. WO 2016/048891 A1, which is incorporated herein in its entirety for all intended purposes) then a reliable male sterility can be established. Fertility can then be easily restored when a wheat line carrying homozygously the deletion or the mutation/modification, is crossed with any normal wheat. Resulting progenies or hybrids are fertile as the deletion or the mutation/modification is only heterozygously present. Thus, plants or plant lines comprising the above deletion or mutation/modification are suitable for use in producing hybrid plants. However, in order to maintain the male-sterile female parent further components are needed. As such, WO 92/01366 teaches the use of a male parent that is isogenic to the female but having an alien addition chromosome bearing a dominant male fertility restorer gene from *Triticum boeticum* (trivial name is *Triticum thaoudar*) on the short arm and the BLue Aleurone (BLA) gene from *Agropyron elongatum* on the long arm (FIG. 1A), in a cross with the female parent for maintenance of the male sterile female parent, whereby the BLA gene, if expressed, confers a characteristic blue coloration of the progeny seed. Recent studies indicate that the alien addition chromosome may bear also chromatin of *Triticum aestivum* (FIG. 1C). After harvest from that cross, a population of progeny seeds, consisting of a mixture of the two parents, it is possible to physically separate the progeny seeds on the basis of the color marker, whereby, in theory, white seeds are still male-sterile due to the defect in the ms1 gene (deletion or mutation/modification) and free of the alien addition chromosome. These white seeds can be used as female parents in subsequent hybrid wheat production. The harvested blue seeds can be used as male parents for maintenance breeding.

Typically, bread wheat has three genomes, each containing seven individual chromosomes in diploid leading in a total number of 42 chromosomes. As the above BLA system contains a single additional chromosome, the chromosomal status of the blue seed producing wheat plant is 42+1 chromosomes. WO 92/01366 describes already that the transmission of the alien addition chromosome through the gametes seems to be difficult, because this transmission does not occur normally and does not correspond to the result expected from a classical Mendelian ratio. Consequently, the generation of wheat seeds with the desired chromosomal status is less efficient and requires an enhanced screening effort. In order to avoid the observed meiotic instability, a 42 chromosomes system is desirable. WO 93/13649 discloses different ways to establish such a system wherein via homoeologous pairing parts of one homoeologue of chromosome 4B in wheat have been substituted by alien wheat chromatin carrying a gene for restoration of male sterility and one or more marker genes from e.g., *Agropyron elongatum*, *Triticum monococcum*, or *Triticum thaoudar*. In order to force homoeologous pairing the use of a mutant wheat line carrying a mutated gene encoding for a suppressor of pairing (ph1b) located on the long arm of chromosome 5B is suggested (Sears E. R. (1977). Induced mutant with homoeologous pairing in common wheat. *Can. J. Genet. Cytol.* 19 585-593.; [accession no.: TA3809 in WGRC at Kansas State University]). In that application, several examples are presented on how such a system might be established; however, the proposed breeding steps are complex and rely on the use of an undesired nullisomy and monosomic chromosomes. While it is known that bread wheat can tolerate nullisomy as the four homoeologous chromosomes apparently compensate for a missing pair of homologs, their appearances and phenotypes differ significantly from the normal hexaploids and furthermore, most of the nullisomics grow less vigorously and exhibit other developmental deficiencies. Monosomic chromosome complements are generally deleterious for two main reasons. First, the missing chromosome perturbs the overall gene balance in the chromosome set. Second, having a chromosome missing allows any deleterious recessive allele on the single chromosome to be hemizygous and thus to be directly expressed phenotypically. Notice that these are the same effects produced by deletions. The extended use of monosomics and nullosomics in parent plants proposed in several individual crossing steps is impeding the conduct of methods for the generation of the 42 chromosomes system having the alien addition chromosome translocated into the genome. The successful application of the proposed methods seems to be rather unlikely. Therefore, it is also not surprising that until now, with this application, such 42 chromosomes system has never been achieved.

As mentioned above, the WO 92/01366 male parent plant comprising the alien addition chromosome is suitable to be used for maintenance of male sterile females. From the described cross the white seeds can be selected for further use in hybrid wheat production and the blue seeds can be used for maintenance breeding. For this 42+1 chromosome system to work on a commercial scale it is necessary that the white coloration of the seeds is strictly linked to male sterility. This is the only way to ensure a reliable hybridization between the male-sterile female and the optimized male parent in order to achieve a maximum benefit of the heterosis effect also in wheat. The alien and unpaired chromosome is, however, unstable.

With regard to the alien addition chromosome mis-division occurs in 1-2% and leads to two teleocentric chromosomes, one carrying the blue aleuron gene and one carrying the fertility restorer without blue color marker (FIG. 2). The result of the mis-division is that blue seeds, which are male-sterile, and white seeds, which are fertile, appear. The consequences are drastic, in that use of plants grown from the sterile blue seeds in a cross with male-sterile female for maintenance leads to sterile plants so that maintenance is interrupted, and use of plants grown from the fertile white seeds in a cross with an adequate male parent is leading to impaired and poor hybridization due to self-fertilization of the female plant and undesired pollinating of other isogenic females. Both result in an increased, significantly more than the 1-2% amount of seeds growing on the female parent, whereby the seeds representing only the genotype of the female parent, not the F1 generation with the expected heterosis effect. Thus, the farmer would suffer yield loss, which might off-set the expected heterosis-based yield increase. The color markers characteristic cannot be used to eliminate such unwanted seeds from the seed populations. The only way is the cytogenetical determination of the break of the alien addition chromosome. This is however extremely time-consuming and labor-intensive at present. Therefore, the currently available 42+1 chromosome system is not applicable in a commercial context.

As such, there is a need for further improvement the 42+1 chromosome system, in particular with regard to the rearrangement or translocation of the alien addition chromosome. For that robust methods for generation of a system is desired which can be used on commercial scale, i.e. which can benefit optimal from the color marker BLA.

SUMMARY OF THE INVENTION

As specified in the Background Section, there is a great need in the art to identify technologies for creating and maintaining a cereal plant line for the production of a hybrid cereal plant, and use of this understanding to develop novel methods for such engineering. The present invention satisfies this and other needs. Embodiments of the present invention relate generally to methods and materials for improving the current 42+1 chromosome system, including for example and not limitation, rearrangement or translocation of the alien addition chromosome and/or alien chromosome fragments. In certain embodiments, the system can utilize a selection marker (e.g., color marker) for ease of detection.

To improve the 42+1 chromosome system mis-division of the chromosome leading to unmarked (e.g., white colored) fertile seeds and to a lesser extent plants from marked (e.g., blue colored) sterile seeds needs to be prevented. This can be done by rearranging the monosomic alien addition chromosome, so that the male fertility restoration gene would be associated with the selection marker gene and located on one chromosome arm (see FIG. 3). Mis-division could still occur, but it would not lead to unmarked fertile seed. The rearrangement of an alien addition chromosome within itself could be achieved by gametocidal (Gc) genes, irradiation, and/or gene editing.

In an alternative system, the rearrangement would lead to a hybrid system with the aforementioned characteristics within a 42 chromosome genome, i.e. the alien addition chromosome is translocated into the genome of the cereal plant. The selection marker gene is associated with the fertility restoring gene (i.e., linked), and included into the 42 chromosomes of the genome (see FIG. 4). This translocation could be achieved by homoeologous pairing (e.g., ph1b assisted) and/or gene editing.

The present invention is in particular captured by any one or any combination of one or more of the below numbered items [001] to [231], with any other item and/or embodiments.

[001] A cereal plant for use in the production of hybrid cereal plants, wherein the cereal plant comprises a monosomic alien addition chromosome carrying a male fertility restorer gene and at least one selection marker gene, wherein the male fertility restorer gene and the at least one selection marker gene are on the same side of the centromere of the monosomic alien addition chromosome. In a particular embodiment the alien addition chromosome contains a portion of chromatin which is native to the cereal plant, wherein said chromatin does not carry the male fertility restorer gene and/or the at least one selection marker gene.

[002] The cereal plant of [001], wherein the male fertility restorer gene is a dominant gene.

[003] The cereal plant of [001] or [002], wherein the cereal plant is a tetraploid wheat, a hexaploid wheat, triticale, maize, rice, barley, or oats.

[004] The cereal plant of [003], wherein the cereal plant is a triticale.

[005] The cereal plant of [003], wherein the cereal plant is a tetraploid wheat or a hexaploid wheat.

[006] The cereal plant of [005], wherein the cereal plant is a *Triticum durum* or *Triticum aestivum*.

[007] The cereal plant of any one of [001] to [006], wherein the male fertility restorer gene is from *Triticum boeoticum* or *Triticum monococcum*.

[008] The cereal plant of any one of [001] to [007], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[009] The cereal plant of any one of [001] to [008], wherein the selection marker gene is selected from the group consisting of a color marker gene, a plant height gene, or a texture gene.

[010] The cereal plant of [009], wherein the color marker gene is able to confer a characteristic coloration of a progeny seed comprising the color marker gene.

[011] The cereal plant of [009] or [010], wherein the color marker gene is a blue aleurone gene.

[012] The cereal plant of [011], wherein the blue aleurone gene is from *Agropyron elongatum, Agropyron trichophorum*, or *Triticum monococcum*.

[013] The cereal plant of [012], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[014] The cereal plant of any one of [001] to [013], wherein the cereal plant comprises homozygously a male fertility gene mutation.

[015] The cereal plant of [014], wherein the male fertility gene mutation is a gene deletion, a gene knockdown, or a gene knockout.

[016] The cereal plant of any one of [001] to [015], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[017] The cereal plant of any one of [001] to [016], wherein the cereal plant comprises one additional chromosome to its euploid number of chromosomes, wherein the dominant male fertility restorer gene and at least one selection marker gene are on the additional chromosome.

[018] The cereal plant of [017], wherein the male fertility restorer gene is located in a similar location on the alien addition chromosome as the mutated male fertility gene of the cereal plant.

[019] Seed or progeny or a part thereof of the cereal plant of any one of [001] to [018].

[020] Seed or progeny or a part thereof of [019], wherein the seed, progeny or part thereof comprises at least the male fertility restorer gene and at least one selection marker gene on the same side of the centromere of the monosomic alien addition chromosome.

[021] Seed, progeny or a part thereof of [019], wherein the seed, progeny or part thereof comprises at least one additional chromosome to its euploid number and wherein the male fertility restorer gene and at least one selection marker gene are on the additional chromosome.

[022] Seed or progeny or a part thereof of [019], wherein the seed, progeny or part thereof comprises homozygously the male fertility gene mutation, wherein preferably the male fertility gene mutation is the ms1 gene deletion, ms1 gene knockdown, or ms1 gene knockout.

[023] A cereal plant for use in the production of hybrid cereal plants, wherein the cereal plant comprises at least one homoeologous chromosome pair, wherein the pair consisting of a first and second chromosome, the first chromosome is native to the cereal plant and the second chromosome comprises an alien chromosome fragment comprising a dominant male fertility restorer gene and at least one selection marker gene, wherein the cereal plant comprises a male fertility gene mutation causing male sterility.

[024] The cereal plant of [023], wherein the first chromosome comprises a piece of chromatin of *Agropyron elongatum* as translocation, preferably onto the end of the long arm of the first chromosome, whereby said piece of chromatin pairs to the alien chromosome fragment or a part thereof.

[025] The cereal plant of [023] or [024], wherein the second chromosome further comprises native DNA.

[026] The cereal plant of any one of [023] to [025], wherein the cereal plant consists of a euploid number of chromosomes.

[027] The cereal plant of any one of [023] to [026], wherein the cereal plant is a tetraploid wheat, a hexaploid wheat, triticale, maize, rice, barley, or oats.

[028] The cereal plant of [027], wherein the cereal plant is a triticale.

[029] The cereal plant of [027], wherein the cereal plant is a tetraploid wheat or a hexaploid wheat

[030] The cereal plant of [029], wherein the cereal plant is a *Triticum durum* or *Triticum aestivum*.

[031] The cereal plant of any one of [023] to [030], wherein the cereal plant comprises a mutated homoeologous pairing suppressor gene.

[032] The cereal plant of [031], wherein the homoeologous pairing suppressor gene is deleted.

[033] The cereal plant of [031] or [032], wherein the homoeologous pairing suppressor gene is bred out of the cereal plant.

[034] The cereal plant of any one of [023] to [030], wherein the cereal plant does not comprise a mutated homoeologous pairing suppressor gene.

[035] The cereal plant of any one of [031] to [033], wherein the mutated homoeologous pairing suppressor gene is homozygously present on chromosome 5B or chromosome 3D.

[036] The cereal plant of any one of [031] to [033] or [035], wherein the mutated homoeologous pairing suppressor gene is ph1b or ph2.

[037] The cereal plant of [036], wherein the mutated homoeologous pairing suppressor gene is ph1b.

[038] The cereal plant of any one of [023] to [037], wherein the male fertility restorer gene is from *Triticum boeoticum* or *Triticum monococcum*.

[039] The cereal plant of any one of [023] to [037], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[040] The cereal plant of any one of [023] to [039], wherein the selection marker gene is selected from the group consisting of a color marker gene, a plant height gene, or a texture gene.

[041] The cereal plant of [040], wherein the color marker gene is able to confer a characteristic coloration of a progeny seed comprising the color marker gene.

[042] The cereal plant of [040] or [041], wherein the color marker gene is a blue aleurone gene.

[043] The cereal plant of [042], wherein the blue aleurone gene is from *Agropyron elongatum*, *Agropyron trichophorum*, or *Triticum monococcum*.

[044] The cereal plant of [043], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[045] The cereal plant of any one of [023] to [044], wherein the cereal plant comprises homozygously a male fertility gene mutation.

[046] The cereal plant of [045], wherein the male fertility gene mutation is a gene deletion, a gene knockdown, or a gene knockout.

[047] The cereal plant of any one of [023] to [046], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[048] The cereal plant of any one of [023] to [047], wherein the male fertility restorer gene and selection marker gene are on the opposite sides of the centromere.

[049] The cereal plant of any one of [023] to [047], wherein the male fertility restorer gene and selection marker gene are on the same side of the centromere.

[050] The cereal plant of any one of [023] to [049], wherein the first chromosome is 4A, 4B, 4D, or 5A.

[051] The cereal plant of any one of [023] to [050], wherein the first chromosome is not 4B.

[052] Seed, progeny or a part thereof of the cereal plant of any one of [023] to [051].

[053] A method of generating a blue aleurone (BLA) male sterile system for genomic selection of cereal plants comprising: a) selecting a cereal plant line homozygous for a male fertility gene mutation comprising at least one alien addition chromosome carrying a male fertility restorer gene and a blue aleurone gene on different sides of the centromere of the at least one alien addition chromosome; b) rearranging at least one alien addition chromosome and/or inducing homoeologous recombination of at least one alien addition chromosome; and c) obtaining a cereal plant comprising a rearranged and/or homoeologous alien addition chromosome. Preferably, a cereal plant according to any one of [001] to [018] or [023] to [051] are obtained in step c). In a particular embodiment the alien addition chromosome contains a portion of chromatin which is native to the cereal plant, wherein said chromatin does not carry the male fertility restorer gene and/or blue aleurone gene.

[054] The method of [053], wherein the male fertility restorer gene is a dominant gene.

[055] The method of [053] or [054], wherein the male fertility gene mutation is a deletion, knockdown, or knockout.

[056] The method of any one of [053] to [055], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[057] The method of any one of [053] to [056], wherein the male fertility mutation is an ms1 gene deletion, ms1 gene knockdown, or ms1 gene knockout.

[058] The method of any one of [053] to [057], wherein the alien addition chromosome is monosomic.

[059] The method of any one of [053] to [057], wherein the alien addition chromosome is disomic.

[060] The method of any one of [053] to [059], wherein the rearranging step b) comprises the presence of a gametocidal gene to the cereal plant line of step a).

[061] The method of [060], wherein the gametocidal gene is introduced as a monosomic addition chromosome.

[062] The method of [060] or [061], wherein the gametocidal gene induces breakage and rearrangement of at least one alien addition chromosome.

[063] The method of any one of [060] to [062], wherein the gametocidal gene is the gametocidal factor located on chromosome 4M$^g$ of *Aegilops geniculate* or 2C$^c$ of *Aegilops cylindrica*.

[064] The method of any one of [053] to [059], wherein the rearranging step b) comprises irradiating seeds of the cereal plant line of step a).

[065] The method of [064], wherein irradiating seeds induces chromosomal rearrangement of at least one alien addition chromosome.

[066] The method of [064] or [065], wherein the seeds are irradiated with 175, 200, 225, or 250 Gy of γ-rays.

[067] The method of any one of [064] to [066], wherein the seeds are irradiated from about 40 to about 50 minutes.

[068] The method of any one of [053] to [059], wherein the rearranging step b) comprises gene editing of the cereal plant line of step a).

[069] The method of [068], wherein gene editing comprises inserting the same or a different blue aleurone gene on the same side of the centromere of the at least one alien addition chromosome as the male fertility restorer gene.

[070] The method of [069], wherein inserting comprises introducing into a cell of the cereal plant line of step a) a gene cassette carrying the same or different blue aleurone gene and a site-specific nuclease designed to make a -strand break at a target site in the cereal plant line genome on the same side of the centromere of the at least one alien addition chromosome as the male fertility restorer gene and wherein the same or different blue aleurone gene is integrated into the cereal plant line genome at the site of the double-strand break.

[071] The method of any one of [068] to [070], wherein the blue aleurone gene on the different side of the centromere of the at least one alien addition chromosome as the male fertility restorer gene is disrupted.

[072] The method of [068], wherein gene editing comprises inserting the same or a different male fertility restorer gene on the same side of the centromere of the at least one alien addition chromosome as the blue aleurone gene.

[073] The method of [072], wherein inserting comprises introducing into a cell of the cereal plant line of step a) a gene cassette carrying the same or different male fertility restorer gene and a site-specific nuclease designed to make a double-strand break at a target site in the cereal plant line genome on the same side of the centromere of the at least one alien addition chromosome as the blue aleurone gene and wherein the same or different male fertility restorer gene is integrated into the cereal plant line genome at the site of the double-strand break.

[074] The method of any one of [068] or [072] to [074], wherein the male fertility restorer gene on the different side of the centromere of the at least one alien addition chromosome as the blue aleurone gene is disrupted.

[075] The method of [068], wherein gene editing comprises introducing at least two different site-specific nucleases into a cell of the cereal plant line of step a), wherein at least one site-specific nuclease makes a first double strand break close to the blue aleurone gene but between the blue aleurone gene and the end of the chromosome of the alien addition chromosome to create a first end of the chromosome and at least one other site-specific nuclease makes a second double strand break close to the male fertility restorer gene but between the male fertility restorer gene and the centromere of the alien addition chromosome to create a second chromosome end, and wherein the chromosome ends are swapped so that the blue aleurone gene is on the same side of the centromere of the at least one alien addition chromosome as the male fertility restorer gene.

[076] The method of [068], wherein gene editing comprises introducing at least two different site-specific nucleases into a cell of the cereal plant line of step a), wherein at least one site-specific nuclease makes a first double strand break close to the male fertility restorer gene but between the male fertility restorer gene and the end of the chromosome of the alien addition chromosome to create a first end of the chromosome and at least one other site-specific nuclease makes a second double strand break close to the blue aleurone gene but between the blue aleurone gene and the centromere of the alien addition chromosome to create a second chromosome end, and wherein the chromosomes ends are swapped so that the blue aleurone gene is on the same side of the centromere of the at least one alien addition chromosome as the male fertility restorer gene.

[077] The method of [075] or [076], wherein the first and second double strand breaks occur simultaneously or in close proximity in time.

[078] The method of any one of [070], [071], or [073] to [077], wherein the site-specific nuclease is a meganuclease, a TALEN, a ZFN, or a CRISPR nuclease.

[079] The method of [078], wherein the site-specific nuclease is delivered into the cereal plant line cell by transformation of at least one DNA cassette encoding the required genes for site-specific nuclease activity, transformation of RNA molecules, or by transformation of purified protein or ribonucleoprotein complexes.

[080] The method of any one of [070], [071], [073] to [080], wherein the cell comprises a male-sterile genotype.

[081] The method of any one of [070], [071], [073] to [080], wherein the cell is from an immature embryo or a callus.

[082] The method of [053], wherein the inducing homoeologous recombination step b) comprises the presence of a mutated homoeologous pairing suppressor gene or introducing a gene which suppresses the homoeologous pairing suppressor gene, wherein the homoeologous pairing suppressor gene induces the homoeologous recombination of the alien addition chromosome comprising the dominant male fertility restorer gene and at least one selection marker, with at least one homoeologous chromosome.

[083] The method of [082], wherein the at least one homoeologous chromosome is 4A, 4B, 4D, or 5A.

[084] The method of [082] wherein the at least one homoeologous chromosome is not 4B.

[085] The method of any one of [082] to [084], wherein the mutated homoeologous pairing suppressor gene is homozygously present on chromosome 5B or chromosome 3D.

[086] The method of any one of [082] to [085], wherein the mutated homoeologous pairing suppressor gene is deleted.

[087] The method of any one of [082] to [086], wherein the mutated homoeologous pairing suppressor gene is ph1b or ph2.

[088] The method of any one of [053] to [087], wherein the cereal plant or progeny thereof is a tetraploid wheat, a hexaploid wheat, triticale, maize, rice, barley, or oats.

[089] The method of [088], wherein the cereal plant is a triticale.

[090] The method of [088], wherein the cereal plant is a tetraploid wheat or a hexaploid wheat

[091] The method of [090], wherein the cereal plant is a *Triticum durum* or *Triticum aestivum*.

[092] The method of any one of [053] to [091], wherein the male fertility restorer gene is from *Triticum boeoticum* or *Triticum monococcum*.

[093] The method of any one of [053] to [091], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[094] The method of [093], wherein the blue aleurone gene is from *Agropyron elongatum, Agropyron trichophorum,* or *Triticum monococcum*.

[095] The method of [094], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[096] A cereal plant or part thereof, wherein the cereal plant is obtained from step c) of any one of [053] to [095], and wherein the cereal plant does not comprise a mis-division of the alien addition chromosome.

[097] A cereal plant or part thereof, wherein the cereal plant is obtained from step c) of any one of [053] to [095], and wherein the cereal plant does not comprise a breakage of the alien addition chromosome.

[098] A cereal plant or part thereof, wherein the cereal plant is obtained from step c) of any one of [053] to [095], and wherein the cereal plant does not comprise i) a mis-division of the alien addition chromosome and ii) a breakage of the alien addition chromosome.

[099] Seed or progeny or a part thereof, obtained from a cereal plant obtained from step c) of any one of [053] to [095], and wherein the seed or progeny or a part thereof does not comprise a mis-division of the alien addition chromosome.

[100] Seed or progeny or a part thereof, obtained from a cereal plant obtained from step c) of any one of [053] to [095], and wherein the seed or progeny or a part thereof does not comprise a breakage of the alien addition chromosome.

[101] Seed or progeny or a part thereof, obtained from a cereal plant obtained from step c) of any one of [053] to [095], and wherein the seed or progeny or a part thereof does not comprise i) a mis-division of the alien addition chromosome and ii) a breakage of the alien addition chromosome.

[102] A method of generating a blue aleurone (BLA) male sterile system for genomic selection of cereal plants comprising: a) selecting a cereal plant line homozygous for a male fertility gene mutation; b) integrating into the genome of the cereal plant line a male fertility restorer gene and a blue aleurone gene, wherein the male fertility restorer gene and the blue aleurone gene are genetically linked and in close proximity; and c) obtaining a cereal plant comprising the genetically linked male fertility restorer gene and blue aleurone gene. Preferably, such a blue aleurone (BLA) male sterile system for genomic selection of cereal plants, comprises a cereal plant according to any one of [001] to [018] or [023] to [051] as obtained in step c).

[103] The method of [102], wherein the male fertility restorer gene and the blue aleurone gene are introduced into a cell of the cereal plant line via a gene cassette.

[104] The method of [103], wherein the male fertility restorer gene and the blue aleurone gene are configured in the gene cassette as 5' to 5', 3' to 3', 5' to 3', or 3' to 5'.

[105] The method of any one of [102] to [104], wherein the male fertility restorer gene and the blue aleurone gene are linked via a linker.

[106] The method of any one of [103] to [105], wherein the cell comprises a male-sterile genotype.

[107] The method of any one of [103] to [106], wherein the cell is from an immature embryo or a callus.

[108] The method of any one of [102] to [107], wherein the integrating step b) comprises integrating the linked male fertility restorer gene and blue aleurone gene randomly.

[109] The method of [108], wherein the gene cassette is introduced into the cell by *Agrobacterium*-mediated transformation of the male fertility restorer gene and blue aleurone gene harbored within T-DNA borders in a binary plasmid.

[110] The method of [108], wherein the gene cassette is introduced into the cell by particle bombardment of a plasmid comprising the gene cassette in supercoiled, circular, relaxed, or linear configurations.

[111] The method of any one of [102] to [107], wherein the integrating step b) comprises targeting the integration of the linked male fertility restorer gene and blue aleurone gene using a site-specific nuclease designed to make a double-strand break at a target site in the cereal plant line genome and wherein the linked male fertility restorer gene and blue aleurone gene is integrated into the cereal plant line genome at the site of the double-strand break.

[112] The method of [111], wherein the site-specific nuclease is a meganuclease, a TALEN, a ZFN, or a CRISPR nuclease.

[113] The method of [112], wherein the site-specific nuclease is delivered into the cereal plant line cell by transformation of at least one DNA cassette encoding the required genes for site-specific nuclease activity, transformation of RNA molecules, or by transformation of purified protein or ribonucleoprotein complexes.

[114] The method of any one of [102] to [113], wherein the male fertility restorer gene is a dominant gene.

[115] The method of any one of [102] to [114], wherein the male fertility gene mutation is a deletion, knockdown, or knockout.

[116] The method of any one of [102] to [115], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[117] The method of any one of [102] to [114], wherein the male fertility mutation is an ms1 gene deletion, ms1 gene knockdown, or ms1 gene knockout.

[118] The method of any one of [102] to [117], wherein the linked male fertility restorer gene and blue aleurone gene are integrated into chromosome 4A, 4B, 4D, or 5A.

[119] The method of any one of [102] to [117], wherein the linked male fertility restorer gene and blue aleurone gene are not integrated into chromosome 4B.

[120] The method of any one of [102] to [119], wherein the cereal plant or progeny thereof is a tetraploid wheat, a hexaploid wheat, triticale, maize, rice, barley, or oats.

[121] The method of [120], wherein the cereal plant is a triticale.

[122] The method of [120], wherein the cereal plant is a tetraploid wheat or a hexaploid wheat

[123] The method of [122], wherein the cereal plant is a *Triticum durum* or *Triticum aestivum*.

[124] The method of any one of [102] to [123], wherein the male fertility restorer gene is from *Triticum boeoticum* or *Triticum monococcum*.

[125] The method of any one of [102] to [124], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[126] The method of [102] to [125], wherein the blue aleurone gene is from *Agropyron elongatum, Agropyron trichophorum,* or *Triticum monococcum*.

[127] The method of [126], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[128] A cereal plant or part thereof, wherein the cereal plant is obtained from step c) of any one of [102] to [127] and wherein the cereal plant comprises a single-copy insertion of the linked male fertility restorer gene and blue aleurone gene.

[129] A cereal plant or part thereof, wherein the cereal plant is obtained from step c) of any one of [102] to [127] and wherein the native gene sequences of the cereal plant are not disrupted.

[130] Seed or progeny or a part thereof, obtained from the cereal plant obtained from step c) of any one of [102] to [127] and wherein the cereal plant comprises a single-copy insertion of the linked male fertility restorer gene and blue aleurone gene.

[131] Seed or progeny or a part thereof, obtained from the cereal plant obtained from step c) of any one of [102] to [127] and wherein the native gene sequences of the cereal plant are not disrupted.

[132] A method for manufacturing a cereal plant, seed or part thereof, for the production of a hybrid cereal plant, comprising: a) crossing a first cereal plant comprising a monosomic alien addition chromosome carrying a dominant male fertility restorer gene and at least one selection marker gene on different sides of the centromere of the monosomic alien addition chromosome and a homozygous male fertility gene mutation with a second cereal plant comprising a disomic gametocidal addition chromosome carrying a gametocidal gene; b) harvesting, selecting, and planting at least one seed produced by step a) expressing the selection marker gene, wherein the seed comprises the monosomic alien addition chromosome and a monosomic gametocidal addition chromosome to produce a third cereal plant, wherein the third cereal plant comprises a heterozygous male fertility gene mutation; c) crossing the third cereal plant produced in step b) with the first cereal plant of step a); d) harvesting, selecting, and planting at least one seed produced in step c) expressing the selection marker gene, wherein the seed comprises the monosomic alien addition chromosome and homozygous male fertility gene mutation to generate a progeny cereal plant of the first filial generation comprising a homozygous male fertility gene mutation; e) self-fertilizing the progeny cereal plant of the first filial generation produced in step d); f) harvesting, selecting, and planting at least one seed produced in step e) expressing the selection marker gene, wherein the seed comprises the monosomic alien addition chromosome and homozygous male fertility gene mutation to generate a progeny cereal plant of the second filial generation; g) self-fertilizing the progeny cereal plant of the second filial generation produced in step f); h) optionally repeating steps f) and g) for at least one additional generation; i) harvesting seeds of the third filial generation produced in step g) or h), if step h) is performed; j) selecting and planting at least one seed of the third filial generation not expressing the selection marker gene to generate a progeny cereal plant of the fourth filial generation; k) phenotyping the ears of the cereal plant of the fourth filial generation produced in step j); and 1) selecting a population of cereal plants of the fourth filial generation showing complete sterility in step k) to generate a cereal plant for the production of a hybrid cereal plant. In a particular embodiment the alien addition chromosome contains a portion of chromatin which is native to the cereal plant, wherein said chromatin does not carry the male fertility restorer gene and/or the at least one selection marker gene.

[133] The method of [132], wherein step j) comprises selecting and planting at least 25 seeds or at least 100 seeds.

[134] A method for manufacturing a cereal plant, seed or part thereof, for the production of a hybrid cereal plant, comprising: a) irradiating at least one seed comprising a monosomic alien addition chromosome carrying a dominant male fertility restorer gene and at least one selection marker gene on different sides of the centromere; b) planting the at least one seed irradiated in step a) to produce at least one first cereal plant; c) harvesting essentially all the seeds from the at least one first cereal plant produced in step b) to create at least one population of seeds, wherein each population of seeds are from one individual plant and wherein each population of seeds comprise seeds expressing the at least one selection marker gene and seeds not expressing the at least one selection marker gene; d) planting at least one seed not expressing the selection marker gene from the population of step c); e) discarding a population of seeds which produce a fertile plant in step d); f) self-fertilizing the seeds expressing the selection marker gene that were not discarded in step e) to create a next population of seeds, wherein each population of seeds are from one individual plant, wherein each population of seeds comprise seeds expressing the at least one selection marker gene and seeds not expressing the at least one selection marker gene; g) optionally repeating steps d) and e) at least once; h) planting at least one seed not expressing the at least one selection marker; and i) selecting a population of seeds from a population of cereal plants showing complete sterility to generate a cereal plant for the production of a hybrid cereal plant. In a particular embodiment the alien addition chromosome contains a portion of chromatin which is native to the cereal plant, wherein said chromatin does not carry the male fertility restorer gene and/or the at least one selection marker gene.

[135] The method of [134], wherein step a) comprises irradiating at least 1000 or at least 8000 seeds.

[136] The method of [134] or [135], wherein step d) comprises planting up to 200 seeds.

[137] The method of any of [134] to [136], wherein step g) repeats step d) comprising planting of at least 300 seeds.

[138] The method of any one of [132] to [137], further comprising examining at least one selection marker gene expressing seed from the population of step 1) of [132] or step i) of [134] to confirm the seed comprises a rearranged monosomic alien addition chromosome, which comprises the dominant male fertility restorer gene and the selection marker gene on the same side of the centromere of the rearranged monosomic alien addition chromosome.

[139] The method of [138], wherein the examining step comprises conducting a cytological analysis or molecular analysis.

[140] The method of [139], wherein the examining step comprises conducting FISH (fluorescence in-situ hybridization) or GISH (genomic in-situ hybridization) microscopy to detect the location of translocation.

[141] The method of any one of [132] to [140], further comprising selecting and crossing at least one hybrid cereal plant from the population of step 1) of [132] or step i) of [134] comprising the rearranged monosomic alien addition chromosome with a cereal plant not treated by one of the method of [132] or [134] to reduce in a progeny any unwanted chromosomal rearrangement or mutations introduced into the cereal genome as a result of the methods of [132] or [134].

[142] The method of any one of [132] to [141], wherein the cereal plant or progeny thereof is a tetraploid wheat, a hexaploid wheat, triticale, maize, rice, barley, or oats.

[143] The method of [142], wherein the cereal plant is a triticale.

[144] The method of [142], wherein the cereal plant is a tetraploid wheat or a hexaploid wheat

[145] The method of [144], wherein the cereal plant is a *Triticum durum* or *Triticum aestivum*.

[146] The method of any one of [132] to [145], wherein the male fertility restorer gene is from *Triticum boeoticum* or *Triticum monococcum*.

[147] The method of any one of [132] to [145], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[148] The method of any one of [132] to [147], wherein the selection marker gene is selected from the group consisting of a color marker gene, a plant height gene, or a texture gene.

[149] The method of [148], wherein the color marker gene is able to confer a characteristic coloration of a progeny seed comprising the color marker gene.

[150] The method of [148] or [149], wherein the color marker gene is a blue aleurone gene.

[151] The method of [150], wherein the blue aleurone gene is from *Agropyron elongatum, Agropyron trichophorum,* or *Triticum monococcum*.

[152] The method of [151], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[153] The method of any one of [132] to [152], wherein the male fertility gene mutation is a gene deletion, a gene knockdown, or a gene knockout.

[154] The method of any one of [132] to [153], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[155] A cereal plant or part thereof, wherein the cereal plant is obtained from any one of [132] to [154], and wherein the cereal plant does not comprise a mis-division of the alien addition chromosome.

[156] A cereal plant or part thereof, wherein the cereal plant is obtained from any one of [132] to [154], and wherein the cereal plant does not comprise a breakage of the alien addition chromosome.

[157] A cereal plant or part thereof, wherein the cereal plant is obtained from any one of [132] to [154], and wherein the cereal plant does not comprise i) a mis-division of the alien addition chromosome and ii) a breakage of the alien addition chromosome.

[158] Seed or progeny or a part thereof, obtained from a cereal plant obtained from any one of [132] to [154], and wherein the seed or progeny or a part thereof does not comprise a mis-division of the alien addition chromosome.

[159] Seed or progeny or a part thereof, obtained from a cereal plant obtained from any one of [132] to [154], and wherein the seed or progeny or a part thereof does not comprise a breakage of the alien addition chromosome.

[160] Seed or progeny or a part thereof, obtained from a cereal plant obtained from any one of [132] to [154], and wherein the seed or progeny or a part thereof does not comprise i) a mis-division of the alien addition chromosome and ii) a breakage of the alien addition chromosome.

[161] A method for manufacturing a cereal plant line, seed or part thereof, for the production of a hybrid cereal plant line, comprising: a) crossing a first cereal plant homozygous for a male fertility gene mutation comprising a disomic alien addition chromosome carrying a dominant male fertility restoration gene and at least one selection marker gene with a second cereal plant homozygous for a male fertility gene mutation and for a homoeologous pairing suppressor gene mutation; b) harvesting, selecting, and planting at least one seed produced in step a) homozygous for a male fertility gene mutation comprising a monosomic alien chromosome carrying a dominant male fertility restoration gene and at least one selection marker gene and a single copy of the homoeologous pairing suppressor gene mutation; c) self-fertilizing a cereal plant produced in step b); d) harvesting, selecting, and planting at least one seed produced in step c) homozygous for a male fertility gene mutation and for the homoeologous pairing suppressor gene mutation comprising a euploid number of chromosomes and the monosomic alien addition chromosome; e) self-fertilizing a cereal plant produced in step d); f) harvesting at least four seeds from step e); g) counting the number of the seeds of step f) from a first group expressing the at least one selection marker and a second group not expressing the at least one selection marker in order to determine the segregation ratio; h) keeping the seeds of step f) if the ratio of the number of seeds of first group:second group tends to about 3:1 and discarding the seeds of step f) if the ratio of the number of seeds of first group:second group tends to about 1:3. In a particular embodiment the alien addition chromosome contains a portion of chromatin which is native to the cereal plant, wherein said chromatin does not carry the male fertility restorer gene and/or the at least one selection marker gene.

[162] The method of [161], wherein the dominant male fertility restoration gene and the at least one selection marker gene are on the same side of the centromere of the alien addition chromosome.

[163] The method of [161], wherein the dominant male fertility restoration gene and the at least one selection marker gene on different sides of the centromere of the alien addition chromosome.

[164] The method of any one of [161] to [163], wherein the cereal plant or progeny thereof is a tetraploid wheat, a hexaploid wheat, triticale, maize, rice, barley, or oats.

[165] The method of [164], wherein the cereal plant is a triticale.

[166] The method of [164], wherein the cereal plant is a tetraploid wheat or a hexaploid wheat

[167] The method of [166], wherein the cereal plant is a *Triticum durum* or *Triticum aestivum.*

[168] The method of any one of [161] to [167], wherein the male fertility restorer gene is from *Triticum boeoticum* or *Triticum monococcum.*

[169] The method of any one of [161] to [167], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[170] The method of any one of [161] to [169], wherein the selection marker gene is selected from the group consisting of a color marker gene, a plant height gene, or a texture gene.

[171] The method of [170], wherein the color marker gene is able to confer a characteristic coloration of a progeny seed comprising the color marker gene.

[172] The method of [170] or [171], wherein the color marker gene is a blue aleurone gene.

[173] The method of [172], wherein the blue aleurone gene is from *Agropyron elongatum, Agropyron trichophorum,* or *Triticum monococcum.*

[174] The method of [174], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[175] The method of any one of [161] to [174], wherein the male fertility gene mutation is a gene deletion, a gene knockdown, or a gene knockout.

[176] The method of any one of [161] to [175], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[177] The method of any one of [161] to [176], wherein the homoeologous pairing suppressor gene mutation is a gene deletion from chromosome 5B or chromosome 3B.

[178] The method of [177], wherein the deleted homoeologous pairing suppressor gene is ph1b or ph2.

[179] The method of any one of [161] to [178], wherein the monosomic alien addition chromosome translocates with 4A, 4B, 4D, or 5A chromosomes.

[180] The method of any one of [161] to [178], wherein the monosomic alien addition chromosome does not translocates with the 4B chromosome.

[181] A cereal plant or part thereof, wherein the cereal plant is obtained from any one of [161] to [180], and wherein the cereal plant does not comprise a mis-division of the alien addition chromosome.

[182] A cereal plant or part thereof, wherein the cereal plant is obtained from any one of [161] to [180], and wherein the cereal plant does not comprise a breakage of the alien addition chromosome.

[183] A cereal plant or part thereof, wherein the cereal plant is obtained from any one of [161] to [180], and wherein the cereal plant does not comprise i) a mis-division of the alien addition chromosome and ii) a breakage of the alien addition chromosome.

[184] Seed or progeny or a part thereof, obtained from a cereal plant obtained from any one of [161] to [180], and wherein the seed or progeny or a part thereof does not comprise a mis-division of the alien addition chromosome.

[185] Seed or progeny or a part thereof, obtained from a cereal plant obtained from any one of [161] to [180], and wherein the seed or progeny or a part thereof does not comprise a breakage of the alien addition chromosome.

[186] Seed or progeny or a part thereof, obtained from a cereal plant obtained from any one of [161] to [180], and wherein the seed or progeny or a part thereof does not comprise i) a mis-division of the alien addition chromosome and ii) a breakage of the alien addition chromosome.

[187] A method for the maintenance of a male-sterile female parental line of a cereal plant for use in the production of hybrid cereal plants, the method comprising: a. planting at least one seed comprising a homozygous male fertility gene mutation and a monosomic alien addition chromosome carrying a dominant male fertility restorer gene and at least one selection marker gene on the same side of the centromere of the monosomic alien addition chromosome, whereby seeds having this monomeric alien addition chromosome can be separated from seeds not having it to produce at least one progeny seed; b. self-fertilizing a cereal plant produced in step a); c. selecting at least one seed not comprising the monosomic alien addition chromosome for growing at least one sterile-female parent cereal plant for crossing with a fertile-male cereal plant for a hybrid cereal plant and a hybrid seed production; and d. selecting at least one seed comprising the monosomic alien addition chromosome for maintenance of the cereal plant. In a particular embodiment the alien addition chromosome contains a portion of chromatin which is native to the cereal plant, wherein said chromatin does not carry the male fertility restorer gene and/or the at least one selection marker gene.

[188] A method for the maintenance of a male-sterile female parental line of a cereal plant for use in the production of hybrid cereal plants, the method comprising: a. planting at least one seed comprising a homozygous male fertility gene mutation and at least one portion of an alien addition chromosome carrying a dominant male fertility restorer gene and at least one selection marker gene translocated into at least one chromosome of a homoeologous chromosome pair; b. self-fertilizing a cereal plant produced in step a); c. selecting at least one seed not comprising the alien addition chromosome translocated into at least one chromosome of a homoeologous chromosome pair for growing at least one sterile-female parent cereal plant for crossing with a fertile-male cereal plant for a hybrid cereal plant and a hybrid seed production; d. selecting at least one seed comprising the alien addition chromosome translocated into one chromosome of a homoeologous chromosome pair for maintenance of the cereal plant, wherein the seed is heterozygous for the translocation as preferably indicated by the expression of the at least one selection marker gene; and e. discarding any seed comprising the alien addition chromosome translocated into at least two chromosomes of a homoeologous chromosome pair for maintenance of the cereal plant, wherein the seed is homozygous for the translocation as preferably indicated by expression of the at least one selection marker gene. In a particular embodiment the alien addition chromosome contains a portion of chromatin which is native to the cereal plant, wherein said chromatin does not carry the male fertility restorer gene and/or the at least one selection marker gene.

[189] The method of [187] or [188], wherein the cereal plant or progeny thereof is a tetraploid wheat, a hexaploid wheat, triticale, maize, rice, barley, or oats.

[190] The method of [189], wherein the cereal plant is a triticale.

[191] The method of [189], wherein the cereal plant is a tetraploid wheat or a hexaploid wheat

[192] The method of [191], wherein the cereal plant is a *Triticum durum* or *Triticum aestivum*.

[193] The method of any one of [187] to [192], wherein the male fertility restorer gene is from *Triticum boeoticum* or *Triticum monococcum*.

[194] The method of any one of [187] to [193], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[195] The method of any one of [187] to [194], wherein the selection marker gene is selected from the group consisting of a color marker gene, a plant height gene, or a texture gene.

[196] The method of [195], wherein the color marker gene is able to confer a characteristic coloration of a progeny seed comprising the color marker gene.

[197] The method of [195] or [196], wherein the color marker gene is a blue aleurone gene.

[198] The method of [197], wherein the blue aleurone gene is from *Agropyron elongatum*, *Agropyron trichophorum*, or *Triticum monococcum*.

[199] The method of [198], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[200] The method of any one of [196] to [199], wherein a light blue seed indicates that the seed is heterozygous for the translocation.

[201] The method of any one of [196] to [199], wherein a dark blue seed indicates that the seed is homozygous for the translocation.

[202] The method of any one of [187] to [201], wherein the male fertility gene mutation is a gene deletion, a gene knockdown, or a gene knockout.

[203] The method of any one of [187] to [202], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[204] A cereal plant or part thereof produced by the method of any one of [187] to [203].

[205] A seed produced by the method of any one of [187] to [203].

[206] A method for manufacturing a cereal plant line homozygous for a male fertility gene mutation comprising at least one rearranged and/or homoeologous alien addition chromosome, the method comprising: a) crossing a cereal plant comprising at least one rearranged and/or homoeologous alien addition chromosome with a cereal plant nullosomic for said genome to which the rearranged and/or homoeologous chrosomome relates genetically; b) harvesting and selecting seeds comprising the alien chromosome and generating a plant from said seeds; c) crossing the plant of b) with a cereal plant; d) harvesting and selecting seeds comprising the alien chromosome and not comprising any monosomic chromosome, preferably by use of qPCR and/or flow cytometry, and generating a plant from said seeds; e) optionally, backcrossing the plant of d) with a cereal plant, and harvesting and selecting seeds comprising the alien chromosome from said cross(es); f) crossing the plant of d) or e) with a cereal plant homozygous for a male fertility gene mutation; g) harvesting and selecting seeds seeds comprising the alien chromosome and generating a plant from said seeds; h) selfing the plant of g), harvesting and selecting seeds comprising the alien chromosome; i) generating plants from the seeds of h) and selecting a cereal plant homozygous for a male fertility gene mutation which comprises the at least one rearranged and/or homoeologous alien addition chromosome.

[207] The method of [206], wherein the method comprises further j) selfing the plant selected in step i) for obtaining: I) a cereal plant homozygous for a male fertility gene mutation which comprises the at least one rearranged and/or homoeologous alien addition chromosome heterozygously, II) a cereal plant homozygous for a male fertility gene mutation which comprises the at least one rearranged and/or homoeologous alien addition chromosome homozygously, and/or III) a cereal plant homozygous for a male fertility gene mutation which does not comprise the at least one rearranged and/or homoeologous alien addition chromosome.

[208] The method of [206], wherein the at least one rearranged and/or homoeologous alien addition chromosome comprises or is a monosomic alien addition chromosome carrying a male fertility restorer gene and at least one selection marker gene, wherein the male fertility restorer gene and the at least one selection marker gene are on the same side of the centromere of the monosomic alien addition chromosome.

[209] The method of [206], wherein the at least one rearranged and/or homoeologous alien addition chromosome is translocated to at least one homoeologous chromosome pair, wherein the pair consisting of a first and second chromosome, the first chromosome is native to the cereal plant and the second chromosome comprises the alien chromosome or fragment thereof comprising a dominant male fertility restorer gene and at least one selection marker gene.

[210] The method of [208] or [209], wherein the male fertility restorer gene is a dominant gene.

[211] The method of any one of [206] to [210], wherein the cereal plant is a tetraploid wheat, a hexaploid wheat, triticale, maize, rice, barley, or oats.

[212] The method of any one of [206] to [211], wherein the cereal plant is a *Triticum durum* or *Triticum aestivum*.

[213] The method of any one of [206] to [212], wherein the male fertility restorer gene is from *Triticum boeoticum* or *Triticum monococcum*.

[214] The method of any one of [206] to [213], wherein the male fertility restorer gene comprises a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[215] The method of any one of [206] to [214], wherein the selection marker gene is selected from the group consisting of a color marker gene, a plant height gene, or a texture gene.

[216] The method of [215], wherein the color marker gene is able to confer a characteristic coloration of a progeny seed comprising the color marker gene.

[217] The method of [216], wherein the color marker gene is a blue aleurone gene.

[218] The method of [217], wherein the blue aleurone gene is from *Agropyron elongatum, Agropyron trichophorum*, or *Triticum monococcum*.

[219] The method of [217] or [218], wherein the blue aleurone gene comprises a nucleic acid sequence selected from the group consisting of: (i) a nucleic acid sequence having a coding sequence of SEQ ID NO: 44 or 12, or fragments or variants thereof that produce functional amino acid sequences; (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; (iii) a nucleic acid sequence encoding an amino acid sequence of SEQ ID NO: 45 or 13, or fragments or variants thereof that produce functional amino acid sequences; (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

[220] The method of [206] or [207], wherein the male fertility gene mutation is a gene deletion, a gene knockdown, or a gene knockout.

[221] The method of [206], [207] or [220], wherein the male fertility gene is Ms1 or a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

[222] The method of [206], wherein the cereal plant of step a) comprises one additional chromosome to its euploid number of chromosomes, wherein the dominant male fertility restorer gene and at least one selection marker gene are on the additional chromosome.

[223] The method of [208] or [209], wherein the male fertility restorer gene is located in a similar location on the alien addition chromosome as the mutated male fertility gene of the cereal plant.

[224] The method of [209], wherein the first chromosome comprises a piece of chromatin of *Agropyron elongatum* as translocation, preferably onto the end of the long arm of the first chromosome, whereby said piece of chromatin pairs to the alien chromosome fragment or a part thereof.

[225] The method of [209] or [224], wherein the second chromosome further comprises native DNA.

[226] The method of [209], wherein the male fertility restorer gene and selection marker gene are on the opposite sides of the centromere.

[227] The method of [209], wherein the male fertility restorer gene and selection marker gene are on the same side of the centromere.

[228] The method of [209], wherein the first chromosome is 4A, 4B, 4D, or 5A.

[229] The method of [209], wherein the first chromosome is not 4B.

[230] A cereal plant or part thereof produced by the method of any one of [206] to [229].

[231] A seed produced by the method of any one of [206] to [229].

One advantage of the disclosed segregation systems is to allow for a more robust and accurate method for selecting the male-sterile and/or male-fertile cereal plants and/or seeds. The methods and cereal plant lines disclosed herein carrying the selection marker gene associated with the male fertility restorer gene on the same side of centromere has an improved reduced yield loss.

These and other objects, features and advantages of the present invention will become more apparent upon reading the following specification in conjunction with the accompanying description and claims.

BRIEF DESCRIPTION OF THE DRAWINGS

FIGS. 1A-1B demonstrates the basics for the BLA system. FIG. 1A: shows an alien addition chromosome containing chromatin from *T. boeticum* (Bo) with the dominant fertility restorer gene and the *Agropyron elongatum* (Ag) chromatin with the blue color gene (BLA); FIG. 1B: shows the chromosomal make up of normal, sterile and hybrid wheat according to the 42+1 chromosome system. "4B": chromosome 4 of genome B in wheat; "L'": long arm of the chromosome; "S": short arm of the chromosome. FIG. 1C: shows an alien addition chromosome containing chromatin from *T. boeticum* (Bo) with the dominant fertility restorer gene and the *Agropyron elongatum* (Ag) chromatin with the blue color gene (BLA); additionally, this alien addition chromosome contains chromatin of *Triticum aestivum* on the long arm of the chromosome.

FIG. 4 shows how homoeologous recombination of the alien addition chromosome can occur. "4A": chromosome 4 of genome A; "4B": chromosome 4 of genome B; "4C": chromosome 4 of genome C; "5A": chromosome 5 of genome A; "L'": long arm of the chromosome.

FIG. 5 shows the gametocidal (Gc) gene approach to the improved BLA system, including the potential results from the cross of a wheat line carrying an alien addition chromosome (B) with weak gametocidal wheat line and steps to arrive at rearranged line. ' ': disomic appearance of a chromosome, ': monosomic appearance of a chromosome, ms: male sterility due to absence of male fertility locus 'e.g. 'Probus' deletion), MS: male fertility locus is present; 2CC: gametocidal gene located on chromosome 2C).

FIG. 6 shows the irradiation induced rearrangement of monosomic chromosome approach to the improved BLA system, including the potential results from the cross of a wheat line carrying the alien addition chromosome (B) with different strengths of irradiation (175, 200, 225 and 250 Gy) to produce M0 seeds.

FIG. 7 shows the two step homoeologous pairing approach to the improved BLA system, including potential results from the cross of a wheat line carrying an alien addition chromosome (B) with a wheat line carrying homozygous mutation of the homoeologous pairing (ph) gene.

FIG. 9 shows results from Fluorescence In Situ Hybridization (FISH) chromosome scanning of Blue-aleurone (Bla) parental lines, ph1b-mutant lines, lines derived from original crosses between Bla-lines and ph1b-mutant lines.

FIG. 11 shows in A Fluorescence In Situ Hybridization (FISH) photo of line 149-4-3. 42 chromosomes can be identified (20"+T4BS.4BL-4AgL'+BoAg'). The star indicates an alien chromosome. The arrowhead indicates a translocation of the Bla-chromosome onto chromatin from wheat chromosome 4BS. In B Fluorescence In Situ Hybridization (FISH) photo of another tested line with translocation T4DS-4BoS.4BoL-4AgL' is presented.

FIG. 14A: by screening these markers together with the fertility restorer marker and the blue gene marker in the new translocation lines (see also Table 1), assignment of these markers to different genomic regions in the wheat genome is possible; FIG. 14B: gel chromatography of amplificated product of Rf marker (see table 1) for different wheat lines. The top band of double bands at ~1 kb is from the restorer; lines without restorer showed a single band <1 kb.

FIG. 15A shows Fluorescence In Situ Hybridization (FISH) photo of line comprising additionally the translocation of small *Agropyron* segment onto wheat (T4B-4AgL'). Fertility gene is present on normal 4BS wheat arm, being crossed to a blue line to force pairing with Bla-chromosome. FIG. 15B shows Fluorescence In Situ Hybridization (FISH) photo of line comprising the translocation onto wheat (42 chromosome system). The star with the arrow indicates a translocation of the Bla-chromosome onto chromatin from wheat chromosome 4DS. Segregation of 3 blue:1 white has been confirmed.

FIG. 16A-C shows transfer of a new translocation chromosome into 42-chromosome background via crossing with nullisomic tetrasomic lines, exemplified on 4AgL(blue)-4BoL.4BoS(fertility restorer)-4DS (denoted D*). (a) first cross between translocation line and nullisomic tetrasomic Chinese spring; (b) two different gametes from female with or without translocation chromosome; (c) select blue seed and cross with normal wheat; (d) four different female gametes, two combinations result in blue seed; (e) select blue seed for crossing with normal wheat, use qPCR to eliminate lines with extra A chromosome; (f) backcross to normal (elite) wheat line; (g) cross BC1F1 line onto male sterile wheat comprising homozygously the ms1 deletion mutation; (h) select blue seed; (i) plant blue seed and select AAB$^s$B$^s$DD* with KASP markers; (j) system in place segregating 1:2:1 (double blue:single blue:white): white seed can be used for hybrid testcross production, single blue seed can be used for generating more white seed or for pool development, and double blue seed can be discarded.

SEQUENCES

Figure 2:
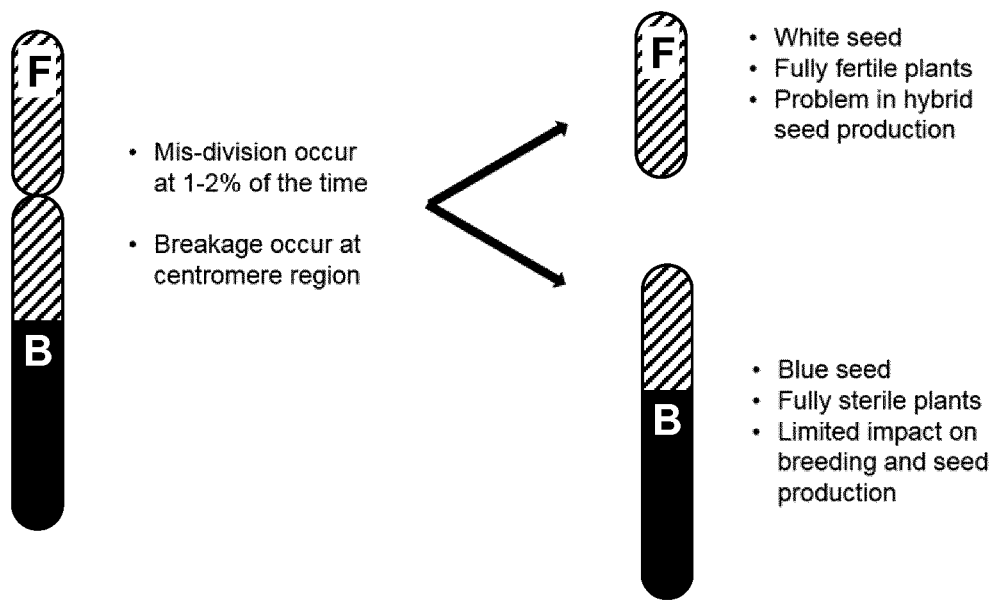
FIG. 2 shows how mis-division of an alien addition chromosome can occur.
Figure 3:
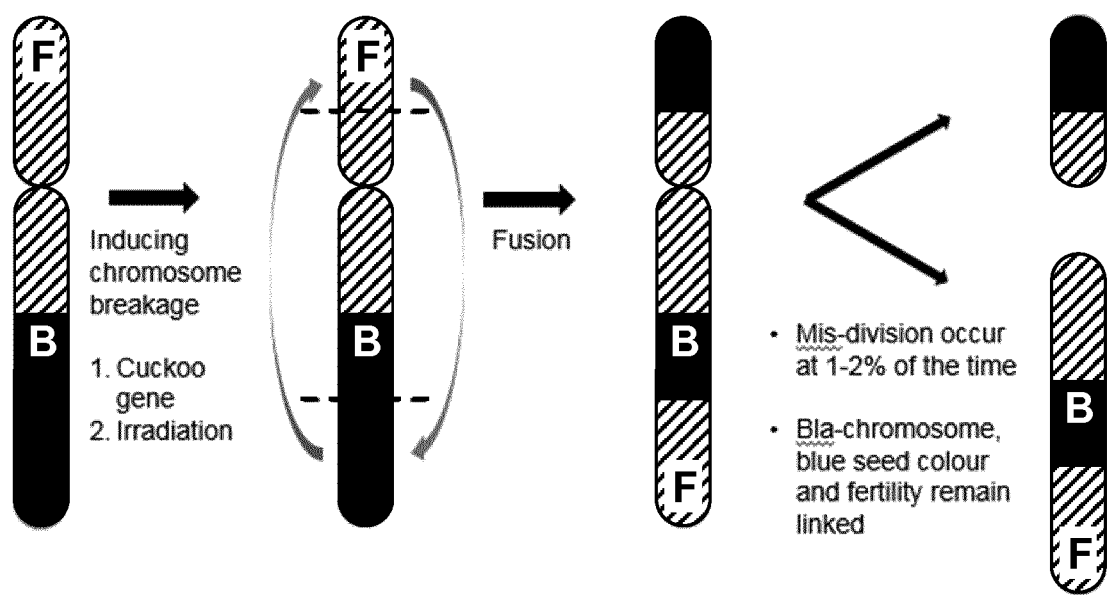
FIG. 3 shows how rearrangement of a monosomic chromosome can occur. Cuckoo genes are also known as gametocidal (Gc) genes.

SEQ ID NO: 1: genomic DNA of *Hordeum vulgare* Ms1 gene
SEQ ID NO: 2: cDNA of *Hordeum vulgare* Ms1 gene
SEQ ID NO: 3: *Hordeum vulgare* Ms1 protein SEQ ID NO: 4: cDNA of *Triticum aestivum* Ms1 gene
SEQ ID NO: 5: *Triticum aestivum* Ms1 protein
SEQ ID NO: 6: genomic DNA of *Triticum aestivum* Ms1 gene
SEQ ID NO: 7: DNA of synthetic Ms1
SEQ ID NO: 8: genomic DNA of *Oryza sativa* Ms1 gene
SEQ ID NO: 9: cDNA of *Oryza sativa* Ms1 gene
SEQ ID NO: 10: genomic DNA of *Brachypodium distachyon* Ms1 gene
SEQ ID NO: 11: cDNA of *Brachypodium distachyon* Ms1 gene
SEQ ID NO: 12: cDNA of *Thinopyrum ponticum* MYC4E (candidate Blue aleurone 1 gene controlling the associated trait in *Triticum aestivum*)
SEQ ID NO: 13: *Thinopyrum ponticum* MYC4E protein
SEQ ID NO: 14: cDNA of *Triticum boeoticum* Ms1 gene
SEQ ID NO: 15: *Triticum boeoticum* Ms1 protein
SEQ ID NOs: 16-41: Marker according to Table 1
SEQ ID NO: 42: *Oryza sativa* Ms1 protein
SEQ ID NO: 43: *Brachypodium distachyon* Ms1 protein
SEQ ID NO: 44: cDNA of *Thinopyrum ponticum* MYC (variant of Blue aleurone gene)
SEQ ID NO: 45: *Thinopyrum ponticum* MYC protein

DETAILED DESCRIPTION OF THE INVENTION

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention be limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a", "an", and "the" include plural references unless the context clearly dictates otherwise. For example, reference to a component is intended also to include composition of a plurality of components. References to a composition containing "a" constituent is intended to include other constituents in addition to the one named. In other words, the terms "a", "an", and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first", "second", and the like, "primary", "secondary", and the like, do not denote any order, quantity, or importance, but rather are used to distinguish one element from another.

It is noted that terms like "specifically", "preferably", "typically", "generally", and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds.

(1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Definitions

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine.

As used herein, "nucleotide" can generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example and not limitation, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide may be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides may include but are not limited to fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethyl-aminophenylazo) benzoic acid (DABCYL), Cascade Blue, Oregon Green, Tex. Red, Cyanine and 5-(2'-aminoethyl) aminonaphthalene-1-sulfonic acid (EDANS).

As used herein, "alien addition chromosome" can refer to a chromosome that is not native to the cereal plant in that it derived from a non-native chromosome (i.e., from a wholly different plant or different plant species, or from a wild relative of the ceral plant species) or at least a portion of the alien addition chromosome is derived from a non-native nucleic acid (e.g., at least the selection marker gene). With respect to the methods and cereal plants disclosed herein, the alien addition chromosome confers fertility to the cereal plant as it carries the male fertility restorer gene. Also, the alien addition chromosome confers a measurable phenotypic characteristic as it carriers a selection marker gene. In certain embodiments, the alien addition chromosome is monosomic, which results in a cereal plant with an odd number of chromosomes. In certain embodiments, the alien addition chromosome is translocated into the genome of the cereal plant, which can result in a cereal plant with an even number of chromosomes. In certain embodiments, the alien addition chromosome is disomic, which results in a cereal plant with an even number of chromosomes. In certain embodiments, the male fertility restorer gene of the alien species is located in a similar location as the male fertility gene of the cereal plant.

As used herein, the term "alien chromosome fragment" can refer to a portion of a chromosome that is derived from a non-native nucleic acid (e.g., at least the selection marker gene) or a native nucleic acid that is integrated into the genome in a location other than its natural location. With respect to the methods and cereal plants disclosed herein, the alien chromosome fragment confers fertility to the cereal plant as it carries the male fertility restorer gene. Also, the alien chromosome fragment confers a measurable phenotypic characteristic as it carriers a selection marker gene. In certain embodiments, the alien chromosome fragment is part of a homoeologous chromosome pair within the genome of the cereal plant.

As used herein, "non-native" can refer to a nucleic acid or polypeptide sequence that is not found in a native nucleic acid or protein of the subject cereal plant. Non-native can refer to a naturally occurring nucleic acid or polypeptide sequence that comprises mutations, insertions and/or deletions. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide.

As used herein, "sequence identity" or "identity" in the context of nucleic acid or polypeptide sequences refers to the nucleic acid bases or amino acid residues in two sequences that are the same when aligned for maximum correspondence over a specified comparison window.

As used herein, the term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, 91%, 92%, 93%, 94%, 95%, 96%, 97%, 98%, or 99% or any integer percentage from 50% to 100%.

As used herein, the term "cereal plant" or "cereal plant line" refers to cereal plant lines, whole plants, plant organs, plant tissues, seeds, plant cells, seeds and progeny of the same. Cereal plant cells include, but are not limited to, cells from seeds, embryos, zygotes, sporophytes, pollen, microspores, suspension cultures, meristematic regions, callus tissue, leaves, roots, shoots, gametophytes, protoplasts, and plastids. Cereal plant parts include differentiated and non-differentiated tissues including, without limitation to, roots, stems, shoots, leaves, pollen, seeds, flowers, consumables (e.g., cereal grains), tumor tissue, plant cells, and plant cell cultures. Cereal plant tissue encompasses plant cells and may be in a plant or in a plant organ, tissue or cell culture. Cereal plant tissue also refers to any clone of such a plant, seed, progeny, propagule whether generated sexually or asexually, and descendants of any of these, such as cuttings or seed. Cereal plant organ refers to plant tissue or a group of tissues that constitute a morphologically and functionally distinct part of a plant.

The term "genome" refers to the entire complement of genetic material (genes and non-coding sequences) that is present in each cell of an organism, or virus or organelle. "Progeny" comprises any subsequent generation of a plant.

As used herein, the terms "crossed" or "cross" or "crossing" means the fusion of gametes via pollination to produce progeny (i.e., cells, seeds, or plants). The term encompasses both sexual crosses (the pollination of one plant by another) and self-fertilization (selfing, self-pollination, i.e., when the pollen and ovule (or microspores and megaspores) are from the same plant or genetically identical plants).

As used herein, the term "hybrid plant" or "hybrid cereal plant" refers to a first generation of offspring derived from a cross between two genetically different parents. In certain embodiments, hybrid plant or hybrid cereal plant includes all first generation progeny, defined as the F1 or filial generation, developed from a cross between two individual plants with different genotypes.

As used herein, the term "transgenic plant", and "transgenic cereal plant" includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a "fertile plant" is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization.

As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female-fertile (but male-sterile) plant can produce viable progeny when crossed with a male fertile plant. In certain embodiments, a male-sterile female parent is one in which no viable male can be produced if self-fertilized.

As used herein, the term "euploid" refers a normal complement of chromosomes. In certain embodiments, euploid refers to the number of chromosomes occurring in the wild-type plant.

As used herein, the term "endogenous", "native", "original", or "wild-type" refers to a naturally-occurring nucleic acid or polypeptide/protein. The native nucleic acid or protein may have been physically derived from a particular organism in which it is naturally occurring or may be a synthetically constructed nucleic acid or protein that is identical to the naturally-occurring nucleic acid or protein.

The terms "associated", "associated with", or "in association with" according to the present disclosure are to be construed broadly and, therefore, according to the present invention imply that a nucleic acid or gene is provided in physical association with another nucleic acid or gene, e.g., within the same chromosome, and more preferably, on the same side of the centromere of the same chromosome. In certain embodiments, associated, associated with, and in association with can mean that the nucleic acid or gene is genetically linked and/or in close proximity. As used herein, the term "genetically linked" can refer to two genes located on the same chromosome. In certain embodiments, "genetically linked" can refer to two genes linked in a manner in which no recombination occurs between the two markers/traits. As used herein, the term "close proximity" can mean that two genes are present on the same chromosome arm and are normally transmitted and stayed associated/together.

The terms "genome editing", "gene editing", and "genome engineering" are used interchangeably herein and refer to strategies and techniques for the targeted, specific modification of any genetic information or genome of a living organism (e.g., cereal plant) at at least one position.

As such, the terms comprise gene editing, but also the editing of regions other than gene encoding regions of a genome.

As used herein, the terms "cassette", "plasmid", and "vector" refer to an extra-chromosomal element often carrying genes that are not part of the native genome of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell.

As used herein, the term "expression" refers to the production of a functional end-product (e.g., DNA, gene, mRNA, guide RNA, or a protein) in either precursor or mature form.

Cereal Plants, Male Fertility Genes, and Selection Marker Genes of the Invention This invention relates to materials and methods for creating and maintaining a cereal plant line for the production of a hybrid cereal plant. The hybrid production system disclosed herein results from the production of male-sterile female parents. Male sterility is achieved by possession of a homozygous mutation of the male fertility gene and/or the expression of a gene that actively sterilizes or leads to the production of a protein that acts to sterilize the female parent cereal plant. The methods disclosed herein result in a hybrid production system that is robust and accurately identifies cereal plants and/or seeds that are male-sterile cereal plants (i.e., female line) from those that are male-fertile cereal plants (i.e., maintainer line). The male-sterile female plant can be used to generate new hybrid cereal plants. The male-fertile cereal plants can be self-fertilized to create the next population of seeds.

Prior to the current invention, mis-division and/or breakage of the alien addition chromosome could result in disassociation of the male fertility restorer gene from the selection marker (see FIG. 2) resulting in male-fertile cereal plants and/or seeds that do not express the selection marker gene as well as cereal plants and/or seeds that express the selection marker gene but are actually male-sterile. In certain embodiments, the cereal plant as disclosed herein do not show mis-division of the alien addition chromosome. In certain embodiments, the cereal plant does not show breakage of the alien addition chromosome. In certain embodiments, if mis-division were to occur, it would not result in a false positive/negative result. In certain embodiments, if a cereal plant as disclosed herein undergoes mis-division and/or breakage of the alien addition chromosome, it does not break the association of the male fertility restorer gene and the selection marker gene. Thus, arrangement of the male fertility restorer gene in association with the selection marker gene on the same side of the centromere of the alien addition chromosome in the disclosed cereal plants leads to reduced yield loss. Said arrangement ensures that all plants derived by self fertilizing are true to type. That is, all plants without the selection marker are sterile and all plants with the selection marker are fertile.

Alien Addition Chromosome Containing Cereal Plants

Disclosed herein are cereal plants (which, as discussed above, includes seeds, progeny, or a part thereof of the cereal plant, etc. . . . ) for use in the production of hybrid cereal plants, wherein the male-fertile maintainer cereal plant comprises an alien addition chromosome carrying a male fertility restorer gene (e.g., a dominant male fertility restorer gene) and at least one selection marker gene and wherein the male fertility restorer gene and the at least one selection marker gene are on the same side of the centromere of the alien addition chromosome. For example, the male fertility restorer gene is associated with the at least one selection marker gene on the same side of the centromere of the alien addition chromosome. In certain embodiments, there is one selection marker gene and it is associated with the male fertility restorer gene on the same side of the centromere of the alien addition chromosome. In certain embodiments, there are two, three, four, or five selection marker genes, each of which are associated with the male fertility restorer gene on the same side of the centromere of the alien addition chromosome. In certain embodiments, at least one of the selection marker genes is a color marker gene as described below.

In certain embodiments, the cereal plant comprises homozygously a male fertility gene mutation as described below. In certain embodiments, the cereal plant comprises a gene or gene product that actively sterilizes the native male fertility gene of the cereal plant as described below.

In certain embodiments, the cereal plant comprises one additional chromosome (i.e., monosomic alien addition chromosome) to its euploid number of chromosomes, wherein the dominant male fertility restorer gene and the at least one selection marker gene are on the additional chromosome.

In certain embodiments, the cereal plant comprises at two additional chromosomes, in a pair (i.e., disomatic alien addition chromosome), to its euploid number of chromosomes, wherein the dominant male fertility restorer gene and the at least one selection marker gene are on at least one of the additional chromosomes.

In certain embodiments, the male fertility restorer gene is the same gene as the native male fertility gene of the cereal plant. In certain embodiments, the male fertility restorer gene is orthologous to the native male fertility gene of the cereal plant. In certain embodiments, the male fertility restorer gene is in an orthologous location on the alien addition chromosome as that of the native male fertility gene of the cereal plant (i.e., the male fertility restorer gene is located in the same or similar location on the alien addition chromosome as the native male fertility gene is located in the genome of the cereal plant).

The alien addition chromosome containing cereal plant, can be generated by any of the methods as disclosed herein. For example, an alien addition chromosome containing cereal plant can be generated by rearranging the alien addition chromosome such that the male fertility restorer gene is associated with the selection marker gene on the same side of the centromere of the alien addition chromosome.

Gametocidal (Gc) genes, also known as Cuckoo genes, are known to cause gamete abortion and chromosome breakage. Gc genes were introduced into crops via alien addition chromosomes for breeding purposes. Some of the Gc genes secured their existence in the host by causing selective abortion of gametes that do not carry them; therefore, they are preferentially transmitted to the offspring. In certain embodiments, the alien addition chromosome containing cereal plant as disclosed herein can be generated by the Gc gene approach. In certain embodiments, the Gc gene induces breakage and rearrangement of at least one alien addition chromosome. In certain embodiments, the cereal plant comprises a Gc gene. In certain embodiments, a Gc gene was used to generate the cereal plants, but it was bred out using linked genetic markers of the cereal plant or was not present in the ceral plant. In certain embodiments, the Gc genes are derived from the *Aegilops* genus. In certain embodiments, the Gc gene are derived from different genomes such as, but not limited to, C, S, $S^1$, $S^{sh}$ and $M^g$. See Endo, 2007, *Chromosome Res.* 15(1):67-75, incorporated by reference herein in its entirety for all purposes. In certain embodiments, the Gc gene is a Gc factor located on chromosome $4M^g$ of *Ae. geniculata* (Kynast et al., 2000, *Chromosome Res.* 8:133-139); on chromosome $2C^c$ of *Ae. cylindrica*; on chromosomes 3C of *Ae. caudata* and/or $3C^t$ of *Ae. triuncialis*; on chromosome 2S and/or 4S of *Ae. longissimi*; or Gc2 of *Ae. sharonensis* (Maan 1975, *Crop Sci.* 15:287-292; Endo 1985, *Jpn. J. Genet.* 60: 125-135); see also Endo 2007 supra, each reference is incorporated by reference herein in their entirety for all purposes. In certain embodiments, the Gc gene is a Gc factor located on 4Mg of *Ae. geniculata* or $2C^c$ of *Ae. cylindrica*.

In certain embodiments, the alien addition chromosome containing cereal plant can be generated by the irradiation approach. In certain embodiments, the radiation induces breakage and rearrangement of at least one alien addition chromosome.

In certain embodiments, the monosomic alien addition chromosome containing cereal plant can be generated by the gene editing approach. In certain embodiments, the male fertility restorer gene is integrated onto the alien addition chromosome near the at least one selection marker gene. In certain embodiments, the at least one selection marker gene is integrated into the alien addition chromosome near the male fertility restorer gene. In certain embodiments, nucleases induce rearrangement of the alien addition chromosome so that the male fertility restorer gene and at least one selection marker gene are in association with each other. In certain embodiments, the gene editing approach genetically links the male fertility restorer gene and at least one selection marker gene. In certain embodiments, the gene editing approach puts the male fertility restorer gene and at least one selection marker gene in close proximity to each other.

Homoeologous Chromosome Containing Cereal Plants

Homologous chromosomes contain the same genes in the same order, although they may have different alleles. Homoeologous (i.e., related) chromosomes can have a similar gene content and order, but diverge in repetitive DNA content. Homoeologous pairing is the pairing of related/equivalent chromosomes across different genomes or within the same genome but between chromosomes that usually do not pair.

Disclosed herein are cereal plants (which, as discussed above, includes seeds, progeny, or a part thereof of the cereal plant, etc. . . . ) for use in the production of hybrid cereal plants, wherein the male-fertile maintainer cereal plant comprises at least one homoeologous chromosome pair, the pair consisting of a first and second chromosome, wherein the first chromosome is native to the cereal plant and the second chromosome is an alien addition chromosome or comprises an alien chromosome fragment comprising a male fertility restorer gene (e.g., a dominant male fertility restorer gene) and at least one selection marker gene. In certain embodiments, the second chromosome further comprises native DNA. In certain embodiments, the first chromosome is 4A, 4B, 4D, or 5A. In certain embodiments, the first chromosome is not chromosome 4B. In certain embodiments, chromosome 4B is avoided because this is also where the Probus deletion (i.e. the male fertility gene mutation) is located, which can complicate future breeding.

In certain embodiments, the male fertility restorer gene and the selection marker gene are on different sides of the centromere of the second chromosome of the homoeologous pair. In certain embodiments, the male fertility restorer gene and the selection marker gene are on the same side of the centromere of the second chromosome of the homoeologous pair. For example, the male fertility restorer gene and the selection marker gene can be re-arranged to one side of the additional chromosome and then translocated it into the normal genome of the cereal plant or they can be introduced using genome editing.

Homoeologous pairing is controlled by Ph (homoeologous pairing suppressor) genes. For example, the Ph1 locus is the major regulator of chromosome pairing and recombination in wheat. Ph1 ensures that during meiosis recombination only occurs between pairs of homologous chromosomes and does not occur between chromosomes from the related (homoeologous) sub-genomes. The known mutant wheat line, ph1b, derived from Chinese Spring Wheat allows for homoeologous pairing to occur. In certain embodiments, the cereal plant (which includes seeds, progeny, or a part thereof of the cereal plant, etc. . . . ) disclosed herein comprises a mutated homoeologous pairing suppressor gene. The Chinese Spring ph1b mutant is a non-limiting example of a cereal plant that express mutated homoeologous pairing suppressor genes (WGRC (Wheat Genetics Resource Center) at Kansas State University under the accession number of TA3809). In certain embodiments, homoeologous pairing can occur by expressing genes that inhibit the homoeologous suppressor genes, such as, but not limited to, those from *T. speltoides*.

In certain embodiments, the homoeologous pairing suppressor gene mutation is a gene deletion, a gene knockdown, or a gene knockout. In certain embodiments, the homoeologous pairing suppressor gene mutation is a gene deletion from chromosome 5B or chromosome 3B. In certain embodiments, the deleted homoeologous pairing suppressor gene is ph1b or ph2. In certain embodiments, the mutated homoeologous pairing suppressor gene is ph1b.

In certain embodiments, a homoeologous pairing suppressor gene mutation can be used to generate the cereal plants, and bred out of the cereal plant (i.e., the cereal plant does not comprise a mutated homoeologous pairing suppressor gene).

In certain embodiments, the cereal plant (which, as defined above includes seeds, progeny, or a part thereof of the cereal plant, etc. . . . ) comprises, consists, consists essentially of a euploid number of chromosomes.

In certain embodiments, the cereal plant comprises homozygously a male fertility gene mutation as described below. In certain embodiments, the cereal plant comprises a gene or gene product that actively sterilizes the native male fertility gene of the cereal plant as described below.

Integrated Alien Nucleic Acid Containing Cereal Plants

Disclosed herein are cereal plants (which, as discussed above, includes seeds, progeny, or a part thereof of the cereal plant, etc. . . . ) for use in the production of hybrid cereal plants, wherein the male-fertile maintainer cereal plant comprises a male fertility restorer gene (e.g., a dominant male fertility restorer gene) associated with at least one selection marker gene, wherein they are integrated together into the cereal plant genome. In certain embodiments, the male fertility restorer gene and/or at least one selection marker gene are alien (i.e., non-native) to the cereal plant line.

In certain embodiments, the male fertility restorer gene and the selection marker gene are on the same side of the centromere of chromosome they are integrated into.

Cereal Plants Types

"Cereal plant" as used herein refers to a crop plant of the grass family (i.e., *Graminaceae* or *Poaceae*) cultivated for the food value of their grains, such as, but not limited to, wheat, triticale, corn, rice, barley, oat, rye, sorghum, millet, buckwheat, fonio, and quino. In certain embodiments, the cereal plant is a tetraploid wheat, a hexaploid wheat, triticale, maize, rice, barley, or oats. In certain embodiments, the cereal plant is wheat (e.g., any species of the genus *Triticum*, including progenitors thereof, as well as progeny thereof produced by crosses with other species). In certain embodiments, the cereal plant is a tetraploid wheat or a hexaploid wheat. Hexaploid wheat (e.g., genome organization of AABBDD), comprised of 42 chromosomes, and includes, for example, *T. aestivum, T. spelta, T. mocha, T. compaction, T. sphaerococcum, T. vavilovii*, and interspecies cross thereof. Tetraploid wheat (e.g., genome organization of AABB), comprised of 28 chromosomes, and includes, for example, *T. durum* (also referred to as durum wheat or *Triticum turgidum* ssp. *durum*), *T. dicoccoides, T. dicoccum, T polonicum*, and interspecies cross thereof. Wheat can also include possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. In certain embodiments, the cereal plant is a *Triticum durum* or *Triticum aestivum*.

These methods should work in all species which are self fertilized. Additional plants can be used, including monocot and dicot plants. Examples of monocot plants that can be used include, but are not limited to, sugarcane (*Saccharum* spp.), corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), sugar beet (*Beta vulgaris*), cotton (*Gossypium arboreum*), and peanut (*Arachis hypogaea*), tomato (*Solanum lycopersicum*), potato (*Solanum tuberosum*), etc. Additional monocots that can be used include oil palm (*Elaeis guineensis*), sudangrass (*Sorghum×drummondii*), and rye (*Secale cereale*). Additional dicots that can be used include safflower (*Carthamus tinctorius*), coffee (*Coffea arabica* and *Coffea canephora*), amaranth (*Amaranthus* spp.), and rapeseed (*Brassica napus* and *Brassica napobrassica*; high erucic acid and canola).

Additional non-limiting exemplary plants for use with the invented methods and compositions include *Hordeum vulgare, Hordeum bulbusom, Sorghum bicolor, Saccharum officinarium, Zea mays, Setaria italica, Oryza minuta, Oriza sativa, Oryza australiensis, Oryza alta, Triticum aestivum, Triticum durum, Triticale, Malus domestica, Brachypodium distachyon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica oleracea, Brassica rapa, Raphanus sativus, Brassica juncacea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and *Allium tuberosum*, or any variety or subspecies belonging to one of the aforementioned plants.

Also encompassed are plants that are produced by conventional techniques using *Triticum* sp. as a parent in a sexual cross with a non-*Triticum* species, such as rye (Secale cereal), including but not limited to triticale. In certain embodiments, the cereal plant is a triticale.

Male Fertility Genes

The cereal plants disclosed herein include nucleic acids and peptides that influence male fertility. In certain aspects, the nucleic acids that influence male fertility are male fertility genes that are endogenous or "native" to the cereal plant. In certain embodiments, the male fertility gene is mutated, thus resulting in a male-sterile cereal plant. Mutation of an endogenous gene that results in the suppression of the gene function can result from, for example without limitation, by deleting or inserting one or a few nucleotides into the nucleotide sequence of the gene (e.g., into the promoter, coding sequence, or intron), by substituting one or a few nucleotides in the gene with other different nucleotides, or by knocking out the gene (e.g., by homologous recombination using an appropriate targeting vector). Cereal plants having mutations in both alleles can be obtained, for example without limitation, using crossing methods as known in the art. In certain embodiments, mutation can be a result of gene deletion, gene knockdown, or gene knockout.

In certain embodiments, the male fertility gene is Ms1, including homologs and orthologs of Ms1. In certain embodiments, the male fertility gene comprises, consists of, or consists essentially of a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence as set forth in SEQ ID NO: 3, 5, 15, 42, or 43, or fragments thereof. Additional mutants of Triticum aestivum includes mutants as disclosed in Pugsley's (ms1a): see Pugsley, A. T. and R. N. Oram (1959) *Aust. Pl. Breed. Genet. Newsl.* No. 14:10-11; Suneson, C. A. (1962) *Crop Sci.* 2:534-535; and Waninge, J. and Zeven, A. C. (1968) *Euphytica* 17:378-380; Probus (ms1b): see Fossati, A. and M. Ingold (1970) *Wheat Information Service* (Kyoto) 30:3-10; Cornerstone (ms1c): see Driscoll, C. J. and K. K. Barlow (1976) *Induced Mutation in Cross-Breeding*, IAEA, Vienna, Austria pp. 123-131; see also Endo et al. (1991) *The Japanese Journal of Genetics* 66(3):291-295; Klindworth et al. (2002) *Crop Sci.* 42:1447-1450; Cenci et al. (2003) *Theor. Appl. Genet* 107(5):931-9; U.S. Pat. No. 5,478,369; and US20160201084, each of which are incorporated by reference herein in their entirety for all purposes. Also included are Ms1 mutants ms1d, ms1e, and ms1f, and variations thereof, Klindworth et al. 2002. *Crop Sci.* 42:1447-1450; ET0487, ET0488, ET0489, ET0490, ET0491, ET0495, 007-0033.1, and 007-0046.1 as well as the ms1 mustant disclosed in Tucker et al., Nature Communications 8, Article number: 869 (2017), each of which are incorporated by reference herein in their entirety for all purposes. In certain embodiments, the mutation is the Probus deletion (ms1b).

In certain aspects, male fertility can be removed by the expression of a gene that actively sterilizes or leads to the production of a protein that acts to sterilize the cereal plant; see EP0329308, EP0737749, WO1990/08828, and WO1990/08829, each of which are incorporated by reference herein in their entirety for all purposes. For example, inactivation of an endogenous gene that results in suppression of the gene function also can result by introduction into cells of the plant of a transgene that suppresses expression of the endogenous gene or a product expressed from the endogenous gene (e.g., encoding a polypeptide), or a transgene that encodes a product (e.g., an RNA) that suppresses expression of the endogenous gene or a product encoded by the endogenous gene in cells of the cereal plant in which the gene normally is expressed. In certain embodiments, the sterility gene can be MS26 (see for example U.S. Pat. Nos. 7,098,388; 7,517,975; and 7,612,251), MS45 (see for example U.S. Pat. Nos. 5,478,369 and 6,265,640) or MSCA1 (see for example U.S. Pat. No. 7,919,676). For example, without limitation, inactivation of endogenous fertility genes can be effected by expressing hairpin RNA molecules (hpRNA) in cells of the reproductive organs of a plant (e.g., the filament, anther, tapetum, and pollen); see, e.g., Matzke et al. (2001) *Curr. Opin. Genet. Devel.* 11:221-227; Scheid et al. (2002) *Proc. Natl. Acad. Sci., USA* 99:13659-13662; Waterhouse and Helliwell (2003) *Nature Reviews Genetics* 4:29-38; Aufsaftz et al. (2002) *Proc. Nat'l. Acad. Sci.* 99(4):16499-16506; Sijen et al., (2001) *Curr. Biol.* 11:436-440); Kenn et al (1986) *J. Bacteriol.* 168:595; McLean et al (1987) *J. Bacteriol.* 169:1017 (1987); and U.S. Pat. No. 4,918,006, each of which are incorporated by reference herein in their entirety for all purposes.

Phenotyping of male fertility gene mutants can be conducted using techniques known in the art. For example, one can conduct genetic screening of the cereal plant. One can also use quantitative fertility scoring by, for example, preventing open-pollinated seeds from forming by covering at least three spikes per plant before anthesis (e.g., with paper bags fastened with a paper clip). To determine the quantitative fertility score, the number of florets per spike and the number of seed per spike are counted and expressed as the number of seeds per floret formed.

Also provided herein, are male fertility restorer genes used to restore the fertility of a male-sterile plant. The male fertility restorer gene is selected to be able to compensate for the mutation of the male-fertility gene or to counteract any gene that sterility gene or protein. In certain embodiments, the male fertility restorer genes are recessive. In certain embodiments, the male fertility restorer genes are dominant. The male fertility restorer gene can be a functional version of the male fertility genes disclosed above. In certain embodiments, the male fertility restorer gene is Ms1, including homologs and orthologs of Ms1. In certain embodiments, the male fertility restorer gene comprises, consists of, or consists essentially of a nucleic acid comprising a nucleic acid sequence selected from the group consisting of: (i) a nucleic acid sequence as set forth in SEQ ID NO: 1, 6, 7, 8, or 10, or fragments or variants thereof that produce functional amino acid sequences; (ii) a nucleic acid sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence as set forth in SEQ ID NO: 1, 6, 7, 8, or 10, or fragments thereof that produce functional amino acid sequences; (iii) a nucleic acid sequence having a coding sequence as set forth in SEQ ID NO: 2, 4, 9, 11, or 14, or fragments or variants thereof that produce functional amino acid sequences; (iv) a nucleic acid sequence having a coding sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence as set forth in SEQ ID NO: 2, 4, 9, 11, or 14, or fragments thereof that produce functional amino acid sequences; (v) a nucleic acid sequence encoding an amino acid sequence as set forth in SEQ ID NO: 3, 5, 15, 42, or 43, or fragments or variants thereof that produce functional amino acid sequences; (vi) a nucleic acid sequence encoding an amino acid sequence with at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence as set forth in SEQ ID NO: 3, 5, 15, 42, or 43, or fragments thereof. In certain embodiments, the male fertility restorer gene is from *T. boeoticum* or *T. monococcum, T. thaouder*, or *T. urartu*.

Selection Marker Genes

Also provided herein, are selection marker genes that can be used to identify male-fertile cereal plants and/or seeds. The selection marker gene encodes a scorable or screenable marker. In order to accurately identify the male-fertile plants, the selection marker must be associated with the male-fertility restorer gene. As the methods disclosed herein result in the selection marker gene and the male fertility restorer gene being located on the same side of centromere of the same chromosome, there is a significant reduction of while fertile seeds and plants from blue sterile seeds. This is because there would be reduced chance of a mis-division causing the selection marker gene being separated or disassociated with the male fertility restorer gene (i.e., leading to two telocentric chromosomes with one carrying only the selection marker gene and the other carrying only the male fertility restorer gene). As such, the disclosed methods and cereal plant lines carrying the selection marker gene associated with the male fertility restorer gene on the same side of centromere has an improved reduced yield loss.

For example, but not limitation, the selection marker gene can be a color marker gene (e.g., seed, silks, husks, tassels, flowers, and/or grain), a plant height gene, a texture gene, an aroma gene, microsatellites (e.g., short tandem repeats, STRs, or simple sequence repeats, SSRs), restriction fragment length polymorphism (RFLP), random amplification of polymorphic DNA (RAPD), amplified fragment length polymorphism (AFLP), single nucleotide polymorphisms (SNPs), or a combination thereof.

In certain aspects, the selection marker is a color marker (e.g., visual and/or fluorescent). When the selectable marker is a color marker, it is possible to separate the cereal plants or seeds, depending on how the color phenotype is expressed to determine which plants or seeds possess the male-fertility restorer gene. For examine, if the color marker results in a seed having a specification (e.g., blue aleurone or other an endosperm coloring trait), it is possible to separate the seeds into colored seeds (e.g., blue seeds) from which male-fertile plants (i.e., maintainer line) are developed, and natively colored (e.g., red/white) seeds from which male-sterile plants (i.e., female line). The possibility to sort out the seeds of the male-sterile female line directly from the progeny simplifies the system and reduces to a great extent the production cost of the hybrid seeds. For example, a seed sorter would be able to detect the difference between the native color and seeds expressing the color marker.

In certain embodiments, the color selection marker gene can come from, for example but not limited to, a blue aleurone gene (e.g., from *Agropyron elongatum, Agropyron trichophorum, Triticum thaoudar*, or *Triticum monococcum*).

In certain embodiments, the selection maker can be for example, without limitation, β-glucuronidase; uidA gene (GUS) (encoding an enzyme for which various chromogenic substrates are known (e.g., U.S. Pat. Nos. 5,268,463 and 5,599,670)); chloramphenicol acetyl transferase; alkaline phosphatase; anthocyanin/flavonoid polynucleotides (e.g., an R-locus polynucleotide (encoding a product that regulates the production of anthocyanin pigments (red color) in plant tissues); genes controlling biosynthesis of flavonoid pigments (e.g., maize C1 and C2, the B gene, the p1 gene, and the bronze locus genes); cyan fluorescent protein (CYP) gene; a the yellow fluorescent protein gene (YFP); red fluorescent protein gene (RFP), yellow-green fluorescent protein (mNeonGreen), a lux gene (encoding luciferase); a green fluorescent protein (GFP), and DsRed2 (Clontech Laboratories, Inc., Mountain View, Calif.); p-lactamase gene encoding an enzyme for which various chromogenic substrates are known (e.g., PADAC, a chromogenic cephalosporin); a xylE gene (encoding a catechol dioxygenase that can convert chromogenic catechols); and a tyrosinase gene (encoding an enzyme capable of oxidizing tyrosine to DOPA and dopaquinone, which in turn condenses to form the easily detectable compound melanin). Also included are any selection markers the presence of which may be detected using, for example, X-ray film, scintillation counting, fluorescent spectrophotometry, low-light video cameras, photon counting detectors (e.g., cameras), and/or multiwell luminometry.

Additional markers can be found at Yarranton, Curr Opin Biotech (1992) 3:506-11; Christopherson et al., Proc. Natl. Acad. Sci. USA (1992) 89:6314-8; Yao et al., Cell (1992) 71:63-72; Reznikoff, Mol Microbiol (1992) 6:2419-22; Hu et al., Cell (1987) 48:555-66; Brown et al., Cell (1987) 49:603-12; Figge et al., Cell (1988) 52:713-22; Deuschle et al., Proc. Natl. Acad. Sci. USA (1989) 86:5400-4; Fuerst et al., Proc. Natl. Acad. Sci. USA (1989) 86:2549-53; Deuschle et al., Science (1990) 248:480-3; Gossen, Ph.D. Thesis, University of Heidelberg (1993); Reines et al., Proc. Natl. Acad. Sci. USA (1993) 90:1917-21; Labow et al., Mol Cell Biol (1990) 10:3343-56; Zambretti et al., Proc. Natl. Acad. Sci. USA (1992) 89:3952-6; Bairn et al., Proc. Natl. Acad. Sci. USA (1991) 88:5072-6; Wyborski et al., Nucleic Acids Res (1991) 19:4647-53; Hillen and Wissman, Topics Mol Struc Biol (1989) 10:143-62; Degenkolb et al., Antimicrob Agents Chemother (1991) 35:1591-5; Kleinschnidt et al., Biochemistry (1988) 27:1094-104; Bonin, Ph.D. Thesis, University of Heidelberg (1993); Gossen et al., Proc. Natl. Acad. Sci. USA (1992) 89:5547-51; Oliva et al., Antimicrob Agents Chemother (1992) 36:913-9; Hlavka et al., Handbook of Experimental Pharmacology (1985), Vol. 78 (Springer-Verlag, Berlin); Gill et al., Nature (1988) 334:721-4; all of which are incorporated by reference herein in their entirety for all intended purposes.

Methods for Creating and Maintaining a Cereal Plant Line for the Production of a Hybrid Cereal Plant This invention relates to materials and methods for creating and maintaining a cereal plant line for the production of a hybrid cereal plant. The hybrid production system disclosed herein results from the production of male-sterile female parents. Male sterility is achieved by possession of a homozygous mutation of the male fertility gene and/or the expression of a gene that actively sterilizes or leads to the production of a protein that acts to sterilize the female parent cereal plant. The methods disclosed herein result in a hybrid production system that is robust and accurately identifies cereal plants and/or seeds that are male-sterile cereal plants (i.e., female line) from those that are male-fertile cereal plants (i.e., maintainer line). The male-sterile female plant can be used to generate new hybrid cereal plants. The male-fertile cereal plants can be self-fertilized to create the next population of seeds (i.e., maintain the cereal plant line).

Embodiments of the present invention relate generally to methods and materials for improving the current 42+1 chromosome system, including for example and not limitation, rearrangement or translocation of the alien addition chromosome. In certain embodiments, the system utilizes a male fertility restorer gene and a selection marker (e.g., color marker) for ease of detection. The rearrangement of an alien addition chromosome within itself could be achieved by gametocidal (Gc) genes, irradiation, and/or gene editing. Translocation of an alien chromosome fragment could be achieved by homoeologous pairing (e.g., ph1b assisted) and/or gene editing.

Gametocidal (Gc) Genes Approach

In certain embodiments, according to the various aspects of the present invention, the method can entail introducing a gametocidal (Gc) gene into a cereal plant line comprising an alien addition chromosome carrying a male fertility restorer gene and at least one selection marker gene on different sides of the centromere to induce rearrangement of the alien addition chromosome such that the male fertility restorer gene and at least one selection marker gene on the same side of the centromere. See e.g., FIG. 5. In certain embodiments, the methods entail: a) selecting a cereal plant line homozygous for a male fertility gene mutation (as described above) comprising at least one alien addition chromosome carrying a male fertility restorer gene and at least one selection marker gene on different sides of the centromere of the at least one alien addition chromosome; b) rearranging the at least one alien addition chromosome; and c) obtaining a cereal plant comprising a rearranged alien addition chromosome. The male fertility, male fertility restorer, and the at least one selection marker genes are described in more detail above.

In certain embodiments, the rearranging step b) results from the presence of at least one Gc gene. Examples of applicable Gc genes are disclosed in greater detail above. The Gc gene induces breakage and rearrangement of the at least one alien addition chromosome. The breakage and rearrangement results in the male fertility restorer gene and the at least one selection marker gene being in association with each other and on the same side of the centromere of the at least one alien addition chromosome.

The Gc gene can be introduced as a monosomic addition chromosome. In certain embodiments, the Gc gene is bred out of the cereal plant line. This can occur by discarding seeds that express the Gc gene. For example, the Gc gene can be detected directly by molecular and/or cytogenetic techniques generally known to those of skill in the art. The Gc gene can also be detected by identifying unmarked (e.g., white) seeds that contain 43 chromosomes (i.e., the Gc gene is on an alien addition chromosome; see FIG. 5). The Gc gene can also be detected by identifying seeds and/or plants marked for selection (e.g., blue colored seeds in the case of the blue aleurone gene) that contain 44 chromosomes (i.e., the seed contains two alien addition chromosomes: one comprising the Gc gene and the other comprising the male fertility restorer gene and selection marker gene; see FIG. 5).

In certain embodiments, the Gc gene is already present in the genome of the cereal plant and optionally mutated once rearrangement of the alien addition chromosome has occurred.

In certain embodiments, the alien addition chromosome is monosomic. In certain embodiments, the alien addition chromosome is disomic.

By way of example, and not limitation, the Gc gene approach for the production of a hybrid cereal plant can be achieved by (see also as outlined in Example 1; FIG. 5):

Step a): crossing a first cereal plant comprising at least one alien addition chromosome carrying a dominant male fertility restorer gene and at least one selection marker gene on different sides of the centromere of the at least one alien addition chromosome and a homozygous male fertility gene mutation with a second cereal plant comprising at least one gametocidal addition chromosome carrying a gametocidal gene, preferably two addition chromosomes carrying a gametocidal gene. This first cross introduces the Gc gene into a cereal plant line carrying the alien addition chromosomes. In certain embodiments, the alien addition chromosome is monosomic. In certain embodiments, the gametocidal addition chromosome is disomic. In certain embodiments, the gametocidal addition chromosome is monosomic. In certain embodiments, the first cereal plant expresses a fertility suppressor gene rather than homozygous male fertility gene mutation and the male fertility restorer gene is able to block the effects of the fertility suppressor gene.

Step b): harvesting, selecting, and planting at least one seed produced by step a) expressing the selection marker gene, wherein the seed comprises the at least one alien addition chromosome and a monosomic gametocidal addition chromosome to produce a third cereal plant. The third cereal plant comprises a heterozygous male fertility gene mutation and a single copy of the Gc chromosome or no Gc chromsome. For example, seeds and/or cereal plants resulting from the cross that do not express the selection marker are discarded while seeds and/or cereal plants expressing the selection marker are kept for further crossing.

Step c): crossing the third cereal plant produced in step b) with the first cereal plant of step a). In this step, both parents express the alien addition chromosome. The first cereal plant is used to maintain the msms status.

Step d): harvesting, selecting, and planting at least one seed produced in step c) expressing the selection marker gene, wherein the seed comprises the monosomic alien addition chromosome (i.e., a total of 43 chromosomes) and homozygous male fertility gene mutation to generate a progeny cereal plant of the first filial generation comprising a homozygous male fertility gene mutation. The molecular marker can be used to select the homozygous msms and get rid of the Msms type.

Step e): self-fertilizing the progeny cereal plant of the first filial generation produced in step d);

Step f): harvesting, selecting, and planting at least one seed produced in step e) expressing the selection marker gene, wherein the seed comprises the monosomic alien addition chromosome and homozygous male fertility gene mutation to generate a progeny cereal plant of the second filial generation. Seeds and/or cereal plant expressing the selection marker are kept while those not expressing the selection marker are discarded.

Step g): self-fertilizing the progeny cereal plant of the second filial generation produced in step f).

Step h): optionally repeating steps f) and g) for at least one additional generation.

Step i): harvesting seeds of the third filial generation produced in step g) or h), if step h) is performed.

Step j): selecting and planting at least one seed of the third filial generation not expressing the selection marker gene to generate a progeny cereal plant of the fourth filial generation. In certain embodiments, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 seeds are selected and planted.

Step k): phenotyping the ears of the cereal plant of the fourth filial generation produced in step j). When planting all seeds not expressing the selection marker not showing fertile ears could have a rearranged alien addition chromosome and corresponding seeds expressing the selection marker can be checked cytologically to confirm if favorable rearrangement has happened.

Step l): selecting a population of cereal plants of the fourth filial generation showing complete sterility in step k) to generate a cereal plant for the production of a hybrid cereal plant. The selection process can be made based on the expression of the at least one selection marker gene. Any population without complete sterility is discarded. In certain embodiments, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 seeds are selected and planted.

Specific markers for the male fertility restorer gene and/or the at least one selection marker gene can be used for confirmation of the rearrangement.

In certain embodiments, the methods entail selecting and crossing at least one hybrid cereal plant comprising the rearranged monosomic alien addition chromosome with a cereal plant not treated by one of the methods disclosed herein to reduce in a progeny any unwanted chromosomal rearrangement or mutations introduced into the cereal plant genome.

In certain embodiments, cereal lines with a rearranged alien addition chromosome can be backcrossed with an elite cereal line. In certain embodiments, backcrossing with elite cereal lines eliminates any other unintentional chromosome mutation and/or rearrangement in the native cereal plant genome. For example, the elite cereal lines can effectively replace any unintentionally mutated and/or rearranged genomic regions in the cereal plant expressing the Gc gene with well-developed genetic material. In certain embodiments, the elite cereal line is an adapted cereal line. In certain embodiments, the elite cereal line is a nationally listed variety.

In certain embodiments, the methods comprise examining at least one selection marker gene expressing seed from the population to confirm the seed comprises a rearranged monosomic alien addition chromosome, which comprises the dominant male fertility restorer gene and the selection marker gene on the same side of the centromere of the rearranged monosomic alien addition chromosome. In certain embodiments, the examining step comprises conducting a cytological analysis or molecular analysis. In certain embodiments, the examining step comprises conducting FISH (fluorescence in-situ hybridization) or GISH (genomic in-situ hybridization) microscopy to detect the location of translocation.

In certain embodiments, the cereal plant, which as defined above includes at least a seed, progeny, or a part thereof, does not comprise a mis-division of the alien addition chromosome. In certain embodiments, the cereal plant does not comprise a breakage of the alien addition chromosome. In certain embodiments, the cereal plant does not comprise i) a mis-division of the alien addition chromosome nor ii) a breakage of the alien addition chromosome.

Irradiation Approach

In certain embodiments, according to the various aspects of the present invention, the method can entail irradiating a male-sterile female plant comprising an alien addition chromosome carrying a male fertility restorer gene and at least one selection marker gene on different sides of the centromere and testing for the rearrangement of the alien addition chromosome such that the male fertility restorer gene and the at least one selection marker gene on the same side of the centromere. See e.g., FIG. 6. In certain embodiments, the methods entail: a) selecting a cereal plant line homozygous for a male fertility gene mutation (as described above) comprising at least one alien addition chromosome carrying a male fertility restorer gene and at least one selection marker gene on different sides of the centromere of the at least one alien addition chromosome; b) rearranging the at least one alien addition chromosome; and c) obtaining a cereal plant comprising a rearranged alien addition chromosome. The male fertility, male fertility restorer, and the at least one selection marker genes are described in more detail above.

In certain embodiments, the rearranging step b) results from irradiating seeds of the cereal plant line of step a). In certain embodiments, irradiating seeds induces chromosomal rearrangement of at least one alien addition chromosome.

Radiation treatment can occur at any stage of development of the seed. In certain embodiments, the ungerminated seeds are irradiated.

Radiation treatment for chromosome breakage and rearrangement can include, but are not limited to X-rays, fast neutrons, gamma rays, ultraviolet, mixed high-energy particles, and ion beams. The choice of radiation treatment can be related to the type of materials to be treated and the expected/desired frequency and spectrum of mutations. Fast neutrons can induce relatively small segment deletions or translocations. X-rays and gamma rays allow for good penetration, high reproducibility, high translocation frequency, and/or fewer disposal (radioactive waste) problems.

X-ray induced mutagenesis requires rotation of the sample in the X-ray beam. In certain embodiments, the seeds are placed in a canister which orbits the X-ray source. In certain embodiments, the canister is rotated longitudinally along the axis. The type of energy emitted is commonly 50-300 keV. The X-ray penetrates the plant tissue a few mm to many cm.

Gamma-ray induced mutagenesis is generate by radioisotopes. The type of energy emitted is up to several MeV. The gamma-rays can penetrate all the way through the plant.

Neutron energy comes in fast, slow, and thermal and generated by nuclear reactors or accelerators. The type of energy emitted is from less than 1 eV to several MeV. Neutrons can penetrate into the plant tissue by many cm.

In certain embodiments, the seeds are irradiated with radiation energy from about 100 Gy to about 500 Gy. In certain embodiments, the seeds are irradiated with radiation energy from about 150 Gy to about 400 Gy. In certain embodiments, the seeds are irradiated with radiation energy from about 175 Gy to about 250 Gy. In certain embodiments, the seeds are irradiated with radiation energy from about 200 Gy to about 250 Gy. In certain embodiments, the seeds are irradiated with radiation energy from about 200 Gy to about 225 Gy. In certain embodiments, the seeds are irradiated with at least about 100 Gy, at least about 110 Gy, at least about 120 Gy, at least about 125 Gy, at least about 130 Gy, at least about 140 Gy, at least about 150 Gy, at least about 160 Gy, at least about 170 Gy, at least about 175 Gy, at least about 180 Gy, at least about 190 Gy, at least about 200 Gy, at least about 210 Gy, at least about 220 Gy, at least about 225 Gy, at least about 230 Gy, at least about 240 Gy, at least about 250 Gy, at least about 260 Gy, at least about 270 Gy, at least about 275 Gy, at least about 280 Gy, at least about 290 Gy, at least about 300 Gy. In certain embodiments, the seeds are irradiated with 175, 200, 225, or 250 Gy.

In certain embodiments, the seeds are irradiated from about 20 to about 90 minutes. In certain embodiments, the seeds are irradiated from about 25 to about 85 minutes, about 30 to about 80 minutes, about 35 to about 75 minutes, about 40 to about 70 minutes, about 41 to about 65 minutes, about 42 to about 60 minutes, about 43 to about 59 minutes, about 44 to about 58 minutes, about 45 to about 57 minutes, about 46 to about 56 minutes, about 47 to about 55 minutes, about 48 to about 54 minutes, about 49 to about 53 minutes, or about 50 to about 52 minutes. In certain embodiments, the seed are irradiated from about 40 to about 50 minutes, about 41 to about 50 minutes, about 42 to about 50 minutes, about 43 to about 50 minutes, about 44 to about 49 minutes, about 45 to about 48 minutes, or about 46 to about 47 minutes.

By way of example, and not limitation, the irradiation approach for the production of a hybrid cereal plant can be achieved by (see also as outlined in Example 2; FIG. 6):

Step a) irradiating at least one seed (as outlined above) comprising an alien addition chromosome carrying a dominant male fertility restorer gene and at least one selection marker gene on different sides of the centromere. In certain embodiments, the alien addition chromosome is monosomic. In certain embodiments, the alien addition chromosome is disomic. This irradiation step allows for the breakage of the alien addition chromosome at different levels. In certain embodiments, at least about 500, at least about 750, at least about 1000, at least about 1250, at least about 1500, at least about 1750, at least about 2000, at least about 2250, at least about 2500, at least about 2750, at least about 3000, at least about 3250, at least about 3500, at least about 3750, at least about 4000, at least about 4250, at least about 4500, at least about 4750, at least about 5000, at least about 5250, at least about 5500, at least about 5750, at least about 6000, at least about 6250, at least about 6500, at least about 6750, at least about 7000, at least about 7250, at least about 7500, at least about 7750, at least about 8000, at least about 8250, at least about 8500, at least about 8750, or at least about 9000 seeds are irradiated.

Step b): planting the at least one seed irradiated in step a) to produce at least one first cereal plant.

Step c): harvesting essentially all the seeds from the at least one first cereal plant produced in step b) to create at least one population of seeds, wherein each population of seeds are from one individual plant and wherein each population of seeds comprise seeds expressing the at least one selection marker gene and seeds not expressing the at least one selection marker gene.

Step d): planting at least one seed not expressing the selection marker gene from the population of step c). This step serves to prove whether the seed comprises an undesired mis-division (i.e., one in which the rearrangement of the male fertility restorer gene to the same side of the centromere as the selection marker gene did not occur). In certain embodiments, essentially all of the seeds of step c) is planted. In certain embodiments, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% of the seeds from step c) are planted. In certain embodiments, at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, or at least about 300 seeds are planted.

Step e): discarding a population of seeds which produce a fertile plant in step d).

Step f): self-fertilizing the seeds expressing the selection marker gene that were not discarded in step e) to create a next population of seeds, wherein each population of seeds are from one individual plant, wherein each population of seeds comprise seeds expressing the at least one selection marker gene and seeds not expressing the at least one selection marker gene. In certain embodiments, the seeds are cytologically examined to determine the chromosome composition of the alien addition chromosome.

Step g): optionally repeating steps d) and e) at least once. In certain embodiments, at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 310, at least about 320, at least about 330, at least about 340, at least about 350, at least about 360, at least about 370, at least about 380, at least about 390, or at least about 400 seeds are planted.

Step h): planting at least one seed not expressing the at least one selection marker.

Step i): selecting a population of seeds from a population of cereal plants showing complete sterility to generate a cereal plant for the production of a hybrid cereal plant.

Specific markers for the male fertility restorer gene and/or the at least one selection marker gene can be used for confirmation of the rearrangement.

In certain embodiments, cereal lines with a rearranged alien addition chromosome can be backcrossed with an elite cereal line as discussed above. In certain embodiments, the methods entail selecting and crossing at least one hybrid cereal plant comprising the rearranged monosomic alien addition chromosome with a cereal plant not treated by one of the methods disclosed herein to reduce in a progeny any unwanted chromosomal rearrangement or mutations introduced into the cereal plant genome.

In certain embodiments, the methods comprise examining at least one selection marker gene expressing seed from the population to confirm the seed comprises a rearranged monosomic alien addition chromosome, which comprises the dominant male fertility restorer gene and the at least one selection marker gene on the same side of the centromere of the rearranged monosomic alien addition chromosome. In certain embodiments, the examining step comprises conducting a cytological analysis or molecular analysis. In certain embodiments, the examining step comprises conducting FISH (fluorescence in-situ hybridization) or GISH (genomic in-situ hybridization) microscopy to detect the location of translocation.

In certain embodiments, the cereal plant, which as defined above includes at least a seed, progeny, or a part thereof, does not comprise a mis-division of the alien addition chromosome. In certain embodiments, the cereal plant does not comprise a breakage of the alien addition chromosome. In certain embodiments, the cereal plant does not comprise i) a mis-division of the alien addition chromosome nor ii) a breakage of the alien addition chromosome.

Homoeologous Pairing Approach

In certain embodiments, according to the various aspects of the present invention, the method can entail introducing a homoeologous pairing suppressor gene mutation to induce homoeologous pairing into a cereal plant line comprising a disomic alien addition chromosome carrying a male fertility restorer gene and at least one selection marker gene. In certain embodiments, the male fertility restorer gene and at least one selection marker gene are on different sides of the centromere of the alien addition chromosomes. In certain embodiments, male fertility restorer gene and at least one selection marker gene are on the same side of the centromere of alien addition chromosomes. In certain embodiments, the methods entail: a) selecting a cereal plant line homozygous for a male fertility gene mutation comprising at least one alien addition chromosome carrying a male fertility restorer gene and a selection marker gene on different sides of the centromere of the at least one alien addition chromosome; b) inducing homoeologous recombination of at least one alien addition chromosome or alien chromosome fragment; and c) obtaining a cereal plant comprising a homoeologous alien addition chromosome or alien chromosome fragment. The male fertility, male fertility restorer, and the selection marker genes are described in more detail above.

Homoeologous pairing, i.e., the pairing of equivalent chromosomes across different genomes or within the same genome but between chromosomes that usually do not pair, is prevented by the homoeologous pairing suppressor gene (Ph). In certain embodiments, the homoeologous pairing suppressor gene mutation is a gene deletion, a gene knockdown, or a gene knockout. As discussed in more detail above, mutated homoeologous suppressor genes (ph) (e.g., ph1b or ph2), can allow for homoeologous pairing. In certain embodiments, the homoeologous pairing suppressor gene mutation is a gene deletion from chromosome 5B or chromosome 3B. In certain embodiments, the deleted homoeologous pairing suppressor gene is ph1b or ph2.

In certain embodiments, the homoeologous recombination of step b) above results from a mutation of the homoeologous pairing suppressor gene. As such, the alien addition chromosome, or at least a fragment thereof, can become a part of the genome of the cereal plant. In certain embodiments, homoeologous pairing can occur by expressing genes that inhibit the homoeologous suppressor genes, such as, but not limited to, those from *Ae. speltoides*.

The homoeologous suppressor gene mutation can be introduced as a disomic alien addition chromosome. In certain embodiments, the homoeologous suppressor gene mutation is bred out of the cereal plant line. The homoeologous suppressor gene mutation can be detected directly by molecular and/or cytogenetic techniques generally known to those of skill in the art.

By way of example, and not limitation, the mutated homoeologous suppressor gene approach for the production of a hybrid cereal plant can be achieved by (see also as outlined in Example 3; FIG. 7):

Step a): crossing a first cereal plant homozygous for a male fertility gene mutation comprising a disomic alien addition chromosome carrying a dominant male fertility restoration gene and at least one selection marker gene with a second cereal plant homozygous for a male fertility gene mutation and for a homoeologous pairing suppressor gene mutation. In certain embodiments, a monosomic alien addition chromosome carrying the dominant male fertility restoration gene and at least one selection marker gene can be used.

Step b): harvesting, selecting, and planting at least one seed produced in step a) homozygous for a male fertility gene mutation comprising a monosomic alien addition chromosome carrying a dominant male fertility restoration gene and at least one selection marker gene and a single copy of the homoeologous pairing suppressor gene mutation.

Step c): self-fertilizing a cereal plant produced in step b).

Step d): harvesting, selecting, and planting at least one seed produced in step c) homozygous for a male fertility gene mutation and for the homoeologous pairing suppressor gene mutation comprising a euploid number of chromosomes and a monosomic alien addition chromosome.

Step e): self-fertilizing a cereal plant produced in step d).

Step f): harvesting at least four seeds from step e).

Step g): counting the number of the seeds of step f) from a first group expressing the at least one selection marker and a second group not expressing the at least one selection marker in order to determine the segregation ratio.

Step h): keeping the seeds of step f) if the ratio of the number of seeds of first group:second group tends to about 3:1 and discarding the seeds of step f) if the ratio of the number of seeds of first group:second group is other than about 3:1. For example, if the ratio is between about 1:1 to about 1:3, the seeds are to be discarded. The change in segregation shows a successful translocation of the monosomic chromosome into the genome. A seed set ratio of three marked seeds to one unmarked seeks is indicative of homoeologous pairing, whereby the alien addition chromosome has recombined with one of the homoeologous wheat chromosomes. In certain embodiments, the long arms of chromosomes 4A, 4B, 4D, or the distal region of chromosome 5A are homoeologous to the long arm of chromosome 4Ag (Ag: *Agropyron elongatum*). In certain embodiments, chromosome pairing between the alien addition chromosome and the 4A, 4B or 4D chromosomes can also occur on the short arms. In certain embodiments, homoeologous pairing can occur between other chromosomes as well.

In certain embodiments, the monosomic alien addition chromosome translocates with 4A, 4B, 4D, or 5A chromosomes. In certain embodiments, the monosomic alien addition chromosome does not translocates with the 4B chromosome.

In certain embodiments, the selection marker gene imparts a graded selection phenotype. For example, when the selection marker gene is present heterozygously the phenotype is of a certain amount (e.g., light blue) and when it is present homozygously, it is present in a greater amount (e.g., darker blue) than when it is heterozygously present.

In certain embodiments, the cereal plant, which, as defined above, includes at least a seed, progeny, or a part thereof, does not comprise a mis-division of the alien addition chromosome. In certain embodiments, the cereal plant does not comprise a breakage of the alien addition chromosome. In certain embodiments, the cereal plant does not comprise i) a mis-division of the alien addition chromosome nor ii) a breakage of the alien addition chromosome.

Gene Editing Integration Approach

In certain embodiments, according to the various aspects of the present invention, the method can entail gene editing to insert a male fertility restorer gene and optionally at least one selection marker gene. In certain embodiments, the method entails integrating a male fertility restorer gene and optionally at least one selection marker gene into either a wheat genome or an alien addition chromosome of a cereal plant. In certain embodiments, the integration is random. In certain embodiments, the integration is targeted.

In certain embodiments, the method entails: a) selecting a cereal plant line homozygous for a male fertility gene mutation; b) integrating into the genome or alien addition chromosome of the cereal plant line a male fertility restorer gene and optionally at least one selection marker gene, wherein the male fertility restorer gene and the at least one selection marker gene are genetically linked and in close proximity; and c) obtaining a cereal plant comprising the genetically linked male fertility restorer gene and at least one selection marker gene.

In certain embodiments, the cell comprises a male-sterile genotype.

In certain embodiments, the male fertility restorer gene and the at least one selection marker gene are introduced into a cell of the cereal plant line via gene expression cassettes that can be on the same or different DNA constructs. In certain embodiments, the male fertility restorer gene and the at least one selection marker gene are configured in the gene cassette as 5' to 5', 3' to 3', 5' to 3', or 3' to 5'. Once arranged in close proximity, the gene cassette can be introduced into the cereal plant.

In certain embodiments, the at least one selection marker gene is introduced so that the male-fertile phenotype can be used as an indicator of modified plants. In certain embodiments, the male fertility restorer gene is introduced so that the expression of the marker can be used to indicate the modified plants. After integration, the male fertility restorer gene is associated with the at least one selection marker gene and on the same side of the centromere of the monosomic alien addition chromosome.

In certain embodiments, the gene cassette is introduced in the cell by biological or physical means, including transfection, transformation, including transformation by *Agrobacterium* spp., preferably by *Agrobacterium tumefaciens*, a viral vector, biolistic bombardment (i.e., particle bombardment), transfection using chemical agents, including polyethylene glycol transfection, electroporation, electro cell fusion, or any combination thereof.

In certain embodiments, the gene cassette is introduced in the cell by *Agrobacterium*-mediated transformation of the male fertility restorer gene and blue aleurone gene harbored within T-DNA borders in a binary plasmid.

In certain embodiments, the gene cassette is introduced into the cell by particle bombardment of a plasmid comprising the gene cassette in supercoiled, circular, relaxed, or linear configurations. In certain embodiments, particle bombardment comprises a PCR-amplicon of the gene cassette, thereby resulting in the introduction of DNA only that is already present in the cereal plants harboring the monosomic alien addition chromosome disclosed herein.

In certain aspects, this method entails creating genomic single- or double-strand breaks (DSBs) at specific locations in the cereal plant genome of interest. The male fertility restorer gene and/or at least one selection marker gene can then be inserted at the site of the double-strand breaks. In certain embodiments, if male fertility restorer gene and/or at least one selection marker gene cassette is integrated by homologous recombination, the homology arms flanking the gene cassette are designed appropriately. For example, the genes can have about 20 to about 1000 base pairs in length on each side, with >90% homology to the genomic sequence on either side of the DSB site.

In certain embodiments, the integrating step b) comprises targeting the integration of the linked male fertility restorer gene and at least one selection marker gene using a site-specific nuclease designed to make a double-strand break at a target site in the cereal plant line genome and wherein the linked male fertility restorer gene and the at least one selection marker gene is integrated into the cereal plant line genome at the site of the double-strand break. In certain embodiments, the site-specific nuclease is a meganuclease, a TALEN, a ZFN, or a CRISPR nuclease. In certain embodiments, the site-specific nuclease is delivered into the cereal plant line cell by transformation of at least one DNA cassette encoding/expressing the required components for site-specific nuclease activity, by transformation of RNA molecules expressing the required components for site-specific nuclease activity, or by transformation of purified protein or ribonucleoprotein site-specific nuclease complexes. Site-specific nucleases and integration strategy is discussed in greater detail below.

In certain embodiments, a double strand break induced by the site-specific nuclease is the site at which the at least one selection marker gene and male fertility restorer gene cassettes are integrated into the cereal plant genome. In certain embodiments, no homology arms are required. In certain embodiments, the transformed linear PCR-amplicon consisting only of the cassettes. In certain embodiments, the plasmid is designed in a way that the nuclease cleaves the cassettes/repair template out of the plasmid in addition to inducing the genomic double stranded break.

In certain embodiments, the method entails the flanking of the at least one selection marker gene and male fertility restorer gene cassettes with upstream and downstream homology arms, so as to integrate the cassettes into the site of the double stranded break by homologous recombination. This can be defined as the repair template, with either, or both genes included between the homology arms.

In certain embodiments, the cell is from an immature embryo, a protoplast or a callus. In certain embodiments, the cell or tissue that can be used in this method is whole or partially dissected embryos. In certain embodiments, the meristem is bombarded directly and the embryo germinated to produce plants. In certain embodiments, the transformation method can further include transformed gene cassette that provides resistance to a herbicide, antibiotic, or other cytotoxic compound to track transformation.

In certain embodiments, the cell or tissue that is transformed is a male-sterile genotype and regenerate or geminate without selection. The male-fertile and selection marker phenotypes, or either phenotype individually, can be used to identify plants with both genes integrated in a location where they are properly expressed.

In certain embodiments, an "elite event" is identified, which is characterized by having a single-copy insertion in a preferred location in the cereal plant genome that does not disrupt a native gene sequence. In certain embodiments, the integrated gene cassette allows adequate expression of the genes. In certain embodiments, the integrated gene cassette allows for stable expression of the male fertility restorer gene and at least one selection marker gene.

Specific markers for the male fertility restorer gene and/or the at least one selection marker gene can be used for confirmation of the rearrangement. In certain embodiments, the methods comprise examining at least one selection marker gene expressing seed from the population to confirm the seed comprises a rearranged monosomic alien addition chromosome, which comprises the dominant male fertility restorer gene and the selection marker gene on the same side of the centromere of the rearranged monosomic alien addition chromosome. In certain embodiments, the examining step comprises conducting a cytological analysis or molecular analysis. In certain embodiments, the examining step comprises PCR-screening using primers to the added genes. In certain embodiments, the examining step comprises conducting FISH (fluorescence in-situ hybridization) or GISH (genomic in-situ hybridization) microscopy to detect the location of translocation.

In certain embodiments, the cereal plant, which as defined above includes at least a seed, progeny, or a part thereof, does not comprise a mis-division of the alien addition chromosome. In certain embodiments, the cereal plant does not comprise a breakage of the alien addition chromosome. In certain embodiments, the cereal plant does not comprise i) a mis-division of the alien addition chromosome nor ii) a breakage of the alien addition chromosome.

Gene Editing Rearrangement of the Alien Addition Chromosome Approach

In certain embodiments, according to the various aspects of the present invention, the method can entail the rearrangement of an alien addition chromosome that comprises both the male fertility restorer gene and at least one selection marker gene on different sides of the centromere. In certain embodiments, site-specific nucleases are used to generate the rearrangement.

In certain embodiments, the method entails: a) selecting a cereal plant line homozygous for a male fertility gene mutation; b) integrating into the alien addition chromosome or the genome of the cereal plant line either a male fertility restorer gene or at least one selection marker gene; and c) obtaining a cereal plant comprising a genetically linked male fertility restorer gene and at least one selection marker gene, wherein the genetically linked male fertility restorer gene and at least one selection marker gene are on the same side of the centromere of the alien addition chromosome. The method can further comprise disrupting the male fertility restorer gene and/or at least one selection marker gene located on the opposite side of the centromere as the genetically linked male fertility restorer gene and at least one selection marker gene.

In certain embodiments, the integration is random. In certain embodiments, the integration is targeted.

In certain embodiments, only the male fertility restorer gene or the at least one selection marker gene is introduced into the cell or tissue. For example, the male fertility restorer gene can be integrated in close proximity to the at least one selection marker gene located on a monosomic alien addition chromosome. As another example, the at least one selection marker gene can be integrated in close proximity to the male fertility restorer gene located on a monosomic alien addition chromosome.

In certain embodiments, the method entails introducing into a cell of the cereal plant line a gene cassette carrying the same or different at least one selection marker gene and a site-specific nuclease designed to make a double-strand break at a target site in the cereal plant line genome on the same side of the centromere of the alien addition chromosome as the male fertility restorer gene and wherein the same or different at least one selection marker gene is integrated into the cereal plant line genome at the site of the double-strand break.

In certain embodiments, the method entails introducing into a cell of the cereal plant line a gene cassette carrying the same or different male fertility restorer gene and a site-specific nuclease designed to make a double-strand break at a target site in the cereal plant line genome on the same side of the centromere of the at least one alien addition chromosome as the at least one selection marker gene and wherein the same or different male fertility restorer gene is integrated into the cereal plant line genome at the site of the double-strand break.

The method can also entail using at least two site-specific nucleases to rearrange the male fertility restorer gene and at least one selection marker gene present on opposite sides of the centromere of the alien addition chromosome so that they are present on the same side of the centromere of the alien addition chromosome.

In certain embodiments, the method entails introducing at least two different site-specific nucleases into a cell of the cereal plant line, wherein at least one site-specific nuclease makes a first double strand break close to the at least one selection marker gene but between the at least one selection marker gene and the end of the chromosome of the alien addition chromosome to create a first end of the chromosome and at least one other site-specific nuclease makes a second double strand break close to the male fertility restorer gene but between the male fertility restorer gene and the centromere of the alien addition chromosome to create a second chromosome end, and wherein the chromosome ends are swapped so that the at least one selection marker is on the same side of the centromere of the at least one alien addition chromosome as the male fertility restorer gene.

In certain embodiments, the method entails introducing at least two different site-specific nucleases into a cell of the cereal plant line, wherein at least one site-specific nuclease makes a first double strand break close to the male fertility restorer gene but between the male fertility restorer gene and the end of the chromosome of the alien addition chromosome to create a first end of the chromosome and at least one other site-specific nuclease makes a second double strand break close to the at least one selection marker gene but between the at least one selection marker gene and the centromere of the alien addition chromosome to create a second chromosome end, and wherein the chromosomes ends are swapped so that the at least one selection marker gene is on the same side of the centromere of the at least one alien addition chromosome as the male fertility restorer gene.

In certain embodiments, the first and second double strand breaks occur simultaneously. In certain embodiments, the first and second double strand breaks occur in close proximity in time.

In certain embodiments, the site-specific nuclease is a meganuclease, a TALEN, a ZFN, or a CRISPR nuclease. In certain embodiments, the site-specific nuclease is delivered into the cereal plant line cell by transformation of at least one DNA cassette encoding the required genes for site-specific nuclease activity, transformation of RNA molecules, or by transformation of purified protein or ribonucleoprotein complexes. Site-specific nucleases and integration strategy is discussed in greater detail below.

In certain embodiments, a double strand break induced by the site-specific nuclease is the site at which the at least one selection marker gene and male fertility restorer gene cassettes are integrated into the cereal plant genome. In certain embodiments, no homology arms are required. In certain embodiments, the transformed linear PCR-amplicon consisting only of the cassettes. In certain embodiments, the plasmid is designed in a way that the nuclease cleaves the cassettes/repair template out of the plasmid in addition to inducing the genomic double stranded break.

In certain embodiments, the method entails the flanking of the at least one selection marker gene and male fertility restorer gene cassettes with upstream and downstream homology arms, so as to integrate the cassettes into the site of the double stranded break by homologous recombination In certain embodiments, the cell is from an immature embryo, a mature embryo, a germinated embryo, a protoplast or a callus. In certain embodiments, the cell or tissue that can be used in this method is whole or partially dissected embryos. In certain embodiments, the meristem is bombarded directly and the embryo germinated to produce plants. In certain embodiments, the transformation method can further include a selection marker gene cassette to track transformation.

In certain embodiments, the cell or tissue that is transformed is a male-sterile genotype and regenerate or geminate without selection. The male-fertile and selection marker phenotypes can be used to identify plants with both genes integrated in a location where they are properly expressed.

In certain embodiments, an "elite event" is identified, which is characterized by having a single-copy insertion in a preferred location in the cereal plant genome that does not disrupt a native gene sequence. In certain embodiments, the integrated gene cassette allows adequate expression of the genes. In certain embodiments, the integrated gene cassette allows for stable expression of the male fertility restorer gene and at least one selection marker gene.

Specific markers for the male fertility restorer gene and/or the at least one selection marker gene can be used for confirmation of the rearrangement. In certain embodiments, the methods comprise examining at least one selection marker gene expressing seed from the population to confirm the seed comprises a rearranged monosomic alien addition chromosome, which comprises the dominant male fertility restorer gene and the selection marker gene on the same side of the centromere of the rearranged monosomic alien addition chromosome. In certain embodiments, the examining step comprises conducting a cytological analysis or molecular analysis. In certain embodiments, the examining step comprises PCR-screening using primers to the added genes. In certain embodiments, the examining step comprises conducting FISH (fluorescence in-situ hybridization) or GISH (genomic in-situ hybridization) microscopy to detect the location of translocation.

In certain embodiments, the cereal plant, which as defined above includes at least a seed, progeny, or a part thereof, does not comprise a mis-division of the alien addition chromosome, i.e. the two gene cassettes. In certain embodiments, the cereal plant does not comprise a breakage of the alien addition chromosome. In certain embodiments, the cereal plant does not comprise i) a mis-division of the alien addition chromosome nor ii) a breakage of the alien addition chromosome.

Maintenance of a Male-Sterile Female Parental Line

Also provided herein, are methods for the maintenance of a male-sterile parental cereal plant line for use in the production of hybrids cereal plants, which entails crossing a male-sterile female plant with a male parent plant similar to the female plant but having a chromosome bearing a male fertility restorer gene and a selection marker gene that confers a phenotypic characteristic to the progeny and/or progeny seed. From that cross, a population of progeny cereal plant seeds comprises a mixture of the two parental lines that can be separated based on the phenotypic characteristic. In certain embodiments, the chromosomes comprising the male fertility restorer gene is an alien addition chromosome.

For production of hybrid cereal seeds carrying the alien addition chromosome, homoeologous chromosome pair, and/or integrated nucleic acid construct, the hybrid cereal plant may be self-fertilized. Alternatively, the hybrid cereal plant can be crossed with a similar cereal plant or with a cereal plant that carries one or more nucleic acids that are different from the hybrid cereal plant, or with a non-transgenic plant of known plant breeding methods to produce hybrid cereal seeds. These cereal seeds can be used to provide progeny generations of hybrid cereal plants of the invention, comprising the alien addition chromosome, homoeologous chromosome pair, and/or integrated nucleic acid construct.

By way of example, and not limitation, a method for the maintenance of a male-sterile female parental line of a cereal plant for use in the production of hybrid cereal plants can be achieved by:

Step a): planting at least one seed comprising a homozygous male fertility gene mutation and a monosomic alien addition chromosome carrying a dominant male fertility restorer gene and at least one selection marker gene on the same side of the centromere of the monosomic alien addition chromosome, whereby seeds having this monomeric alien addition chromosome can be separated from seeds not having it to produce at least one progeny seed.

Step b): self-fertilizing a cereal plant produced in step a).

Step c): selecting at least one seed not comprising the monosomic alien addition chromosome for growing at least one sterile-female parent cereal plant for crossing with a fertile-male cereal plant for a hybrid cereal plant and a hybrid seed production.

Step d): selecting at least one seed comprising the monosomic alien addition chromosome for maintenance of the cereal plant.

By way of another example, and not limitation, a method for the maintenance of a male-sterile female parental line of a cereal plant for use in the production of hybrid cereal plants can be achieved by:

Step a): planting at least one seed comprising a homozygous male fertility gene mutation and at least one portion of an alien addition chromosome carrying a dominant male fertility restorer gene and at least one selection marker gene translocated into at least one chromosome of a homoeologous chromosome pair.

Step b): self-fertilizing a cereal plant produced in step a).

Step c): selecting at least one seed not comprising the alien addition chromosome translocated into at least one chromosome of a homoeologous chromosome pair for growing at least one sterile-female parent cereal plant for crossing with a fertile-male cereal plant for a hybrid cereal plant and a hybrid seed production.

Step d): selecting at least one seed comprising the alien addition chromosome translocated into one chromosome of a homoeologous chromosome pair for maintenance of the cereal plant, wherein the seed is heterozygous for the translocation as preferably indicated by the expression of the at least one selection marker gene.

Step e): discarding any seed comprising the alien addition chromosome translocated into at least two chromosomes of a homoeologous chromosome pair for maintenance of the cereal plant, wherein the seed is homozygous for the translocation as preferably indicated by expression of the at least one selection marker gene.

Site-Specific Nucleases of the Invention

In certain embodiments, according to the various aspects of the present invention, the at least one site-specific nuclease may comprise a zinc-finger nuclease, a transcription activator-like effector nuclease, a CRISPR/Cas system, an engineered homing endonuclease, and a meganuclease, zinc finger nucleases (ZFns), transcription activator-like effector nucleases (TALENs), and/or any combination, variant, or catalytically active fragment thereof.

A CRISPR system in its natural environment describes a molecular complex comprising at least one small and individual non-coding RNA in combination with a Cas nuclease or another CRISPR nuclease like a Cpf1 nuclease (Zetsche et al., 2015, supra) which can produce a specific DNA double-strand break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems, for example, can code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from Streptococcus pyogenes has been described to be "NGG" or "NAG" (Standard IUPAC nucleotide code) (Jinek et al, Science 2012, 337: 816-821). The PAM sequence for Cas9 from Straphylococcus aureus is "NNGRRT" or "NNGRR(N)". Further variant CRISPR/Cas9 systems are known. Thus, a Neisseria meningitidis Cas9 cleaves at the PAM sequence NNNNGATT. A Streptococcus thermophilus Cas9 cleaves at the PAM sequence NNAGAAW. Recently, a further PAM motif NNNNRYAC has been described for a CRISPR system of Campylobacter (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., Nature, 2017, 542, 237-241).

Presently, for example, Type II systems relying on Cas9, or a variant or any chimeric form thereof, as endonuclease have been modified for genome engineering. Synthetic CRISPR systems consisting of two components, a guide RNA (gRNA) also called single guide RNA (sgRNA) and a non-specific CRISPR-associated endonuclease can be used to generate knock-out cells or animals by co-expressing a gRNA specific to the gene to be targeted and capable of association with the endonuclease Cas9. Notably, the gRNA is an artificial molecule comprising one domain interacting with the Cas or any other CRISPR effector protein or a variant or catalytically active fragment thereof and another domain interacting with the target nucleic acid of interest and thus representing a synthetic fusion of crRNA and tracrRNA (as "single guide RNA" (sgRNA) or simply "gRNA"). The genomic target can be any ~20 nucleotide DNA sequence, provided that the target is present immediately upstream of a PAM sequence. The PAM sequence is of outstanding importance for target binding and the exact sequence is dependent upon the species of Cas9 and, for example, reads 5' NGG 3' or 5' NAG 3' (Standard IUPAC nucleotide code) (Jinek et al., Science 2012, supra) for a Streptococcus pyogenes derived Cas9. The PAM sequence for Cas9 from Straphylococcus aureus is NNGRRT or NNGRR(N). Many further variant CRISPR/Cas9 systems are known, including inter alia, Neisseria meningitidis Cas9 cleaving the PAM sequence NNNNGATT. A Streptococcus thermophilus Cas9 cleaving the PAM sequence NNAGAAW. Using modified Cas nucleases, targeted single-strand breaks can be introduced into a target sequence of interest. By the combined use of such a Cas nickase with different recombinant gRNAs highly site-specific DNA double-strand breaks can be introduced using a double nicking system. Using one or more gRNAs can further increase the overall specificity and reduce off-target effects.

Once expressed, the Cas9 protein and the gRNA form a ribonucleoprotein complex through interactions between the gRNA "scaffold" domain and surface-exposed positively-charged grooves on Cas9. Cas9 undergoes a conformational change upon gRNA binding that shifts the molecule from an inactive, non-DNA binding conformation, into an active DNA-binding conformation. Importantly, the "spacer" sequence of the gRNA remains free to interact with target DNA. The Cas9-gRNA complex will bind any genomic sequence with a PAM, but the extent to which the gRNA spacer matches the target DNA determines whether Cas9 will cut. Once the Cas9-gRNA complex binds a putative DNA target, a "seed" sequence at the 3' end of the gRNA targeting sequence begins to anneal to the target DNA. If the seed and target DNA sequences match, the gRNA will continue to anneal to the target DNA in a 3' to 5' direction (relative to the polarity of the gRNA).

Examples of Cas proteins useful in the compositions and methods of the invention include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, CasY, Csx3, Csx1, Csx15, Csf1, Csf2, Csf3, Csf4, and Cu1966, and homologs or modified versions thereof. P CRISPR/Cas, e.g. CRISPR/Cas9, and likewise CRISPR/Cpf1 or CRISPR/CasX or CRISPR/CasY and other CRISPR systems are highly specific when gRNAs are designed correctly, but especially specificity is still a major concern, particularly for clinical uses or targeted plant GE based on the CRISPR technology. The specificity of the CRISPR system is determined in large part by how specific the gRNA targeting sequence is for the genomic target compared to the rest of the genome. Therefore, the methods according to the present invention when combined with the use of at least one CRISPR nuclease as site-specific nuclease and further combined with the use of a suitable CRISPR nucleic acid can provide a significantly more predictable outcome of GE. Whereas the CRISPR complex can mediate a highly precise cut of a genome or genetic material of a cell or cellular system at a specific site, the methods presented herein provide an additional control mechanism guaranteeing a programmable and predictable repair mechanism.

According to the various embodiments of the present invention, the above disclosure with respect to covalent and non-covalent association or attachment also applies for CRISPR nucleic acids sequences, which may comprise more than one portion, for example, a crRNA and a tracrRNA portion, which may be associated with each other as detailed above. In one embodiment, a repair template nucleic acid sequence (e.g., comprising the gene to be inserted) of the present invention may be placed within a CRISPR nucleic acid sequence of interest to form a hybrid nucleic acid sequence according to the present invention, which hybrid may be formed by covalent and non-covalent association.

In yet a further embodiment according to the various aspects of the present invention, the one or more nucleic acid sequence(s) flanking the at least one nucleic acid sequence of interest at the predetermined location may have at least 85%-100% complementary to the one or more nucleic acid sequence(s) adjacent to the predetermined location, upstream and/or downstream from the predetermined location, over the entire length of the respective adjacent region(s). Notably, a lower degree of homology or complementarity of the at least one flanking region may be used, e.g. at least 70%, at least 75%, at least 80%, at least 81%, at least 82%, at least 83%, or at least 84% homology/complementarity to at least one adjacent region in the genetic material of interest. For high precision gene editing relying on HDR template, i.e., a repair template, more than 95% homology/complementarity are favorable to achieve a highly targeted repair event. As shown in Rubnitz et al., Mol. Cell Biol., 1984, 4(11), 2253-2258, also very low sequence homology might suffice to obtain a homologous recombination. As it is known to the skilled person, the degree of complementarity will depend on the genetic material to be modified, the nature of the planned edit, the complexity and size of a genome, the number of potential off-target sites, the genetic background and the environment within a cell or cellular system to be modified.

In certain embodiments, the site-specific nuclease can be zinc finger nucleases (ZFns), transcription activator-like effector nucleases (TALENs), meganucleases, and/or restriction endonucleases. Fusion RNA and fusion protein molecules using these site-specific nucleases, or functional fragment or derivative thereof, for use in the compositions and methods of the invention can be made in the same fashion and structure as that disclosed above for Cas molecules, or functional fragment or derivative thereof.

Transcription activator-like effector nucleases (TALEN) are restriction enzymes that can be engineered to cut target sequences of DNA. They are made by fusing a TAL effector DNA-binding domain to a DNA cleavage domain (a nuclease which cuts DNA strands). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. doi: 10.1093/nar/gkq704; and Miller et al. (2011) Nature Biotechnology 29:143-148; all of which are herein incorporated by reference in their entirety and for all purposes.

Examples of suitable TAL nucleases, and methods for preparing suitable TAL nucleases, are disclosed, e.g., in US Patent Application No. 2011/0239315, 2011/0269234, 2011/0145940, 2003/0232410, 2005/0208489, 2005/0026157, 2005/0064474, 2006/0188987, and 2006/0063231 (each hereby incorporated by reference in their entirety and for all purposes). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors.

In one embodiment, each monomer of the TALEN comprises 12-25 TAL repeats, wherein each TAL repeat binds a 1 bp subsite. In certain embodiments, the site-specific nuclease is a chimeric protein comprising a TAL repeat-based DNA binding domain operably linked to an independent nuclease. In certain embodiments, the independent nuclease is a FokI endonuclease. In one embodiment, the site-specific nuclease comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double-strand break at a target sequence.

In certain embodiments, the site-specific nuclease comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double-strand break.

The site-specific nuclease employed in the various methods and compositions disclosed herein can further comprise a zinc-finger nuclease (ZFN). Zinc finger nucleases (ZFNs) are a class of engineered DNA-binding proteins that assist targeted editing of the genome by creating double strand breaks (DSBs) in DNA at targeted locations. ZFNs comprise two functional domains: i) a DNA-binding domain comprising a chain of two-finger modules (each recognizing a unique hexamer (6 bp) sequence of DNA—two-finger modules are stitched together to form a Zinc Finger Protein, each with specificity of ≥24 bp) and ii) a DNA-cleaving domain comprising a nuclease domain of Fok I. When the DNA-binding and -cleaving domains are fused together, a highly-specific pair of "genomic scissors" are created.

In certain embodiments, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In certain embodiments, the independent endonuclease is a FokI endonuclease. In certain embodiments, the site-specific nuclease comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double-strand break. See, e.g., US20060246567; US20080182332; US20020081614; US20030021776; WO/2002/057308A2; US20130123484; US20100291048; and, WO/2011/017293A2, each of which is herein incorporated by reference in their entirety for all purposes.

In still another embodiment, the site-specific nuclease is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see e.g., Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see e.g., Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346; all of which are herein incorporated by reference in their entirety and for all purposes.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AnaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PculP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-DmoI.

Site-specific nucleases can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.); all of which are herein incorporated by reference in their entirety and for all purposes.

All SSNs introduce DSBs in a target genomic sequence and activate non-homologous end-joining (NHEJ)-mediated DNA repair, which generates a mutant allele comprising an insertion or a deletion of a nucleic acid sequence at the genomic locus of interest and thereby causes disruption of the genomic locus of interest in a cell. DSBs also stimulate homology-directed repair (HDR) by homologous recombination if a repair template is provided. HDR can result in a perfect repair that restores the original sequence at the broken site, or it can be used to direct a designed modification, such as a deletion, insertion, or replacement of the sequence at the site of the double strand break.

The site-specific nuclease may introduce double-strand breaks in the target nucleic acid, (e.g. genomic DNA). The double-stranded break can stimulate a cell's endogenous DNA-repair pathways (e.g., HR, NHEJ, A-NHEJ, or MMEJ). The modifications of the target nucleic acid due to NHEJ and/or HR can lead to, for example, mutations, deletions, alterations, integrations, gene correction, gene replacement, gene tagging, transgene insertion, nucleotide deletion, gene disruption, and/or gene mutation. The process of integrating non-native nucleic acid into genomic DNA can be referred to as gene editing. In certain embodiments, after a target nucleic acid is cleaved by the site-specific nuclease, the site of cleavage can be destroyed (e.g., the site may not be accessible for another round of cleavage with the original nucleic acid-targeting nucleic acid and site-specific nuclease).

Homologous recombination (HR) can occur with a homologous template. The homologous template can comprise sequences that are homologous to sequences flanking the target nucleic acid cleavage site. Homologous recombination entails a repair in which a repair template comprising a second DNA sequence with homology to the cleaved target locus sequence is used as a template for repair of the cleaved target locus sequence, resulting in the transfer of genetic information from the repair template to the target locus. As a result, new nucleic acid material (e.g., a male fertility restorer gene and/or at least one selection marker gene) is inserted/copied into the DNA break site. These methods lead to, for example but not limited to, gene correction, gene replacement, gene tagging, transgene insertion, nucleotide deletion, gene disruption, gene mutation, and/or gene knockdown. NHEJ can repair cleaved target nucleic acid without the need for a homologous template. This can result in deletions of the target nucleic acid (e.g., a gene you are trying to disable). In NHEJ, the double-strand breaks can be repaired by direct ligation of the broken ends to one another. As such, no new nucleic acid material is inserted into the target locus—although, some nucleic acid material may be lost, resulting in a deletion.

Delivery Methods

A variety of methods are known for the introduction of nucleotide sequences and polypeptides into a cell, including, for example, transformation, and the introduction of the polypeptide, DNA, or mRNA into the cell. In certain embodiments, the site-specific nuclease is provided as a protein. In certain embodiments, the site-specific nuclease is provided as a nucleic acid, such as for example and not limitation, an mRNA.

A variety of suitable transient and stable delivery techniques suitable according to the methods of the present invention for introducing genetic material, biomolecules, including any kind of single-stranded and double-stranded DNA and/or RNA, or amino acids, synthetic or chemical substances, into a eukaryotic cell, preferably a plant cell, or into a cellular system comprising genetic material of interest, are known to the skilled person. Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include (in addition to those listed herein) polyethylene glycol-mediated transformation, microparticle bombardment, pollen-tube mediated introduction into fertilized embryos/zygotes, microinjection (Crossway et al., Biotechniques (1986) 4:320-34 and U.S. Pat. No. 6,300,543), meristem transformation (U.S. Pat. No. 5,736,369), electroporation (Riggs et al., Proc. Natl. Acad. Sci. USA (1986) 83:5602-6), *Agrobacterium*-mediated transformation (U.S. Pat. Nos. 5,563,055 and 5,981,840), direct gene transfer (Paszkowski et al., EMBO J. (1984) 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in Plant Cell, Tissue, and Organ Culture: Fundamental Methods, ed. Gamborg & Phillips (Springer-Verlag, Berlin); McCabe et al., Biotechnology (1988) 6:923-6; Weissinger et al., Ann Rev Genet (1988) 22:421-77; Sanford et al., Particulate Science and Technology (1987) 5:27-37 (onion); Christou et al., Plant Physiol (1988) 87:67-74 (soybean); Finer and McMullen, In Vitro Cell Dev Biol (1991) 27P:175-82 (soybean); Singh et al., Theor Appl Genet (1998) 96:319-24 (soybean); Datta et al., Biotechnology (1990) 8:736-40 (rice); Klein et al., Proc. Natl. Acad. Sci. USA (1988) 85:4305-9 (maize); Klein et al., Biotechnology (1988) 6:559-63 (maize); U.S. Pat. Nos. 5,240,855; 5,322,783 and 5,324,646; Klein et al., Plant Physiol (1988) 91:440-4 (maize); Fromm et al., Biotechnology (1990) 8:833-9 (maize); Hooykaas-Van Slogteren et al., Nature (1984) 311:763-4; U.S. Pat. No. 5,736,369 (cereals); Bytebier et al., Proc. Natl. Acad. Sci. USA (1987) 84:5345-9 (Liliaceae); De Wet et al., (1985) in The Experimental Manipulation of Ovule Tissues, ed. Chapman et al., (Longman, N.Y.), pp. 197-209 (pollen); Kaeppler et al., Plant Cell Rep (1990) 9:415-8) and Kaeppler et al., Theor Appl Genet (1992) 84:560-6 (whisker-mediated transformation); D'Halluin et al., Plant Cell (1992) 4:1495-505 (electroporation); Li et al., Plant Cell Rep (1993) 12:250-5; Christou and Ford Annals Botany (1995) 75:407-13 (rice) and Osjoda et al., Nat Biotechnol (1996) 14:745-50 (maize via *Agrobacterium tumefaciens*); all of which are incorporated by reference in their entirety for all purposes.

Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) Science 233:496-498, and Fraley et al (1983) Proc. Nat'l. Acad. Sci. USA 80:4803. The virulence functions of the *Agrobacterium tumefaciens* host will direct the insertion of the construct and adjacent marker into the plant cell DNA when the cell is infected by the bacteria using binary T DNA vector (Bevan (1984) Nuc. Acid Res. 12:8711-8721) or the co-cultivation procedure (Horsch et al (1985) Science 227:1229-1231). The *Agrobacterium* transformation system may also be used to transform, as well as transfer, DNA to monocotyledonous plants and plant cells. See Hernalsteen et al (1984) EMBO J 3:3039-3041; Hooykass-Van Slogteren et al (1984) Nature 311:763-764; Grimsley et al (1987) Nature 325:1677-179; Boulton et al (1989) Plant Mol. Biol. 12:31-40; and Gould et al (1991) Plant Physiol. 95:426-434.

Alternatively, polynucleotides may be introduced into plants by contacting plants with a virus or viral nucleic acids. Generally, such methods involve incorporating a polynucleotide within a viral DNA or RNA molecule. In some embodiments, a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191; 5,889,190; 5,866,785; 5,589,367 and 5,316,931.

In other embodiments, an RNA polynucleotide encoding the site-specific nuclease protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122). Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al, Mol. Gen. Genet. (1986) 202:179-85; Nomura et al, Plant Sci. (1986) 44:53-8; Hepler et al., Proc. Natl. Acad. Sci. USA (1994) 91: 2176-80; and Hush et al., J. Cell Sci. (1994) 107:775-84.

For particle bombardment or with protoplast transformation, the expression system can comprise one or more isolated linear fragments or may be part of a larger construct that might contain bacterial replication elements, bacterial selectable markers or other detectable elements. The expression cassette(s) comprising the polynucleotides encoding the guide and/or Cas may be physically linked to a marker cassette (e.g., comprising a transformed gene that provides resistance to a herbicide, antibiotic, or other cytotoxic compound) or may be mixed with a second nucleic acid molecule encoding the marker cassette. The marker cassette is comprised of necessary elements to express a detectable or selectable marker that allows for efficient selection of transformed cells.

The above delivery techniques, alone or in combination, can be used for in planta approaches or to deliver into in vitro cells.

To be able to provide highly active molecules to a cellular system of interest, in certain embodiments it may thus be preferred to provide pre-assembled and function molecular complexes comprising at least one site-specific nuclease, optionally at least one gRNA (for CRISPR nucleases), and further providing a nucleic acid sequence of interest, preferably flanked by at least one homology region in the form of a repair template, to be able to provide a fully functional gene editing complex to a cell or cellular system.

In any of the methods disclosed herein, the site-specific nuclease may be optimized for expression in plants, including but not limited to plant-preferred promoters, plant tissue-specific promoters, and/or plant-preferred codon optimization, as discussed in more detail herein.

Additional methods and compositions for use with the present invention are found in US2015/0152398, US2016/0145631, WO2016/205749, and WO2016/196655; all of which are herein incorporated by reference in their entirety and for all purposes.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Gametocidal (Gc) Genes Approach to the Improved BLA System

Gametocidal (Gc) genes, also known as Cuckoo genes, are known to cause gamete abortion and chromosome breakage. The Gc factor located on chromosome 4Mg of *Ae. geniculata* which, when transferred to common wheat, causes moderate chromosome breakage mainly in gametophytes lacking the Gc factor. As a result, multicentric and ring chromosomes can be produced that initiate breakage fusion bridge cycles, which can persist in the derived sporophytes. Weak gametocidal (Gc) genes, which induce fewer breaks as compared to strong Gc genes, can be used to induce chromosome structural changes (Kynast R G, Friebe B, Gill B S. 2000, *Chromosome Res.* 8:133-139). As a result, gametes without the Gc gene are functional and allow selecting of chromosomal aberrations in the offspring of such plants.

FIG. 5 demonstrates the preferred breeding scheme to arrive at a wheat line carrying an alien addition chromosome having rearranged BLA locus and/or restorer locus. The individual steps are described as follows:

In a first cross, a Gc chromosome has been introduced into a wheat line carrying the alien addition chromosome (blue color/restorer) and homozygously the 'Probus' deletion. Progenies having a chromosomal make-up comprising the disomic 21 wheat chromosomes, one monosomic alien addition chromosome (blue color/restorer) and monosomic gametocidal chromosome as well as hemizygously the 'Probus' deletion, were selected for further breeding. The seeds of these progenies are blue colored and fertile (i.e., 21"+B'+2C (Msms)). Produced fertile white seeds were discarded.

In a second cross, the selected progenies of the first cross were crossed again with a wheat line carrying the alien addition chromosome (blue color/restorer) and homozygously the 'Probus' deletion. From the resulting progenies, those F1 seeds were selected that carry the blue color gene and the Gc gene(s) as well as homozygously the 'Probus deletion', but without the $2C^c$ chromosome. Plants grown from this F1 seeds are self-fertilized subsequently. Blue seeds (F2) harvested from these plants are used for growing F2 plants which are self-fertilized again in order to produce F3 seeds.

The F3 seed are separated based on seed color. All white seeds (~1-200) were planted as a population bulk and phenotyped for fertile ears. Any population showing no fertile ears could have a rearranged alien addition chromosome and corresponding blue seed are checked cytologically to confirm if any favorable rearranging of this chromosome has happened.

The planting of the white seeds in F3 and checking for complete sterility shows, that the rearrangement has occurred. Otherwise, one expects to see the 1-2% fertile plants, which indicate, that the rearrangement has not occurred.

Figure 14A:
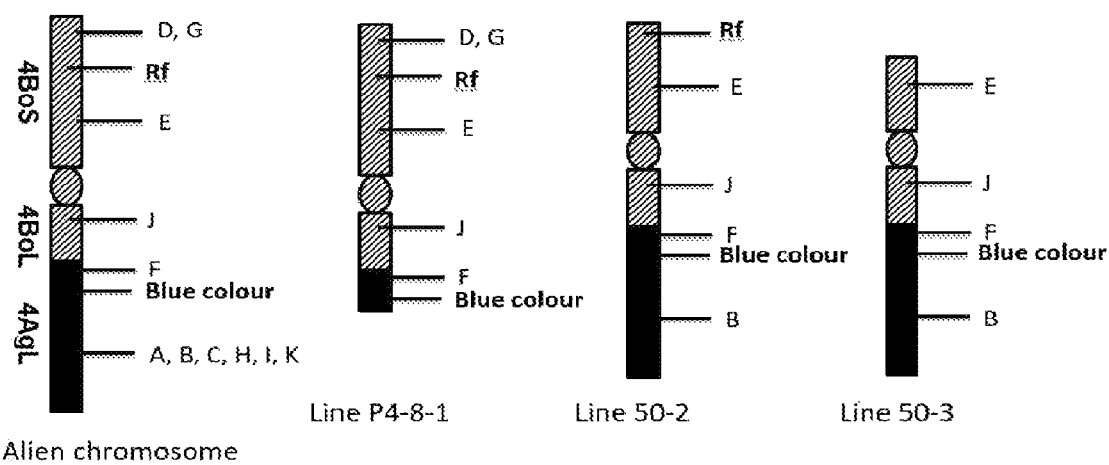
FIG. 14A-B shows the marker development for alien chromosome.
Figure 14B:
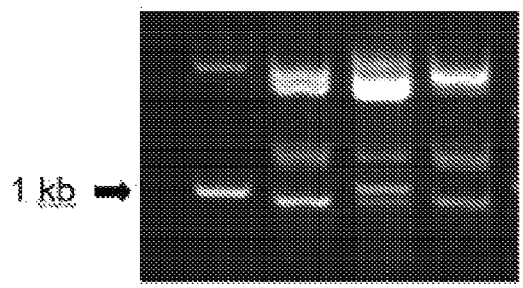

Any specific markers for the fertility and genes for color can be used for confirmation of the rearrangement (e.g., Table 1). FIG. 14 shows the distribution of the markers on the alien addition chromosome (A) as well as a gel chromatography for detection of the restorer gene (Rf).

TABLE 1

List of markers usable for the detection of the alien addition chromosome as well as the translocation of the alien addition chromosome or parts thereof onto the chromatin of the wheat genome.

| Marker | Primer name | Primer sequence (5'-3') | PCR condition | Product | Specific to genome | Linkage |
|---|---|---|---|---|---|---|
| A | 5565329F<br>5565329R | TGCAGTGATCCCGATGCCG (SEQ ID NO: 16)<br>CTCGGTGCGATGTGTGG (SEQ ID NO: 17) | 94C 3', 35 cycles of 94C 10" + 60C 30" | ~70 bp, dominant | *Agropyron elongatum* | L-arm, Blue-gene |
| B | 5570804F<br>5570804R | TGCAGGATTTTCCACTGATTAAC (SEQ ID NO: 18)<br>CGGAGGTGGTACGCGGTG (SEQ ID NO: 19) | 94C 3', 35 cycles of 94C 10" + 60C 30" | ~70 bp, dominant | *Agropyron elongatum* | L-arm, Blue-gene |
| C | 5564956F<br>5564956R | TGCAGAACTACCAGAATCTTTATCGG (SEQ ID NO: 20)<br>CTGTGAAACCAAGCACCCATAATC (SEQ ID NO: 21) | 94C 3', 35 cycles of 94C 10" + 60C 30" | ~70 bp, dominant | *Triticum boeticum, Agropyron elongatum* | L-arm, Blue-gene |
| D | 5008421F<br>5008421R | TGCAGAGCAAGAGCAACATTCAA (SEQ ID NO: 22)<br>CGGTCAATGTATAAACCACGTGC (SEQ ID NO: 23) | 94C 3', 35 cycles of 94C 10" + 60C 30" | ~70 bp, dominant | *Triticum boeticum* | S-arm, Rf |
| E | 3573220F<br>3573220R | TGCAGTCAGTCAACGATGG (SEQ ID NO: 24)<br>GTCTCACGTGCAGCGCA (SEQ ID NO: 25) | 94C 3', 35 cycles of 94C 10" + 60C 30" | ~70 bp, dominant | *Triticum monococcum, Agropyron elongatum* | S-arm, Rf |
| F | 5565375F<br>5565375R | TGCAGTTTCTATCATGTCCACG (SEQ ID NO: 26)<br>ATCTCGGGTTTATCTTCAGGG (SEQ ID NO: 27) | 94C 3', 35 cycles of 94C 10" + 60C 30" | ~70 bp, dominant | *Triticum monococcum, Triticum boeticum* | L-arm, Blue-gene |
| G | 1861695F<br>1861695R | TGCAGGTGTGCTACTTAGGGC (SEQ ID NO: 28)<br>CGGACCTTGCCCTGAGGAG (SEQ ID NO: 29) | 94C 3', 35 cycles of 94C 10" + 60C 30" | ~70 bp, dominant | *Agropyron elongatum* | S-arm, Rf |
| H | 5571044F<br>5571044R | TGCAGTGGAAAGTGCGGC (SEQ ID NO: 30)<br>CGGTAGATAGAAGATGAGACTTTACC (SEQ ID NO: 31) | 94C 3', 35 cycles of 94C 10" + 0C 30" | ~70 bp, dominant | *Agropyron elongatum* | L-arm, Blue-gene |
| I | 5565269F<br>5565269R | TGCAGGTGGACCTCATGGACTAC (SEQ ID NO: 32)<br>CTCAGGCACACCGCGCAGTC (SEQ ID NO: 33) | 94C 3', 35 cycles of 94C 10" + 65C 30" | ~70 bp, dominant | *Agropyron elongatum* | L-arm, Blue-gene |

TABLE 1-continued

List of markers usable for the detection of the alien addition chromosome as well as the translocation of the alien addition chromosome or parts thereof onto the chromatin of the wheat genome.

| Marker | Primer name | Primer sequence (5'-3') | PCR condition | Product | Specific to genome | Linkage |
|---|---|---|---|---|---|---|
| J | 5570850F | TGCAGGCGGT CCTGGACAGG (SEQ ID NO: 34) | 94C 3', 35 cycles of 94C 10" + 70C 30" | ~70 bp, dominant | *Agropyron elongatum* | L-arm, Blue-gene |
|  | 5570850R | CGGCCGCCCT CACCACAC (SEQ ID NO: 35) |  |  |  |  |
| K | 5565089F | TGCAGCATTG GCAAATAACA C (SEQ ID NO: 36) | 94C 3', 35 cycles of 94C 10" + 57C 30" | ~70 bp, dominant | *Agropyron elongatum* | L-arm, Blue-gene |
|  | 5565089R | GGTTGCATTCT CTGTGTATCAC (SEQ ID NO: 37) |  |  |  |  |
| Rf | RfF1 | GCCGCCGCCT GCGAAGG (SEQ ID NO: 38) | 94C 3', 30 cycles of 94C 20" + 68C 20" + 72C 1'30"; 1.5% agarose gel, run 1.5 hr at 100v | ~1 kb; the top band of double bands at ~1 kb is from the restorer; lines without restorer showed a single band <1 kb. (see FIG. 14 B) |  |  |
|  | RfR1 | GGGGGAGCGG GTCCTGC (SEQ ID NO: 39) |  |  |  |  |
| Blue gene marker | ThMYC4 ESpF | CTCCCAGTCA GGAACAGC (SEQ ID NO: 40) | 94C 3', 30 cycles of 94C 20" + 56C 20" + 72C 30" 2% agarose gel, run 40 min at 100v | a band at ~450 bp that is specific to the blue aleurone gene |  |  |
|  | TaMYC4 SpR | GGTGACAGTG AGGCGGTT (SEQ ID NO: 41) |  |  |  |  |

Lines with rearranged alien addition chromosome can be backcrossed with elite wheat line to eliminate any other unwanted chromosome rearrangements in the 42 wheat chromosomes.

Example 2

Irradiation Approach to the Improved BLA System

FIG. 6 demonstrates the preferred breeding scheme to arrive at a wheat line carrying an alien addition chromosome having rearranged BLA locus and/or restorer locus. The individual steps are described as follows:

Batches of seeds carrying the alien addition chromosome (blue color/restorer) and homozygously the 'Probus' deletion (i.e., 21"+B') were irradiated with 175, 200, 225 and 250 Gy of γ-ray. This is known to produce chromosome breakage at different levels. A large number of seeds (M0) were germinated with varying levels of plant survival expected for the different radiation levels. Seed-setting plants were harvested. All seeds harvested from one individual plant were collected in an M1 population comprising white and blue seeds.

Per population the seeds are separated based on color. All (~1-200) white seeds (M1) from each harvested M0 plant are grown in trays for phenotyping. Any M1 population containing white seeds showing any fertile plants is discarded; any M1 population containing white seeds showing zero fertile plants is increased by self-fertilizing the corresponding blue seeds (M1). From that cross, ~1,000 of white M2 seed are phenotyped. Any M2 population containing white seeds showing any fertile plants are discarded; any M2 population containing white seeds with zero fertile plants is examined cytologically to determine the chromosome composition of the alien addition chromosome with regard to a possible rearrangement of BLA locus and/or restorer locus.

Also, a backcrossing process can be started to eliminate all unwanted mutations and rearrangements in the 42 wheat chromosomes.

Example 3.1 ph1b Induced Homoeologous Pairing Approach to the Improved BLA System

Homoeologous pairing, i.e. the pairing of equivalent chromosomes across the three different genomes, is prevented by the homoeologous pairing (ph) gene. The known mutant ph1b derived from Chinese Spring Wheat allows homoeologous pairing to occur. In FIG. 7, a two-step approach for creating a substitution line is shown:

Crossing first a wheat line carrying the disomic alien addition chromosome (blue color/restorer) with a ph1b-wheat line induces homoeologous pairing between the alien addition chromosome and one of its wheat homoeologues, for example 4A, 4B, 4D or 5A (see FIG. 4).

After the initial cross, the F1 plants carrying the monosomic alien addition chromosome and heterozygously the mutated Ph1, i.e. the ph1b mutation, were self-fertilized to produce seeds with the following chromosomal/genetic make-up: 21 disomic wheat chromosomes and the monosomic alien addition chromosome and the ph1b mutation located on the long arm of chromosome 5B was homozygously present.

In order to determine successful translocation of the monosomic chromosome into the genome plants grown from these seeds, they were self-fertilized for a second time and segregation into blue and white seeds (F2) and analyzed. The change in the segregation showed a successful translocation of the monosomic chromosome into the genome. A successful rearrangement was proven by a segregation of blue seeds to white seeds from 3:1 or a ratio significantly deviated from 1:3 and by determination of the presence of 42 chromosomes.

A seed set ratio of more blue as compared to while (e.g., three blue to one white) on F2 plants is indicative of homoeologous pairing, whereby the alien addition chromosome has recombined with one of the homoeologous wheat chromosomes. It is presumed that the long (L) arms of chromosomes 4A, 4B, 4D, or the distal region of chromosome 5A are homoeologous to the long arm of chromosome 4Ag (Ag: *Agropyron elongatum*), and there is nothing on these long arms that should reduce the frequency of homoeologous pairing. Chromosome pairing between the alien addition chromosome and the 4A, 4B or 4D chromosomes can also occur on the short (S) arms. It is not inconceivable that pairing could happen with other wheat chromosomes as well.

For apparent translocation lines expressing the blue aleurone color, any homoeologous exchange on the long arm will still include the blue aleurone gene. The resulting chromosome from a translocation to a wheat chromosome 4 (4Ta—*Triticum aestivum*) can be designated as:

4AgL(blue)-4BoL.4BoS(fertility restorer)-4TaS or
4AgL(blue)-4BL.4BoS(fertility restorer)-4TaS Either of the above reciprocal exchanges would pair with a wheat chromosome 4 to give an open bivalent association. The 4B chromosome for example would carry the gene for male sterility or lacks the gene for male fertility ('Probus' deletion). The possible and preferred outcomes are:

Translocation onto chromosome 4A:
Chromosome 1=4AL.4AS
Chromosome 2=4AL-4AgL(blue)-4BoL.4BoS(fertility restorer), or 4AL-4AgL(blue)-4BL.4BoS(fertility restorer)
or
Chromosome 1=4AL.4AS
Chromosome 2=4AgL(blue)-4BoL.4BoS(fertility restorer)-4AS, or 4AgL(blue)-4BL.4BoS(fertility restorer)-4AS
Translocation onto chromosome 4B:
Chromosome 1=4BL.4BS(deletion)
Chromosome 2=4BL-4AgL(blue)-4BoL.4BoS(fertility restorer), or 4BL-4AgL(blue)-4BL.4BoS(fertility restorer)

Translocation onto chromosome 4D:
Chromosome 1=4DL.4DS
Chromosome 2=4DL-4AgL(blue)-4BoL.4BoS(fertility restorer), or 4DL-4AgL(blue)-4BL.4BoS(fertility restorer)
or
Chromosome 1=4DL.4DS
Chromosome 2=4AgL(blue)-4BoL.4BoS(fertility restorer)-4DS, or 4AgL(blue)-4BL.4BoS(fertility restorer)-4DS Presumed 42 chromosome lines will be tested cytologically to identify the location of translocation. Lines which exhibit translocation of the Bla-chromosome onto a wheat chromosome will be selected for further testing and crossing with normal Ph1 with the msms deletion.

Figure 8:
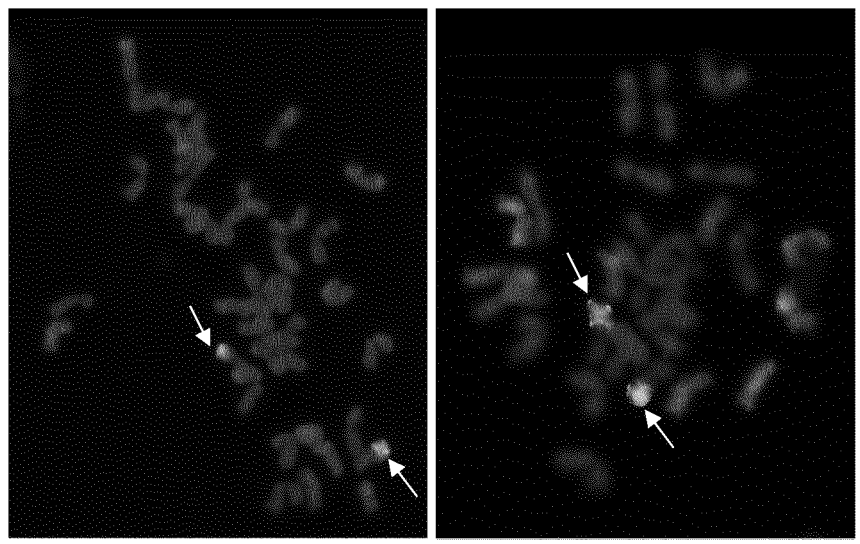
FIG. 8 shows *Agropyron* translocation (arrow).
Figure 10:
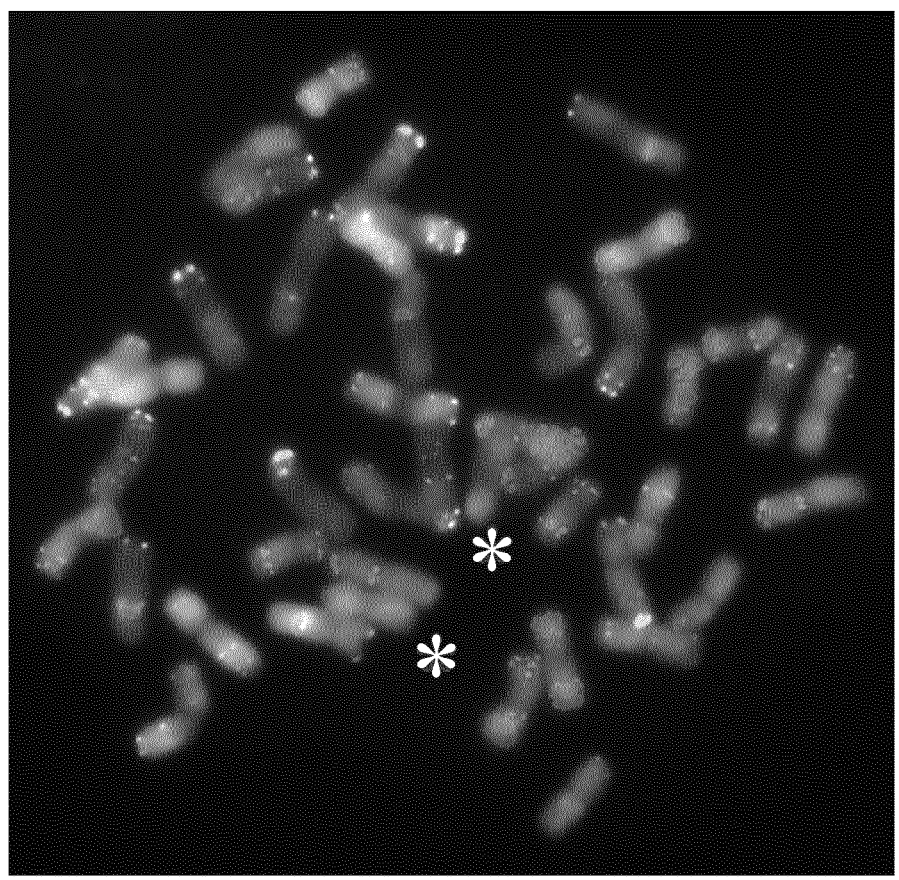
FIG. 10 shows Fluorescence In Situ Hybridization (FISH) photo of DB AR5. 44 chromosomes can be identified (21"+BoAg"). The star indicates the two Bla-chromosomes.

By use of different genotypes the first cross resulted in various progeny population, which have been tested on their chromosomal make-up (see Table 2). FIG. 8 shows the lighting up of translocations by labelling *Agropyron chromatin*. Viable plants were produced.

TABLE 2 shows there are some lines with 42 chromosomes and blue seed but not all have been checked for presence of Agropyron translocation yet.

| genotype | population | sample | copy of Ag. | chromosome No. | plant cond. |
|---|---|---|---|---|---|
| Pavon | 8 | 8-4 | 2 | 44 | |
| | 92 | 92-1 | 1 | 43 | |
| | 110 | 110-2 | 1 | 43 | |
| Angas | P4-2 | P4-2-1 | n.d. | 42 | very weak |
| | | P4-2-3 | n.d. | 42 | weak |
| | | P4-2-4 | 2 | 43 | |
| | P4-8 | P4-8-3 | n.d. | 43 | |
| | P5-5 | P5-5-3 | 1 | 42 | very weak |
| | P7-1 | P7-1-1 | n.d. | 42 | very weak |
| | | P7-1-2 | n.d. | 42 | healthy |
| | | P7-1-4 | 2 | 42 | healthy |
| | P7-3 | P7-3-1 | n.d. | 42 | healthy |
| | | P7-3-3 | n.d. | 42 | weak |
| | P7-5 | P7-5-1 | n.d. | 41 | healthy |
| | | P7-5-3 | n.d. | 42 | healthy |

Table of FIG. 9 shows a further set of seed population for which the presence of translocations has been checking, translocations have been confirmed and it has been identified onto which wheat chromosomes the translocation has occurred (see also Fluorescence in situ hybridization (FISH) colour photos of FIGS. 10 to 13). Table of FIG. 9 presents the first results from Fluorescence In Situ Hybridization (FISH) chromosome scanning of Blue-aleurone (Bla) parental lines, ph1b-mutant lines, and lines derived from original crosses between Bla-lines and ph1b-mutant lines.

Figure 12:
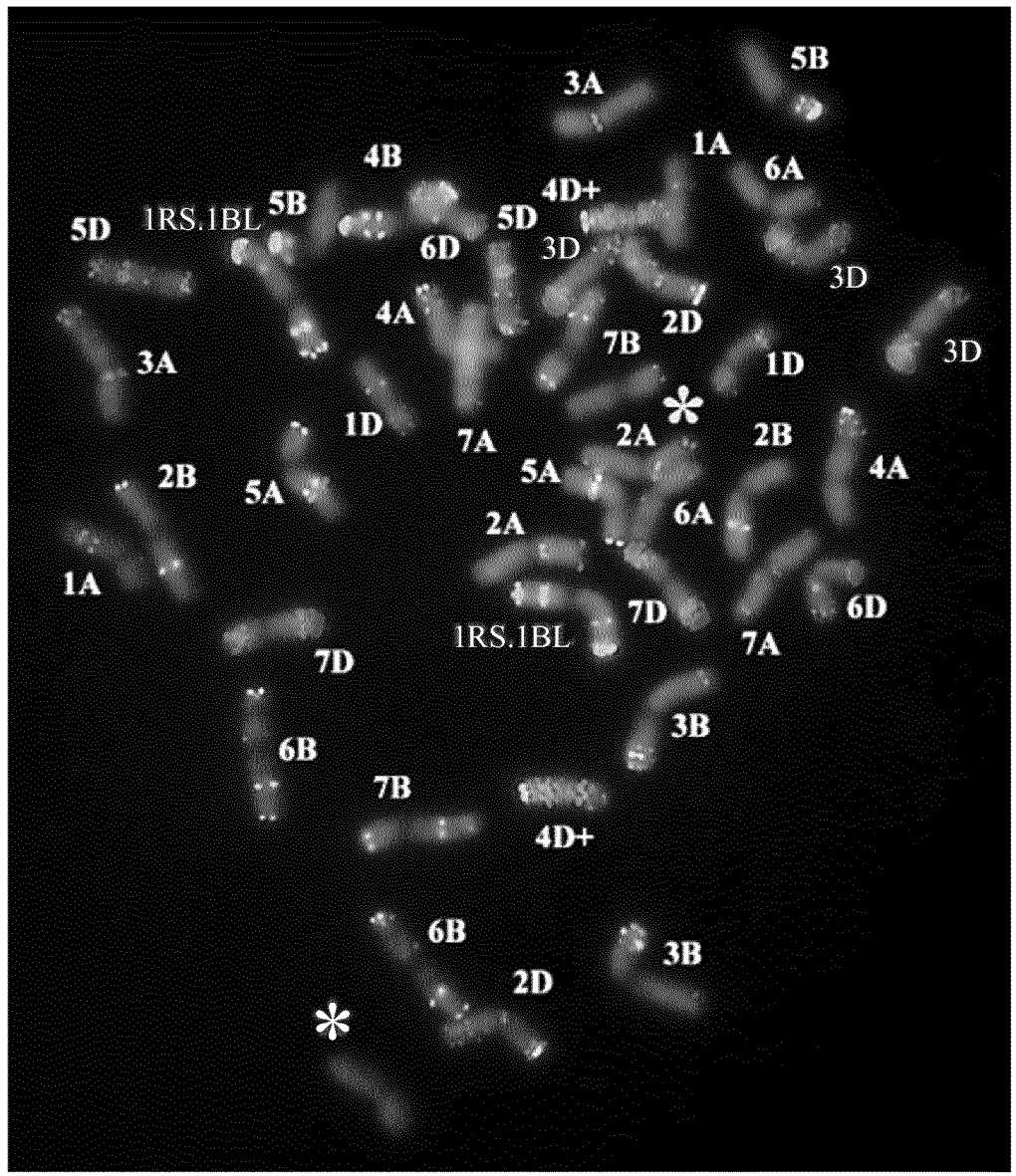
FIG. 12 shows Fluorescence In Situ Hybridization (FISH) photo of lines 149-4-7. 44 chromosomes can be identified (19"+4B'+3D"'+BoAg'+T4DS-4BoS.4BoL-4AgL'). The star indicates an alien chromosome. The star with the arrow indicates a translocation of the Bla-chromosome onto chromatin from wheat chromosome 4DS.
Figure 13:
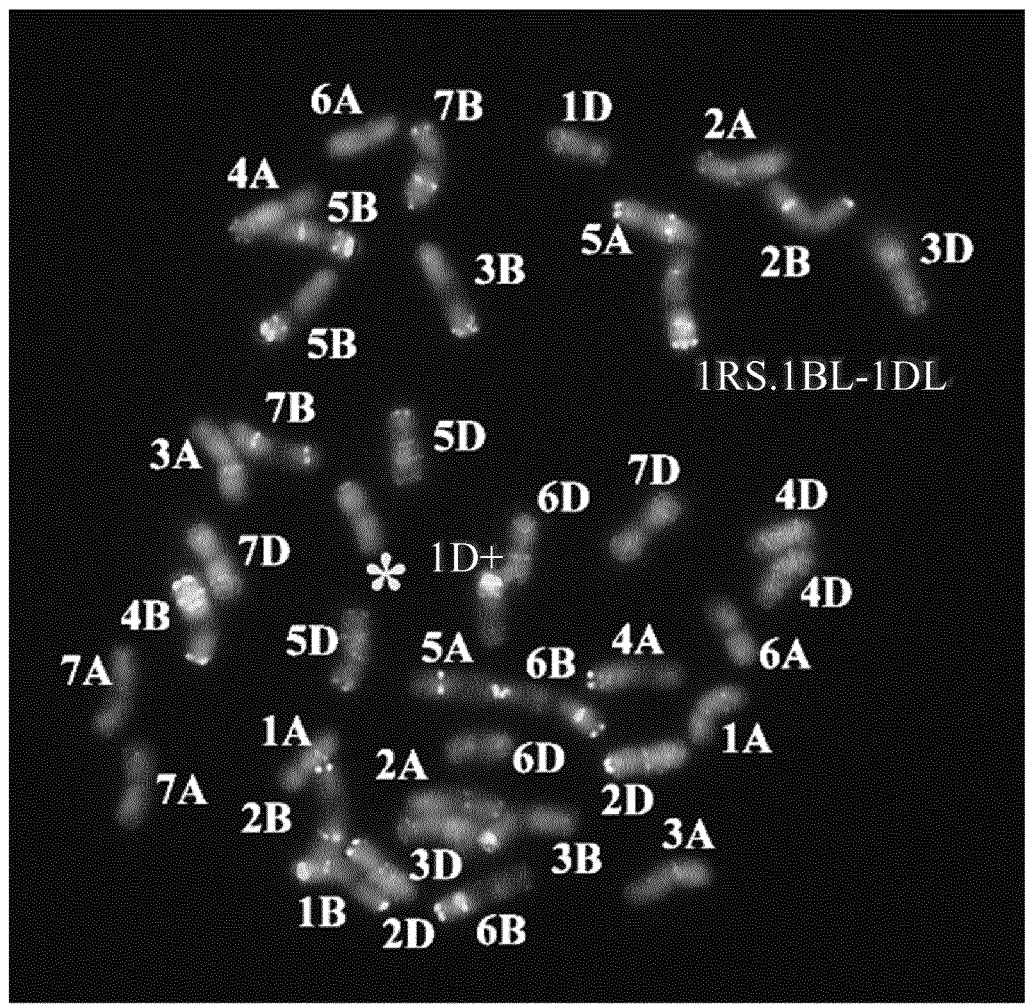
FIG. 13 shows Fluorescence In Situ Hybridization (FISH) photo of line E-2 (149-4 x AR23-6). 42 chromosomes can be identified (18"+1B'+T1RS.1BL-1DL'+4B'+1D'+T1DS.1DL-1BL'+T4DS-4BoS.4BoL-4AgL'). The star with the arrow indicates a translocation of the Bla-chromosome onto chromatin from wheat chromosome 4DS.

The photos of FIGS. 11 to 13 proof that translocations have occurred. They confirm for example that translocations occurred onto chromatin from wheat chromosome 4B short arm (FIGS. 11A and B) and onto chromatin from wheat chromosome 4D short arm (FIGS. 12 and 13). Next step will be selfing and cross to nulli-tetrasomic line (e.g., N4DT4A) next to force pairing with normal 4D chromosome (see also Example 3.3).

Example 3.2 ph1b Induced Homoeologous Pairing Approach Encouraged by Translocation of Small *Agropyron* Segment onto Wheat Alternatively or additionally to Example 3.1, a proportion of *Agropyron chromatin* not carrying a gene for blue seed colour can be translocated onto a wheat chromosome; 4A, 4B, 4D or 5A. In this case, wheat-agropyron chromosome will pair with the intact Bla-chromosome (FIG. 4; lower panel).

The resulting chromosome from a translocation of *Agropyron chromatin* (4AgL—*Agropyron elongatum*) to a wheat chromosome 4 (4Ta—*Triticum aestivum*) can be designated as:

4AgL-4TaL.4TaS

This chromosome would pair with the intact Bla-chromosome to give an open bivalent association. The 4B chromosome for example would carry the gene for male sterility or lacks the gene for male fertility ('Probus' deletion). The possible and preferred outcomes are:

Translocation onto chromosome 4A:
Chromosome 1=4AgL-4AL.4AS
Chromosome 2=4AgL(blue)-4BoL.4BoS(fertility restorer), or 4AgL(blue)-4BL.4BoS(fertility restorer)
Translocation onto chromosome 4B (see FIG. 15):
Chromosome 1=4AgL-4BL.4BS(deletion)
Chromosome 2=4AgL(blue)-4BoL.4BoS(fertility restorer) 4AgL(blue)-4BL.4BoS(fertility restorer)
Translocation onto chromosome 4D:
Chromosome 1=4AgL-4DL.4DS
Chromosome 2=4AgL(blue)-4BoL.4BoS(fertility restorer) 4AgL(blue)-4BL.4BoS(fertility restorer)

Presumed 42 chromosome lines will be tested cytologically to identify the location of translocation. Lines which exhibit translocation of a small agropyron chromatin segment onto a wheat chromosome will be selected for further testing and crossing with normal Ph1 with the msms deletion.

Example 3.3

Figure 16A:
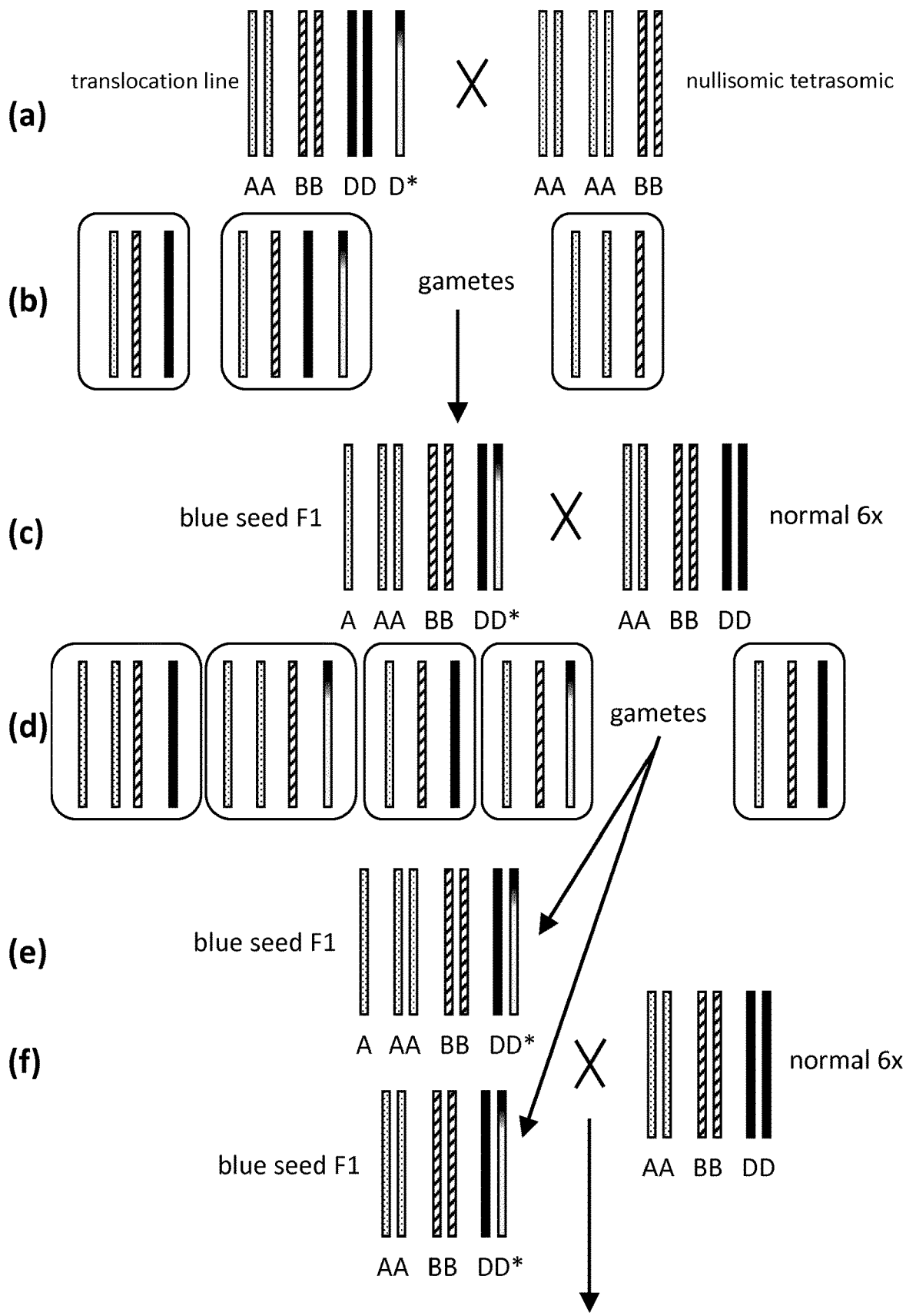
Figure 16B:
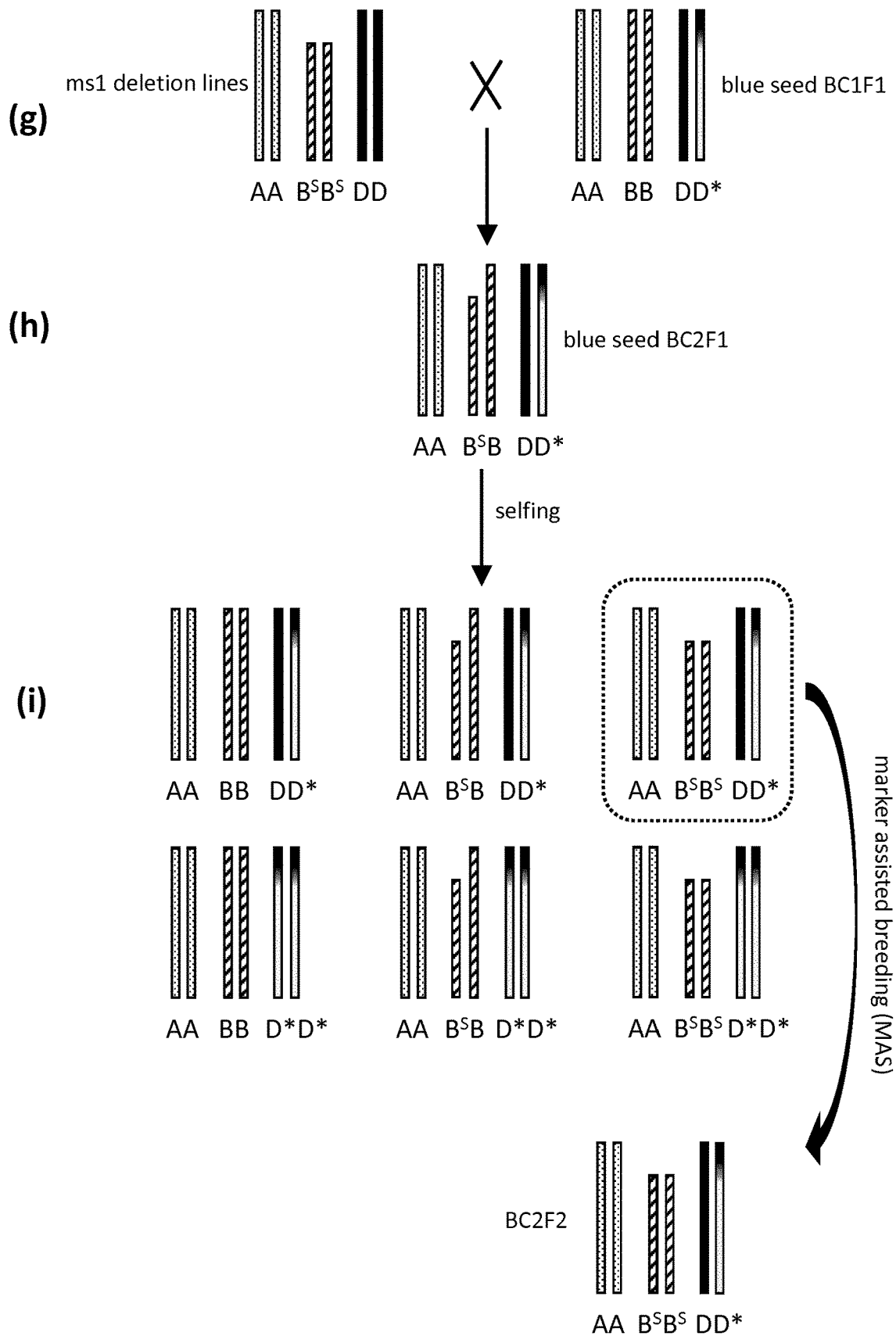

Transferring a New Translocation Chromosome into 42-Chromosome Background Via Crossing with Nullisomic Tetrasomic Lines Any above described successful translocation made for a 42-chromosome system will subsequently need to go through a series of crosses to eliminate all unwanted translocations and extra chromosomes to finally achieve a 42-chromosome Bla-line. One crucial step will be to force the pairing of a translocated chromosome with a *T. aestivum* chromosome in the case of Ta-4AgL(blue)-4BoL.4BoS(fertility restorer) or Ta-4AgL(blue)-4BL.4BoS(fertility restorer), or with the original Bla-chromosome in the case of 4AgL-TaL.TaS. This forcing of pairing can be achieved via crossing with nullisomic-tetrasomic line missing the corresponding chromosome pair where the new translocation is made (FIG. 16A-C).

Such transferring process is exemplified for 4AgL(blue)-4BoL.4BoS(fertility restorer)-4DS (denoted as D*). However can be applied also in case of 4AgL(blue)-4BL.4BoS (fertility restorer)-4DS. In step I the translocation line containing beside a normal set of bivalent chromosomes (AA-BB-DD) the monovalent D* is crossed with nullisomic tetrasomic Chinese spring wheat carrying two A genomes and one B genome (AA-AA-BB) but no D genome. F1 blue seeds (A-AA-BB-DD*) are selected and crossed with normal wheat (AA-BB-DD) in step II. From the four types of gametes two combinations results in blue seeds exhibiting chromosome compositions A-AA-BB-DD* and AA-BB-DD*, whereby by using qPCR lines with the extra A chromosome are eliminated. Alternatively, this elimination can also be performed by means of a flow cytometer. In step III plants obtained from the selected blue seeds (AA-BB-DD*) are backcrossed with normal wheat (elite material) to produce BC1F1 blue seeds (BC1: backcross 1, filial generation 1). These plants obtained from these blue seeds are crossed with ms1 deletion lines carrying homozygously the Probus deletion (AA-$B^sB^s$-DD) and BC2F1 blue seeds are selected in step IV. After selfing the plants generated from the selected blue seeds of step IV progeny with (AA-$B^sB^s$-DD*) are selected for instances by using KASP marker technology in step V. A final selfing (step VI) results in three types of progeny:

Single blue (light blue) fertile (AA-$B^sB^s$-DD*)
Double blue (dark blue) fertile (AA-$B^sB^s$-DD*)
White sterile (AA-$B^sB^s$-DD).

Such system in place is segrating 1:2:1 (double blue: single blue:white). White seeds can be used in hybrid testcross production, single blue seed can be used for generation more white seeds or for breeding pool development and double blue seeds should be discarded.

Example 4

Random Integration of Blue Aleurone (bla) and Fertility Restorer (Rf) Gene Cassettes into the Wheat Genome To produce wheat plants with genetically linked bla and Rf gene cassettes, the bla and Rf genes, including the promoters and terminators (e.g., from 500 bp to 2.5 kb upstream and 300 bp to 1.5 kb downstream of the ORFs), are PCR-amplified from appropriate genotypes and cloned into a single plasmid using standard molecular biology techniques. The gene cassettes can be arranged in any configuration, including "head-to-head", "tail-to-tail", "tail-to-head", or "head-to-tail". The gene cassettes are thereby fused into a single molecule with only a short DNA sequence between them. In the plant genome, this close proximity arrangement results in a situation of genetic linkage between the two genes and, therefore, the blue aleurone and male-fertile phenotypes will typically inherit together.

Once arranged in close proximity in a plasmid, the linked gene cassettes can be delivered into wheat cells in several ways, such as, but not limited to:

*Agrobacterium*-mediated transformation of the genes harbored within T-DNA borders in a binary plasmid
Particle bombardment of a plasmid in supercoiled, circular, relaxed, or linear configurations
Particle bombardment of a PCR-amplicon of the linked cassettes, thereby resulting in introduction only of DNA that is already present in the wheat plants harboring 43 chromosomes (no introduction of DNA that does not already exist in plants made through sexual crosses)
Other forms of transformation used in the field The type of cells treated in this way can be from any genotype amenable to the transformation method used. The type of tissue treated can be immature embryos or callus if the method is in vitro transformation and regeneration. Or it can be whole or partially dissected embryos in which the meristem is bombarded directly and the embryo germinated to produce plants. The transformation protocol can include a marker gene cassette or not.

In one scenario cells are transformed from a male-sterile genotype and regenerate or germinate without selection, then use the male-fertile and blue-aleurone phenotypes to identify plants with both genes integrated in a location they are properly expressed.

Thereafter, an "elite event" is identified, which is typically characterized by having a single-copy insertion in a preferred location of the genome that doesn't disrupt a native gene sequence and allows adequate expression of the genes stable over generations. qPCR is typically used to identify single-copy events in the first generation.

Example 5

Targeted Integration of Bla and Rf Gene Cassettes into the Wheat Genome

To produce wheat plants with genetically linked bla and Rf gene cassettes integrated into a targeted location within the wheat genome, a procedure is used like the one described in Example 4, with the following differences:

A target location within the wheat genome is selected that enables good transgene expression, does not disrupt native genes, and has favorable characteristics for breeding. A site-specific nuclease such as a meganuclease, a TALEN, a ZFN, or a CRISPR nuclease is designed to make a double-stranded break at the target site. The nuclease can be delivered by transformation of DNA cassettes encoding the necessary gene(s), by transformation of RNA molecules, or by transformation of purified protein or ribonucleoprotein complexes.

The double strand break (DSB) induced by the site-specific nuclease (SSN) is the site at which the bla and Rf gene cassettes are integrated into the wheat genome. The integration strategy can be by non-homologous end-joining (NHEJ), in which the DNA molecule harboring the bla and Rf gene cassettes is ligated by the cellular machinery into the DSB. In this case, no homology arms are required. In one instance, one would transform a linear PCR-amplicon consisting only of the cassettes. In another instance, it is possible to set up the plasmid in a way that the SSN cleaves the cassettes out of the plasmid in addition to inducing the genomic DSB. An alternative integration strategy is to flank the bla and Rf gene cassettes with upstream and downstream homology arms, so as to integrate the cassettes into the site of the DSB by homologous recombination.

Example 6

Targeted Integration of Bla Gene Cassette Near the Rf Gene Cassette on the 43rd Chromosome To produce wheat plants with the bla gene cassette near the Rf gene cassette in a targeted location within the $43^{rd}$ chromosome, a procedure is used like the one described in Example 5, with the following differences:

Instead of cloning both gene cassettes into the plasmid, only the bla gene cassette is cloned. The SSN is targeted to a site near the Rf gene cassette on the $43^{rd}$ chromosome. If the bla gene cassette is integrated by homologous recombination, the homology arms flanking the bla cassette are designed appropriately.

Any suitable genotype for the modification and the transformation procedure can be used. For example, one can have a genotype with a $43^{rd}$ chromosome lacking the bla gene, so that the blue aleurone phenotype can be used as an indicator of modified plants.

Example 7

Targeted Integration of Rf Gene Near the Bla Gene Cassette on the 43rd Chromosome To produce wheat plants with the Rf gene cassette near the bla gene cassette in a targeted location within the $43^{rd}$ chromosome, a procedure is used like the one described in Example 5, with the following differences:

Instead of cloning both gene cassettes into the plasmid, only the Rf gene cassette is cloned. The SSN is targeted to a site near the bla gene cassette on the $43^{rd}$ chromosome. If the Rf gene cassette is integrated by homologous recombination, the homology arms flanking the Rf cassette are designed appropriately.

Any suitable genotype for the modification and the transformation procedure can be used. For example, one can have a genotype with a $43^{rd}$ chromosome lacking the Rf gene, so that the male-fertile phenotype can be used as an indicator of modified plants.

Example 8

Nuclease-Induced Rearrangement of the 43rd Chromosome Resulting in Genetic Linkage of the Bla Gene Cassette with Rf Gene Cassette To produce wheat plants with genetically linked bla and Rf genes by nuclease-induced rearrangement of the $43^{rd}$ chromosome, only SSNs are delivered to the cells harboring the $43^{rd}$ chromosome with both genes on it. At least two SSNs are necessary, but more can be used to further fragment the $43^{rd}$ chromosome. In a preferred embodiment, one nuclease is targeted shortly outside (toward the end of the chromosome) one of the genes and the other nuclease is targeted just inside (toward the centromere) the other gene. By breaking both ends of the chromosome simultaneously, or in close sequence, the desired outcome is that the chromosome ends will be swapped so that the bla and Rf genes are thereby in close proximity to each other on one arm of the $43^{rd}$ chromosome.

Due to the cost of generating transgenic plants, it is potentially desirable to generate a wheat line expressing the active nucleases and cross it with a line harboring the $43^{rd}$ chromosome, thereby bringing the nucleases into contact with their target sites by breeding. In this many thousands of independent plants, each with a potential rearrangement event, can be generated.

Because the rearrangement is very precise, the desired outcome is known, and primers can be designed that span the junction of the preferred fusion. Thereby, hundreds or thousands of primary and later generation plants can be screened to find one with the correct rearrangement.

Example 9

Alien Introgression Tool

A BLA-system (either 42 or 42+1 chromosome based) with the ph1b mutant and with crossable genes facilitating crosses to wheat alien species could be used to transfer genes from alien species into wheat. White seed from such crosses would be sterile amphihaploids and would cross with a regular wheat. From such crosses, fertile, normal Ph1 lines carrying novel translocation could be selected.

Example 10

Novel Triticale Lines

White seed male sterile BLA lines that are crossable with rye will be identified. If any of these BLA lines are crossable with rye, we should then be able to cross the same lines (fertile blue seed lines) with rye to obtain blue seed wheat-rye amphihaploids. This technique can generate new secondary blue seed triticales. It is also possible to make direct crosses between hexaploid triticale and Bla wheat with subsequent selection of AABBRR progeny following selfing and screening for the system components

Example 11

Recurrent Selection

BLA can be used to facilitate recombination in recurrent selection programs. A series of females are converted to BLA on the basis of prior Quantitative Trait Loci (QTL)/genome-wide association study. These females will carry key regions of interest for selection. The males will be identified based on complementary markers in the upper end of the distribution of progeny based on phenotypic analysis. These males are crossed as a pollen bulk to several females and the resulting seed grown and self-fertilized. At the same time, these plants are screened for markers using a Kompetitive Allele Specific PCR (KASP) assay to identify those for the second round of recombination.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A cereal plant for use in the production of hybrid cereal plants, wherein the cereal plant comprises at least one homoeologous chromosome pair, wherein the pair consists of a first and second chromosome,
wherein the first chromosome is native to the cereal plant and the second chromosome comprises an alien chromosome fragment comprising a dominant male fertility restorer gene and at least one selection marker gene on the same side of a centromere of the second chromosome,
wherein the cereal plant comprises a male fertility gene mutation causing male sterility,
wherein the at least one selection marker gene is non-transgenic,
wherein the male fertility restorer gene is from *Triticum boeoticum* or *Triticum monococcum* and comprises a nucleic acid sequence selected from the group consisting of:
(i) a nucleic acid sequence as set forth in SEQ ID NO: 1, 6, 7, 8, or 10, or fragments or variants thereof that produce functional amino acid sequences;
(ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences;
(iii) a nucleic acid sequence having a coding sequence as set forth in SEQ ID NO: 2, 4, 9, 11, or 14, or fragments or variants thereof that produce functional amino acid sequences;
(iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences;
(v) a nucleic acid sequence encoding an amino acid sequence as set forth in SEQ ID NO: 3, 5, 15, 42, or 43, or fragments or variants thereof that produce functional amino acid sequences; and
(vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof, and
wherein the at least one selection marker gene is a blue aleurone gene, wherein the blue aleurone gene is from *Agropyron elongatum*, *Agropyron trichophorum*, or *Triticum monococcum*, and wherein the blue aleurone gene comprises a nucleic acid sequence selected from the group consisting of:
(i) a nucleic acid sequence having a coding sequence of SEQ ID NO: 44 or 12, or fragments or variants thereof that produce functional amino acid sequences;
(ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences;
(iii) a nucleic acid sequence encoding an amino acid sequence of SEQ ID NO: 45 or 13, or fragments or variants thereof that produce functional amino acid sequences; and
(iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

2. The cereal plant of claim 1, wherein the first chromosome comprises a piece of chromatin of *Agropyron elongatum* as a translocation, preferably onto the end of the long arm of the first chromosome, wherein said piece of chromatin pairs to the alien chromosome fragment or a part thereof, and/or the second chromosome further comprises native DNA.

3. The cereal plant of claim 1, wherein the cereal plant consists of a euploid number of chromosomes.

4. The cereal plant of claim 1, wherein the cereal plant is a tetraploid wheat, a hexaploid wheat, triticale, maize, rice, barley, or oats.

5. The cereal plant of claim 1, wherein the cereal plant comprises a mutated homoeologous pairing suppressor gene, preferably wherein the homoeologous pairing suppressor gene is deleted.

6. The cereal plant of claim 1, wherein the mutated homoeologous pairing suppressor gene is ph1b or ph2.

7. The cereal plant of claim 1, wherein the cereal plant comprises homozygously a male fertility gene mutation that is a gene deletion, a gene knockdown, or a gene knockout, preferably wherein the male fertility gene is Ms1 or a nucleic acid comprising a nucleic acid sequence selected from the group consisting of:
  (i) a nucleic acid sequence as set forth in SEQ ID NO: 1, 6, 7, 8, or 10, or fragments or variants thereof that produce functional amino acid sequences;
  (ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences;
  (iii) a nucleic acid sequence having a coding sequence as set forth in SEQ ID NO: 2, 4, 9, 11, or 14, or fragments or variants thereof that produce functional amino acid sequences;
  (iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences;
  (v) a nucleic acid sequence encoding an amino acid sequence as set forth in SEQ ID NO: 3, 5, 15, 42, or 43, or fragments or variants thereof that produce functional amino acid sequences;
  (vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

8. Seed, progeny or a part thereof of the cereal plant of claim 1, wherein the seed, progeny, or part thereof comprises the dominant male fertility restorer gene and the selection marker gene on the same side of the centromere of the second chromosome.

9. A method of generating a blue aleurone (BLA) male sterile system for genomic selection of cereal plants comprising:
  a) selecting a cereal plant line homozygous for a male fertility gene mutation comprising at least one alien addition chromosome carrying a male fertility restorer gene as defined in claim 1 and a non-transgenic blue aleurone gene on different sides of the centromere of the at least one alien addition chromosome;
  b) rearranging the male fertility restorer gene and the non-transgenic blue aleurone gene on the same side of a centromere of the at least one alien addition chromosome;
  c) inducing homoeologous recombination of at least one alien addition chromosome; and
  d) obtaining a cereal plant comprising a homoeologous alien addition chromosome, wherein the non-transgenic blue aleurone gene is from *Agropyron elongatum, Agropyron trichophorum*, or *Triticum monococcum*, and more preferably wherein the non-transgenic blue aleurone gene comprises a nucleic acid sequence selected from the group consisting of:
  (i) a nucleic acid sequence having a coding sequence of SEQ ID NO: 44 or 12, or fragments or variants thereof that produce functional amino acid sequences;
  (ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences;
  (iii) a nucleic acid sequence encoding an amino acid sequence of SEQ ID NO: 45 or 13, or fragments or variants thereof that produce functional amino acid sequences; and
  (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

10. The method of claim 9, wherein the alien addition chromosome is monosomic or disomic.

11. The method of claim 9, wherein the inducing homoeologous recombination step c) comprises the presence of a mutated homoeologous pairing suppressor gene or introducing a gene which suppresses the homoeologous pairing suppressor gene, wherein the homoeologous pairing suppressor gene induces the homoeologous recombination of the alien addition chromosome comprising the dominant male fertility restorer gene and at least one selection marker, with at least one homoeologous chromosome.

12. A cereal plant or part thereof, wherein the cereal plant is obtained from step c) of claim 9, and wherein the cereal plant does not comprise a mis-division of the alien addition chromosome or the cereal plant does not comprise a breakage of the alien addition chromosome.

13. A method of generating a blue aleurone (BLA) male sterile system for genomic selection of cereal plants comprising:
  a) selecting a cereal plant line homozygous for a male fertility gene mutation;
  b) integrating into the genome of the cereal plant line a male fertility restorer gene and a non-transgenic blue aleurone gene, wherein the male fertility restorer gene as defined in claim 1 and the non-transgenic blue aleurone gene are genetically linked and in close proximity on the same side of the centromere of the second chromosome; and
  c) obtaining a cereal plant comprising the genetically linked male fertility restorer gene and non-transgenic blue aleurone gene,
wherein the non-transgenic blue aleurone gene is from *Agropyron elongatum, Agropyron trichophorum*, or *Triticum monococcum*, and more preferably wherein the non-transgenic blue aleurone gene comprises a nucleic acid sequence selected from the group consisting of:
  d) a nucleic acid sequence having a coding sequence of SEQ ID NO: 44 or 12, or fragments or variants thereof that produce functional amino acid sequences;
  e) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences;

f) a nucleic acid sequence encoding an amino acid sequence of SEQ ID NO: 45 or 13, or fragments or variants thereof that produce functional amino acid sequences;

g) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof.

14. The method of claim 13, wherein the male fertility restorer gene and the blue aleurone gene are introduced into a cell of the cereal plant line via a gene cassette.

15. The method of claim 13, wherein the male fertility restorer gene and the blue aleurone gene are linked via a linker.

16. The method of claim 14, wherein the gene cassette is introduced into the cell by *Agrobacterium*-mediated transformation of the male fertility restorer gene and blue aleurone gene harbored within T-DNA borders in a binary plasmid, or by particle bombardment of a plasmid comprising the gene cassette in supercoiled, circular, relaxed, or linear configurations.

17. The method of claim 13, wherein the integrating step b) comprises targeting the integration of the linked male fertility restorer gene and blue aleurone gene using a site-specific nuclease designed to make a double-strand break at a target site in the cereal plant line genome and wherein the linked male fertility restorer gene and blue aleurone gene is integrated into the cereal plant line genome at the site of the double-strand break.

18. A cereal plant or part thereof, wherein the cereal plant is obtained from step c) of claim 13, and wherein the cereal plant comprises a single-copy insertion of the linked male fertility restorer gene and blue aleurone gene.

19. A method for the maintenance of a male-sterile female parental line of a cereal plant for use in the production of hybrid cereal plants, the method comprising:

a. planting at least one seed comprising a homozygous male fertility gene mutation and at least one portion of an alien addition chromosome carrying a dominant male fertility restorer gene as defined in claim 1 and at least one non-transgenic selection marker gene translocated into at least one chromosome of a homoeologous chromosome pair, the dominant male fertility restorer gene and the at least one non-transgenic selection marker gene being located on the same side of a centromere of the at least one chromosome;

b. self-fertilizing a cereal plant produced in step a);

c. selecting at least one seed not comprising the alien addition chromosome translocated into at least one chromosome of a homoeologous chromosome pair for growing at least one sterile-female parent cereal plant for crossing with a fertile-male cereal plant for a hybrid cereal plant and a hybrid seed production;

d. selecting at least one seed comprising the alien addition chromosome translocated into one chromosome of a homoeologous chromosome pair for maintenance of the cereal plant, wherein the seed is heterozygous for the translocation as preferably indicated by the expression of the at least one non-transgenic selection marker gene; and e. discarding any seed comprising the alien addition chromosome translocated into at least two chromosomes of a homoeologous chromosome pair for maintenance of the cereal plant, wherein the seed is homozygous for the translocation as preferably indicated by expression of the at least one non-transgenic selection marker gene, wherein the at least one non-transgenic selection marker gene is a blue aleurone gene, preferably wherein the blue aleurone gene is from *Agropyron elongatum, Agropyron trichophorum*, or *Triticum monococcum*, and more preferably wherein the blue aleurone gene comprises a nucleic acid sequence selected from the group consisting of:

(i) a nucleic acid sequence having a coding sequence of SEQ ID NO: 44 or 12, or fragments or variants thereof that produce functional amino acid sequences;

(ii) a nucleic acid sequence having a coding sequence with at least 80%, at least 85%, at least 90%, at least 95%, at least 96%, at least 97%, at least 98%, or at least 99% sequence identity to the nucleic acid sequence of SEQ ID NO: 44 or 12, or fragments thereof that produce functional amino acid sequences; and (iii) a nucleic acid sequence encoding an amino acid sequence of SEQ ID NO: 45 or 13, or fragments or variants thereof that produce functional amino acid sequences; and (iv) a nucleic acid sequence encoding an amino acid sequence with at least 80%, at least 85%, at least 90%, at least 95%, at least 96%, at least 97%, at least 98%, or at least 99% sequence identity to the amino acid sequence of SEQ ID NO: 45 or 13, or fragments thereof, and wherein the homozygously a male fertility gene mutation, which is a gene deletion, a gene knockdown, or a gene knockout, preferably wherein the male fertility gene is Ms1 or a nucleic acid comprising a nucleic acid sequence selected from the group consisting of:

(i) a nucleic acid sequence as set forth in SEQ ID NO: 1, 6, 7, 8, or 10, or fragments or variants thereof that produce functional amino acid sequences;

(ii) a nucleic acid sequence with at least 80%, at least 85%, at least 90%, at least 95%, at least 96%, at least 97%, at least 98%, or at least 99% sequence identity to the nucleic acid sequence as set forth in SEQ ID NO: 1, 6, 7, 8, or 10, or fragments thereof that produce functional amino acid sequences;

(iii) a nucleic acid sequence having a coding sequence as set forth in SEQ ID NO: 2, 4, 9, 11, or 14, or fragments or variants thereof that produce functional amino acid sequences;

(iv) a nucleic acid sequence having a coding sequence with at least 80%, at least 85%, at least 90%, at least 95%, at least 96%, at least 97%, at least 98%, or at least 99% sequence identity to the nucleic acid sequence as set forth in SEQ ID NO: 2, 4, 9, 11, or 14, or fragments thereof that produce functional amino acid sequences;

(v) a nucleic acid sequence encoding an amino acid sequence as set forth in SEQ ID NO: 3, 5, 15, 42, or 43, or fragments or variants thereof that produce functional amino acid sequences;

(vi) a nucleic acid sequence encoding an amino acid sequence with at least 80%, at least 85%, at least 90%, at least 95%, at least 96%, at least 97%, at least 98%, or at least 99% sequence identity to the amino acid sequence as set forth in SEQ ID NO: 3, 5, 15, 42, or 43, or fragments thereof.

20. A cereal plant or part thereof produced by the method of claim 19.

* * * * *

SEQUENCE LISTING

```
<160> NUMBER OF SEQ ID NOS: 45

<210> SEQ ID NO 1
<211> LENGTH: 3838
<212> TYPE: DNA
<213> ORGANISM: Hordeum vulgare

<400> SEQUENCE: 1
cgcacatcaa cataaactca tcagatggga ataatcggat ctacgaagga cataaaactc      60
tttaatctca tgacaacgcc agaagagcaa gagtaaatat attctcataa aaaacaatga     120
acactagatg atgacgaaga acataagatt cttcaaggag aaattgcggc agcggagatg     180
gcagccggag gcgagggggc caaaaactct gttgcggcgg cagcggtagc cttggtgaaa     240
cccacacgtt tgcacaccat ataagttgtt tgcaagggtt acatgggcct cgctctcgtg     300 aaaagaagg tcatacatgg gtcttggtct cgtgcaaaac gaaaggtcag cagtccatgg      360
gccggaggaa aaaccgggca acaacacgcc atgtgtgttt tcgcgggaac ccaattccga     420
aatcactcac cggcacctcg tcccgatgcc ttccagaacg ttctacgtgc ttccacaggg     480
ccagcccagc cgtgggatca gatcaggatc agcacgaaca ttgaagctag cgcggcgata     540
tttttcccag cctccgcctc gctcgacgac tgcatttcat ttcgaaaaca aaaaaaagag     600
ctttctcctt ctcatcccga gcgccagagg agcaccagaa aggccaccca cccaccctca     660
cgtaccgccc tcgcacccgc gcggccacat ctgggccgtc cacttgggca gctggccgtt     720
ccattcccga actgacgggc aggatcgagc gagcggcgcg cccacggctc ctccggctat     780
ataacccgcc acccacacca ctcccctccg gcgttccacc agagccttcc tccctccacc     840
gcaccaccac caccaccgcg ccaaaaaccc tagggagcga gcgagctcac ctcgccccgc     900
ccatggagag atcccgccgc ctgctgctcg tggcggggct cctcgccgcg ctgctcccgg     960
cggcggccgc caccttcggg ctgcagcagg gggcgcagtg cgacccacg ttcctggcga    1020 cgcaggccgc gctcttctgc gcccccgaca tgcccacggc ccagtgctgc gagcccgtcg    1080
tcgccgcctt cgacctcggg ggcggcgtcc cctgcctctg ccgcgtcgcc gccgagccgc    1140
agctggtcat ggcggggctc aacgccaccc acctcttcgc gctgtacacc tcctgcggcg    1200
gcatccgtcc cggtggcgcc cacctcgccg ccgcctgcca aggtacgttc acgttcaccg    1260
cctccctccc tctccttctc tctttgcacc tgtaccagcc gattcggcgt tcgctttcgc    1320
```

```
gtttcccggt agttttgatg gtttctcgag tcgccagtgc tccgatttgg gttcggtttc    1380
cttgcgttgt accggatctg cctgtacggc gcgcggcgtc ggggtctccg ttgtttcccg    1440
tggcgagcat ccccgcgcgc ccacggccta gctagcttac cttcagatac gcggagcgat    1500
ttaggatcag tatgaggagt tcgtcgtaga agaatgcatg cggaacgcgc gattgtttgt    1560
ttcatcgatt ttggatctgt gataggcctg cttgttcccg agttttttgca cgtagaagaa    1620 tcatgtgcag aaccccctggt ccattatttg ttatgtatat acacgattac ttgtgcatat    1680
gcagaagtct tagttatctg ctacccttcc agaattattc gtggtgtttt tgttcctcta    1740
gttaaacttc agatgatctt tcgttcgagt ttattttcct gcctgtaact gagatcgata    1800
tacctatcac cgtgactgtg agagagacag agagttgttg ccgtttaact gctatatata    1860
tgtacgtttt ctgctactgt ttaatcgact gctccatccc gttcgcgata ggacttgttt    1920
caaaccgtca cgcagctctg cttcctgcag tgtcttttgt cttcgtttgg tcaaaactga    1980
aaacgcttgc tatcgaggcc agaggcaggg caaaagctcc ccgtactttt cgctttgcag    2040
tggcatctct ttctttttt ttgccgaaaa ttgtttccac gttcatcccc gggtgtcgta    2100
ctacttaatt atctgcatgc agttttcgtg tccttcctcc gtcgtgaaaa aaaggttggg    2160
tcaaatgaat caaccgtgta tgcagggcag cagcaacaga gatagagtag ctggctgtcg    2220
cagctttaac aaaagcagtc tgtggcctgc cacagttttc ctgattttg tttaatctgg    2280 cctgggcttc ttttcttgtt gcgcacgtcg tcgcctcctt ctttttccc aattttttga    2340 tttcttttga gataaggaca cgaacggctg gtaactgact tttcttgttg tttttttactg    2400 tgggttttgg acgcaggacc ggctcccccg gccgccgtcg tcagcagccc cccgccacca    2460
tcgccagcac ctcgccgcaa acaggcagcg cgtacgaacc tctcgctctc tctctctccc    2520
tctcgcctgc atctcgctct gtacataacc tattgggttc atatgctgat cagcgttgac    2580
atactaactt gttcatttga ttctcagacg acgcgcctcc accgccgccg tccagcgaga    2640
agccatcccc gccgcccag gagcatgacg gcgccgcaca cgccaagagc gcccccgccc    2700
tcgcggctcc taccccgctc gcgcccgctg ccgctactgc cccgccgccc gaggcgccac    2760
actccgccgc gtcgtcgtcc gattcggcct tcatcttcat cgccgcggcc atgctcgcca    2820
tttacatcgt cctctgaatg gccgaccccc aaggcagcag agtacttgtc atctgattcc    2880
gtttcatgct tgtcgccgtt tgttgaggtt cgtttctgca gtccgaacaa gacggtgggg    2940
ttttgatcgg gtacccagat ttctatgtcg atcgcgcgta ctagtactag tagttgctta    3000
gcagatgaac gaacattggg ttttgggatt cctctagctg atgaaccact gctatttttcc    3060 atgtgatcga tggatatgat ctgaatggat ggatgaagtt ttggtttctg atgctgatga    3120
tgtgctgctt cttcatttgc atgctcgatc tattccttca attttgtgga gcaacagttt    3180
gtttagcttc tgttctgcta tgaataatgc cgcttgcatc ttgtcattgc tgataatctg    3240
cttaatgcag acattgcttc cgtcccaaac aatctgttgc ttaccaggta atgcatataa    3300
tctgtacctc accttcgcac aacaacagaa gctaccctgc taaaaaaaca cacacacaca    3360
cacaaaaaaa acagaagctg gtctcacacg gaagccgctt cggggactgt ttgcagcttt    3420
ttattgccat tttgttttttc atgcaggtac aaatcgaggg tgttgcttga tttgatcatg    3480
gatgatcact tagagcaaca tgtgtgtttt gtctgtgttt tattcgttgc tcgtccatcc    3540
aatttaaact tgaaatggat cgtgtgtgga taaaagaaga cgtgcgtcag tttgaatcga    3600
cgcgttgggt tatattttgt gtctgtgacg accgaaacga agacaaaata tatcgtccgg    3660
```
ttagaattgc tctaatgcta gctttctctc ctaccatcgc attccgtggt aggaaaaagt    3720
actagaacca caggaaactg aaacgcaaga aaagcatatc taccgttggc cgttgatctt    3780
gtttcacatt cggtatggct ccggtcatat tgttggagat tcacattcat gcacgcaa     3838

<210> SEQ ID NO 2
<211> LENGTH: 645
<212> TYPE: DNA
<213> ORGANISM: Artificial Sequence
<220> FEATURE:
<223> OTHER INFORMATION: cDNA of HvMs1

<400> SEQUENCE: 2
atggagagat cccgccgcct gctgctcgtg gcggggctcc tcgccgcgct gctcccggcg     60
gcggccgcca ccttcgggct gcagcagggg gcgcagtgcg accccacgtt cctggcgacg    120
caggccgcgc tcttctgcgc ccccgacatg cccacggccc agtgctgcga gcccgtcgtc    180
gccgccttcg acctcggggg cggcgtcccc tgcctctgcc gcgtcgccgc cgagccgcag    240
ctggtcatgg cggggctcaa cgccacccac ctcttcgcgc tgtacacctc ctgcggcggc    300
atccgtcccg gtggcgccca cctcgccgcc gcctgccaag gaccggctcc ccggccgcc     360 gtcgtcagca gcccccccgcc accatcgcca gcacctcgcc gcaaacaggc agcgcacgac    420
gcgcctccac cgccgccgtc cagcgagaag ccatccccgc cgccccagga gcatgacggc    480
gccgcacacg ccaagagcgc ccccgccctc gcggctccta ccccgctcgc gcccgctgcc    540
gctactgccc cgccgcccga ggcgccacac tccgccgcgt cgtcgtccga ttcggccttc    600
atcttcatcg ccgcggccat gctcgccatt tacatcgtcc tctga                    645

<210> SEQ ID NO 3
<211> LENGTH: 214
<212> TYPE: PRT
<213> ORGANISM: Hordeum vulgare

<400> SEQUENCE: 3

Met Glu Arg Ser Arg Arg Leu Leu Leu Val Ala Gly Leu Leu Ala Ala
1               5                   10                  15

Leu Leu Pro Ala Ala Ala Ala Thr Phe Gly Leu Gln Gln Gly Ala Gln
            20                  25                  30

Cys Asp Pro Thr Phe Leu Ala Thr Gln Ala Ala Leu Phe Cys Ala Pro
        35                  40                  45

Asp Met Pro Thr Ala Gln Cys Cys Glu Pro Val Val Ala Ala Phe Asp
    50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Phe Ala Leu Tyr Thr
                85                  90                  95

Ser Cys Gly Gly Ile Arg Pro Gly Gly Ala His Leu Ala Ala Ala Cys
            100                 105                 110

Gln Gly Pro Ala Pro Ala Ala Val Val Ser Pro Pro Pro
            115                 120                 125

Ser Pro Ala Pro Arg Arg Lys Gln Ala Ala His Asp Ala Pro Pro
        130                 135                 140

Pro Pro Ser Ser Glu Lys Pro Ser Pro Pro Gln Glu His Asp Gly
145                 150                 155                 160

Ala Ala His Ala Lys Ser Ala Pro Ala Leu Ala Pro Thr Pro Leu
                165                 170                 175

```
Ala Pro Ala Ala Ala Thr Ala Pro Pro Glu Ala Pro His Ser Ala
            180                 185                 190

Ala Ser Ser Ser Asp Ser Ala Phe Ile Phe Ile Ala Ala Ala Met Leu
        195                 200                 205

Ala Ile Tyr Ile Val Leu
        210

<210> SEQ ID NO 4
<211> LENGTH: 663
<212> TYPE: DNA
<213> ORGANISM: Artificial Sequence
<220> FEATURE:
<223> OTHER INFORMATION: cDNA of TaMs1

<400> SEQUENCE: 4
atggagagat cccgcgggct gctgctggtg gcggggctgc tggcggcgct gctgccggcg      60
gcggcggcgc agccggggc gccgtgcgag cccgcgctgc tggcgacgca ggtggcgctc     120
ttctgcgcgc ccgacatgcc gacgcccag tgctgcgagc ccgtcgtcgc cgccgtcgac     180
ctcggcggcg gggtgccctg cctctgccgc gtcgccgccg agccgcagct cgtcatggcg     240
ggcctcaacg ccacccacct cctcacgctc tacagctcct gcggcggcct ccgcccggc     300 ggcgcccacc tcgccgccgc ctgcgaagga cccgctcccc cggccgccgt cgtcagcagc     360
ccccccgccc cgcctccacc gtccgccgca cctcgccgca agcagccagc gcacgacgca     420
ccaccgccgc caccgccgtc gagcgagaag ccgtcgtccc cgccgccgtc ccaggaccac     480
gacggcgccg ccccccgcgc caaggccgcg cccgcccagg cggccacctc cacgctcgcg     540
cccgccgccg ccgccaccgc cccgccgccc caggcgccgc actccgccgc gcccacggcg     600
ccgtccaagg cggccttctt cttcgtcgcc acggccatgc tcggcctcta catcatcctc     660
tga                                                                    663

<210> SEQ ID NO 5
<211> LENGTH: 220
<212> TYPE: PRT
<213> ORGANISM: Triticum aestivum

<400> SEQUENCE: 5

Met Glu Arg Ser Arg Gly Leu Leu Val Ala Gly Leu Leu Ala Ala
1               5                   10                  15

Leu Leu Pro Ala Ala Ala Gln Pro Gly Ala Pro Cys Glu Pro Ala
            20                  25                  30

Leu Leu Ala Thr Gln Val Ala Leu Phe Cys Ala Pro Asp Met Pro Thr
        35                  40                  45

Ala Gln Cys Cys Glu Pro Val Val Ala Val Asp Leu Gly Gly Gly
        50                  55                  60

Val Pro Cys Leu Cys Arg Val Ala Ala Glu Pro Gln Leu Val Met Ala
65                  70                  75                  80

Gly Leu Asn Ala Thr His Leu Leu Thr Leu Tyr Ser Ser Cys Gly Gly
                85                  90                  95

Leu Arg Pro Gly Gly Ala His Leu Ala Ala Ala Cys Glu Gly Pro Ala
            100                 105                 110

Pro Pro Ala Ala Val Val Ser Ser Pro Pro Pro Pro Pro Pro Ser
            115                 120                 125

Ala Ala Pro Arg Arg Lys Gln Pro Ala His Asp Ala Pro Pro Pro
            130                 135                 140

Pro Pro Ser Ser Glu Lys Pro Ser Ser Pro Pro Pro Ser Gln Asp His
```

```
                145                 150                 155                 160
Asp Gly Ala Ala Pro Arg Ala Lys Ala Ala Pro Ala Gln Ala Ala Thr
                    165                 170                 175

Ser Thr Leu Ala Pro Ala Ala Ala Thr Ala Pro Pro Pro Gln Ala
                180                 185                 190

Pro His Ser Ala Ala Pro Thr Ala Pro Ser Lys Ala Ala Phe Phe Phe
            195                 200                 205

Val Ala Thr Ala Met Leu Gly Leu Tyr Ile Ile Leu
        210                 215                 220

<210> SEQ ID NO 6
<211> LENGTH: 4335
<212> TYPE: DNA
<213> ORGANISM: Triticum aestivum

<400> SEQUENCE: 6
agacttaaac catttagtta caaatatcga tgcacacctt cggtggggcg ttgtgaaaaa      60
gcatgttttt tgggtcgaca agccccttt gcaacgtatc ctcttctaat cctattcaga     120
tcattaacat cataagctgc aattgacatg ctcttctgag gatcaggttc atgcaattaa     180
acatcataaa ctgcatcttt gatgtcatcc tttttcctata ttttttccag attattggct     240
tgcttcgttt tcaatatcag gttctatgat tcgacttctg ttgttgccag taataatttg     300
tagttgctgc ggaatatgaa ctcaaggaga gctgatggtg ctatgaagtt gatttgatgg     360
gaggttgttc tacacctgca cttgctgctc gacttaaata catgccttgg atttcttccc     420
agctctagta cataatattt ttcaaattaa tgttccacga cataaaattt aaatccacaa     480
acatattttt agtacatgaa caattttcta atatagggca acatttttc atatacaaac     540 cgatcatttt aatatatggt gaaaatcagt gtaatatatg ctgaaatgtt ttcaaataca     600
tattgaacat atttataata aatggtgaac attttttta ataattgatg accattttta     660
aaatgcatat tgaacatttt ataatataca ctgtacagtt ttataatat cgacgaacat     720 cttttggagt tctgaacatt tttttcaaaa acacaagcca ttttccagga agaatacaaa     780
tgcaaaagaa atgagatatc caaaaagcaa aaagaaaaa caaaacaaaa cagagaaacc     840
tacaggaaaa tccaaacaga aaaggcaaag aaagaacccg aactgggcca ggcaatgttt     900
ccaacggcct cgctcttcct gaacaagaag gccagtcagc ccatgggctg ctcccagtac     960
tcgggccccg ctgtggcagc acgccatgta atagttttcg cgggaatcca acgccgaaat    1020
cgcccgcagc gggaacccga cgtcggtctg gtgcgttctg gcgccttcca gaactctcca    1080
caggctcccg cagccgtccg atcagatcag cacgaagcac gaacattggc gcgcggcgat    1140
attttctttc ctcgcccgac gacggccgca ctgcatttca ttttgaattt caaaattcgg    1200
aaacggaaaa gctttctcgc atcccgaggc gaggcggtta cgggcgccag aggggccacc    1260
ccacccaccc accccccgccc tcacgtgccc cgcgcggccg catccgggcc gtccgcgcgg    1320
acagctggcc gcgcccagcc cgaaccgacg cccaggatcg agcgagggcg gcgcgcccgg    1380
ggcttggctt agcgtccacg ccacctccgg ctatataagc cgccccacac ccgctccccc    1440
tccggcattc cattccgcca ccgcaccacc accaccacca aaccctagcg agcgagcgag    1500
ggagagagag accgccccgc cgcgacgatg gagagatccc gcgggctgct gctggtggcg    1560
gggctgctgg cggcgctgct gccgcggcg gggcgcagc cggggcgcc gtgcgagccc    1620 gcgctgctgg cgacgcaggt ggcgctcttc tgcgcgcccg acatgccgac ggcccagtgc    1680
tgcgagcccg tcgtcgccgc cgtcgacctc ggcggcgggg tgccctgcct ctgccgcgtc    1740
```

```
gccgccgagc cgcagctcgt catggcgggc ctcaacgcca cccacctcct cacgctctac    1800
agctcctgcg gcggcctccg ccccggcggc gcccacctcg ccgccgcctg cgaaggtacg    1860
ttgtccgcct cctcccctcc ctccctccct ccctctctct ctacgtgctc gctttcctgc    1920
ttacctagta gtacgtagtt tcccatgcct tcttgactcg ctagaagtgc tccggtttgg    1980
gtctgttaat ttcctcgctg tactaccgga tctgtcgtcg gcacggcgcg cggcgtcggg    2040
tcctcgcctt ctcccgtggc gaccgacctg cgcagcgcgc gcgcggccta gctagcttca    2100
taccgctgta cctcgacata cacggagcga tctatggtct actctgagta tttcctcatc    2160
gtagaacgca tgcgccgctc gcgattgttt cgtcgattct agatccgtgc ttgttcccgc    2220
gagttagtat gcatctgcgt gcatatgccg tacgcacgca gatgcagagt ctgttgctcg    2280
agttatctac tgtcgttcgc tcgaccatat ttgcctgtta atttcctgtt catcgtgcat    2340
gcagtagtag tagccatgtc cacgccttct tgttttgagg cgatcatcgt cgagatccat    2400
ggctttgctt tctgcactat cttctgcctt gttttgttct ccgcagtacg tacgtcttgc    2460
ttggtcaaaa ctgaaaaacg ctttgctgtt tgtttgatcg gcaagagctg gccgtgcttt    2520
tggcaccgca gtgcgtcgcc tctgccgctt ttgcgaaaca tttccatgtt gatcctctgg    2580
cggaactact ttttcgcgtg cggtttgcgt ggccttcctc tctcgtgaaa agaggtcggg    2640
tcaaaccaaa tggatcgcct cttggcagag cagcggcagc agatagctgg ccgtctcgca    2700
gctttggcag aaccggtctg tggccatctg tcgccgcctg ccaccgtttc cctgatgttt    2760
gtttctctct cgcctgccac tgtttctttt cttgttgcgc acgtacgtcg tcacctcctc    2820 ctacttttttt gccagttttg tttacttttg atgaaatata cggatgaatc ggctggtgat    2880 taacttggc tgctgctgtt aattactgtg gattttggat gcaggacccg ctcccccggc    2940
cgccgtcgtc agcagccccc cgcccccgcc tccaccgtcc gccgcacctc gccgcaagca    3000
gccagcgcgt aagaacctct ccctctccct ctctctctcc ctctcgcctg catctcgcta    3060
tgtttatcca tgtccatatg ttgatcagcc ttgtttagtt actaacatgt gcaccggatc    3120
gggttctcgc agacgacgca ccaccgccgc caccgccgtc gagcgagaag ccgtcgtccc    3180
cgccgccgtc ccaggaccac gacggcgccg cccccccgcg caaggccgcg cccgcccagg    3240
cggccacctc cacgctcgcg cccgccgccg ccgccaccgc cccgccgccc caggcgccgc    3300
actccgccgc gcccacggcg ccgtccaagg cggccttctt cttcgtcgcc acggccatgc    3360
tcggcctcta catcatcctc tgagtcgcgc gccgaccccg cgagagaccg tggtccgtcc    3420
agtcgcagta gagtagagcg ctcgtcgtct cgttccgttt cgtgcctgtc gccgttcgag    3480
gttcgtttct gcgtgcagtc cggtcgaaga agccggtggg ttttgagtac tagtggtagt    3540
agtagcagca gctatcgttt ctgtccgctc gtacgtgttt gcgtggtcgc ggagaacaat    3600
taattgggtg tttgcgagtc ctctggttaa gatgaaccac tgatgctatg tgatcgatcg    3660
atcggtatga tctgaatgga aatggatcaa gttttgcgtt ctgctgatga tgtgatccat    3720
ttggatctgt gtggggcaac agtttcgctt gcttttgctc tgcgatgaac gaatgcttct    3780
tgcatgcatc ttgtctttgc ttaatttgaa ctgtagaacg gatgcagtac tgatttctgc    3840
ttatgatgtg acgattcgtc gtacgcatat catctcttca aatttgtgta gcagctgttt    3900
gtagcttcca ttctgctatg gacgaatgcc tgttttcac ggagaaccgc gcgcggggac    3960
cgatgcggct ttgtgttgcc atgttgtttt ccacgccagg acaaaataga tggtgcggtt    4020
ttgatcccca atcccaccat caccatgttc cggagagcca catggaactc acgtcaagcg    4080
```

| | |
|---|---|
| gtcactttt gcagaatcac tcttaccatt ttacccttt gttgaaacct ctctcctcat | 4140 |
| ccccaaaagt tgatgcaaca gtgctatgcg cgcccaccca tgcttttca tatgattgta | 4200 |
| aaatttggat cgattttatc ttttgaaccc taagtccggt ttacaatctg tttgcatgtt | 4260 |
| tatgttcctt gcggcgagga ccattaaaca agactactat tggatatatt tcgacaggct | 4320 |
| ttgaaatccg aattc | 4335 |

<210> SEQ ID NO 7
<211> LENGTH: 4335
<212> TYPE: DNA
<213> ORGANISM: Artificial Sequence
<220> FEATURE:
<223> OTHER INFORMATION: synthetic DNA of Ms1

<400> SEQUENCE: 7

| | |
|---|---|
| aagcttaaac catttagtta caaatatcga tgcacacctt cggtggggcg ttgtgaaaaa | 60 |
| gcatgttttt tgggtcgaca agccccttt gcaacgtatc ctcttctaat cctattcaga | 120 |
| tcattaacat cataagctgc aattgacatg ctcttctgag gatcaggttc atgcaattaa | 180 |
| acatcataaa ctgcatcttt gatgtcatcc ttttcctata ttttttccag attattggct | 240 |
| tgcttcgttt tcaatatcag gttctatgat tcgacttctg ttgttgccag taataatttg | 300 |
| tagttgctgc ggaatatgaa ctcaaggaga gctgatggtg ctatgaagtt gatttgatgg | 360 |
| gaggttgttc tacacctgca cttgctgctc gacttaaata catgccttgg atttcttccc | 420 |
| agctctagta cataatattt ttcaaattaa tgttccacga cataaaattt aaatccacaa | 480 |
| acatatttt agtacatgaa caattttcta atatagggca aacattttc atatacaaac | 540 |
| cgatcatttt aatatatggt gaaaatcagt gtaatatatg ctgaaatgtt ttcaaataca | 600 |
| tattgaacat atttataata aatggtgaac attttttta ataattgatg accatttta | 660 |
| aaatgcatat tgaacatttt ataatataca ctgtacagtt ttataataat cgacgaacat | 720 |
| cttttggagt tctgaacatt tttttcaaaa acacaagcca ttttccagga agaatacaaa | 780 |
| tgcaaaagaa atgagatatc caaaaagcaa aaagaaaaa caaacaaaa cagagaaacc | 840 |
| tacaggaaaa tccaaacaga aaaggcaaag aaagaacccg aactgggcca ggcaatgttt | 900 |
| ccaacggcct cgctcttcct gaacaagaag gccagtcagc ccatgggctg ctcccagtac | 960 |
| tcgggccccg ctgtggcagc acgccatgta atagttttcg cgggaatcca acgccgaaat | 1020 |
| cgcccgcagc gggaacccga cgtcggtctg gtgcgttctg gcgccttcca gaactctcca | 1080 |
| caggctcccg cagccgtccg atcagatcag cacgaagcac gaacattggc gcgcggcgat | 1140 |
| attttctttc ctcgcccgac gacggccgca ctgcatttca ttttgaattt caaaattcgg | 1200 |
| aaacggaata gctttctcgc atcccgaggc gaggcggtta cgggcgccag aggggccacc | 1260 |
| ccacccaccc accccgccc tcacgtgccc cgcgcggccg aatccgggcc gtccgcgcgg | 1320 |
| acagctggcc gcgcccagcc cgaaccgacg cccaggatcg agcgagggcg gcgcgcccgg | 1380 |
| ggcttggctt agcgtccacg ccacctccgg ctatataagc cgccccacac ccgctccccc | 1440 |
| tccggcattc cattccgcca ccgcaccacc accaccacca aaccctagcg agcgagcgag | 1500 |
| ggagagagag accgccccgc cgcgacgatg gagagatccc gcgggctgct gctggtggcg | 1560 |
| gggctgctgg cggcgctgct gccggcggcg gcggcgcagc cggggcgcc gtgcgagccc | 1620 |
| ggcgctgctgg cgacgcaggt ggcgctcttc tgcgcgcccg acatgccgac ggcccagtgc | 1680 |
| tgcgagcccg tcgtcgccgc cgtcgacctc ggcggcgggg tgcccctgcct ctgccgcgtc | 1740 |
| gccgccgagc cgcagctcgt catggcgggc ctcaacgcca cccacctcct cacgctctac | 1800 |

```
agctcctgcg gcggcctccg ccccggcggc gcccacctcg ccgccgcctg cgaaggtacg      1860
ttgtccgcct cctcccctcc ctccctccct ccctctctct ctacgtgctc gctttcctgc      1920
ttacctagta gtacgtagtt tcccatgcct tcttgactcg ctagaagtgc tccggtttgg      1980
gtctgttaat ttcctcgctg tactaccgga tctgtcgtcg gcacggcgcg cggcgtcggg      2040
tcctcgcctt ctcccgtggc gaccgacctg cgcagcgcgc gcgcggccta gctagcttca      2100
taccgctgta cctcgacata cacggagcga tctatggtct actctgagta tttcctcatc      2160
gtagaacgca tgcgccgctc gcgattgttt cgtcgattct agatccgtgc ttgttcccgc      2220
gagttagtat gcatctgcgt gcatatgccg tacgcacgca gatgcagagt ctgttgctcg      2280
agttatctac tgtcgttcgc tcgaccatat ttgcctgtta atttcctgtt catcgtgcat      2340
gcagtagtag tagccatgtc cacgccttct tgttttgagg cgatcatcgt cgagatccat      2400
ggctttgctt tctgcactat cttctgcctt gttttgttct ccgcagtacg tacgtcttgc      2460
ttggtcaaaa ctgaaaaacg ctttgctgtt tgtttgatcg gcaagagctg gccgtgcttt      2520
tggcaccgca gtgcgtcgcc tctgccgctt ttgcgaaaca tttccatgtt gatcctctgg      2580
cggaactact ttttcgcgtg cggtttgcgt ggccttcctc tctcgtgaaa agaggtcggg      2640
tcaaaccaaa tggatcgcct cttggcagag cagcggcagc agatagctgg ccgtctcgca      2700
gctttggcag aaccggtctg tggccatctg tcgccgcctg ccaccgtttc cctgatgttt      2760
gtttctctct cgcctgccac tgtttctttt cttgttgcgc acgtacgtcg tcacctcctc      2820
ctactttttt gccagttttg tttacttttg atgaaatata cggatgaatc ggctggtgat      2880
taactttggc tgctgctgtt aattactgtg gattttggat gcaggacccg ctcccccggc      2940
cgccgtcgtc agcagccccc cgccccgcc tccaccgtcc gccgcacctc gccgcaagca      3000
gccagcgcgt aagaacctct ccctctccct ctctctctcc ctctcgcctg catctcgcta      3060
tgtttatcca tgtccatatg ttgatcagcc ttgtttagtt actaacatgt gcaccggatc      3120
gggttctcgc agacgacgca ccaccgccgc caccgccgtc gagcgagaag ccgtcgtccc      3180
cgccgccgtc ccaggaccac gacggcgccg ccccccgcgc caaggccgcg cccgcccagg      3240
cggccacctc cacgctcgcg cccgccgccg ccgccaccgc cccgccgccc caggcgccgc      3300
actccgccgc gcccacggcg ccgtccaagg cggccttctt cttcgtcgcc acggccatgc      3360
tcggcctcta catcatcctc tgagtcgcgc gccgaccccg cgagagaccg tggtccgtcc      3420
agtcgcagta gagtagagcg ctcgtcgtct cgttccgttt cgtgcctgtc gccgttcgag      3480
gttcgtttct gcgtgcagtc cggtcgaaga agccggtggg ttttgagtac tagtggtagt      3540
agtagcagca gctatcgttt ctgtccgctc gtacgtgttt gcgtggtcgc ggagaacaat      3600
taattgggtg tttgcgagtc ctctggttaa gatgaaccac tgatgctatg tgatcgatcg      3660
atcggtatga tctgaatgga aatggatcaa gttttgcgtt ctgctgatga tgtgatccat      3720
ttggatctgt gtggggcaac agtttcgctt gcttttgctc tgcgatgaac gaatgcttct      3780
tgcatgcatc ttgtctttgc ttaatttgaa ctgtagaacg gatgcagtac tgatttctgc      3840
ttatgatgtg acgattcgtc gtacgcatat catctcttca aatttgtgta gcagctgttt      3900
gtagcttcca ttctgctatg gacgaatgcc tgttttcac ggagaaccgc gcgcggggac      3960
cgatgcggct ttgtgttgcc atgttgtttt ccacgccagg acaaaataga tggtgcggtt      4020
ttgatcccca atcccaccat caccatgttc cggagagcca catggaactc acgtcaagcg      4080 gtcactttt gcagaatcac tcttaccatt ttacccttt gttgaaacct ctctcctcat       4140
```

```
ccccaaaagt tgatgcaaca gtgctatgcg cgcccaccca tgcttttca tatgattgta      4200 aaatttggat cgattttatc ttttgaaccc taagtccggt ttacaatctg tttgcatgtt      4260
tatgttcctt gcggcgagga ccattaaaca agactactat tggatatatt tcgacaggct     4320
ttgaaatccg aattc                                                      4335

<210> SEQ ID NO 8
<211> LENGTH: 4504
<212> TYPE: DNA
<213> ORGANISM: Oryza sativa

<400> SEQUENCE: 8
gaacagtgca ctggttggga taacaagaag ttagaaattg gcatatata tagaagggta       60 agacacctct aatggatagg gtggacaatc catcaaagat gactattttg gcacctctga     120
ggccgtgaca agttgcctat cttcgcaccc ttcacaagtg actccctact tgtgatgggt     180
cgtgagatgt gagccggtga tctttctcag atgtaaattt cggcctctca caagtgactc     240
cttatctgtg ataggtcttg ccctcacagc ctcatctgta acggcctcta attcaatccg     300
ttacagatta aatcattcat gacaagacac tttgacccat cataggtggg ttgttaatgt     360
tgaaccgagg tagcgtggtg gtggcttctt tgattgttga gcgggttgtg ttcttcatca     420
cttggtagga agtaggaacc caagaaggtt agaagcccac aactattata tcgtcggcct     480
cattggtaaa tgggctagaa gcctagaggc aatctgattc aatagtgtcg gaaatttgtg     540
gatgggccag agacgttgcg tcgtcttcga ctcttcgagt gcctggccta cggatctgca     600
cgaatcttag agcaagtaga aaatcgcata tcgtcgtgta gagcgcagca caaattcgag     660
ttgcttttcc cttttcgca gccaaatctt acctgctcac gtgccgtgct gcccggtgtg     720
cagagcccac gcgccacggc gccagtgtac tacaccgaat cggcaccatc catcgccaca     780
gctggccggt cccccctaag acggacgctc cggatcaatc cacgttggca tggcttcccc     840
gcatcgcctt ctccgcgccc ccgcctatat aatggcgctc tcgcttctct tccccatttc     900
gtcttcccct tctctagagc cttcctctca cagagcacac acaaaaccct agagtaggaa     960
gcgagcgaga gagagagaga gagagagaga gaccacaccc atggagcgct cccacctcgc    1020
cgtcctgctc ggcctcctcg ccttcgccgc cggggtcccg gccgcagcgg cggccaccgc    1080
cgtggaggga gcgcaggcgg ccacggcgga ggcgtcgtgc gagccctcca tcctcgccac    1140
ccaggtctcg ctcttctgcg cgcccgacat gcccaccgcg cagtgctgcg agccggtggt    1200
ggcctccgtc gacctcggcg gcggcgtacc ctgcctctgc cgcgtcgccg ccgagccgca    1260
gctcatcatc tccggcctca cgccaccca cctcctcacg ctgtacgccg cctgcggagg    1320
cctccgccct ggaggcgctc gcctcgccgc gcctgtgaa ggtacgtaca tgcataaccct    1380 cctcctcctc ctcctcctct ctctctctct ctctctctct ctctctctct ctctctctct    1440
ctctctctct ctctctctct ctctctctct ctctctctct ctctctctct ctctctctct    1500
ctctctcggt tggggttgct gccttgcgtt tttggttggt ttttcgtggg ttgggcgaga    1560
tccttcgagt tgcttgtgtt ttgtggtatg ctaggcttcg aacgagttgc cggcgttgct    1620
gtgtcgacca actctcgtat gcttatcttt cagcacatga gttttggcct cgttttact     1680 cggttgttgt atgctacttc tgagatttga gttcatccac tgctaaactg acatcataga    1740
tgaagaatag cagcggcgtt tggtcgattt tgattccttt ctctggatgt tcgagctgat    1800
cttgtggtta ttgctcgaag cctcgaaacg cttgcgcaca tgcaagatcc agcaacgtat    1860
agatctatag tggtgttgtg cttttattcg gatttgtggt tcagtgttta cgtgcgaagt    1920
```

```
cacgcgttcg atgtttccgc ttgagctcca tatctatagc acaaatcaat catgtgcgtt    1980
gcgcgagttc aagctcgaga gaaaagaaaa gcatcaaggc cacggggggt ttttgggcca    2040
ggtcgtgatt ctcccttgaa ctccgaatat accgagttta ttatcttttg agcggatttg    2100
gtgttgaact ggcaggactc aaaacccacc cgtgggacga tcgttttctt ttcctttcgc    2160
tttgtgttct ctgtctcctt tccgtgaaat ctctgcgttt cccttctggt gcttgttata    2220
gatgattctg gatcgagccg tgtatgctcg tgcagtggta cgacttggcg atgaacgtgc    2280
ttgcggagct agtcgcagtt catctttctt ttttttttcc ctcgtttctt ttctcggcgt    2340
ttcattctct acacctcttc tactcgccat gcatgttcat ctctctccgt gttggtcctc    2400
atttggagcc gattcgaacc gggcagcaca gtgctttttt tctgtttcgt tttggaggtt    2460
tccactttcg tgaaaaggaa agggtcaaat cgaatcgccc cctgaaccat cctttgcaga    2520
gcttttttgg acgtttccgc ctttcgtcag agaccatctg cactgcgcgt ttctccccaa    2580
ctcgatcgat tttgcagctt ttaatcactt tttagaaaaa gttttaatc actcgtcatc    2640 gatgtgatct cttgctctaa ttgcatcttc tccgtaggat tagcacttcc atgcttcttg    2700
ttttgtctgt tcaattagcc aagaaacgag tcagtatacc ttcaagatgc atgcagattt    2760
aaaatcggca ctgctcttta tcttgttctt gttttttgcaa gttttggttg gttcaaaact    2820
tatctcttct gcagcattgc ctgctgtgta cagaaagttg gcaggggcat cgtgcagctt    2880
ttttgcctgc tgtgtgtaac gttttctttc cgtacgttgc gttccgtttc acgtcgctta    2940
cctctgtttc ttggggcgca agttatggca gtacagccgt tgtttccacg ttggaaggac    3000
ggttttgccc cttcgcttcc agaagcttcc agagattttt cgagttttc taatgtgttt    3060 gttattgctg taactcgttc taacgtgcag gtcccgcccc accggcctcc atcgtcactg    3120
ccccgccgcc cccggttgct tttcgccgca agccgccggc acgtaaggct gattgattcc    3180
ccttcatcca ctgattgtta atgcgcgtgt aatctttgtg attactaact tgctgctgga    3240
tgctttgcag gcgaggcacc tcccccaccg ccggcggccg agaagctctc cccgccgcct    3300
cagcagcacg acgactccga ccacaacaag cgcgtcggcc cactcccgag aggctctcct    3360
cccccgtatg cccagtccgt cccggtcggc cccgccgccg ctccccgcc accacgctcc    3420 ggcgcctcct cgtcgctcca ggcgcccctc gccgccacca ccaccatcgt tgccatcacc    3480
ctcatcgccg ccgcccagta ctgaggacac gccgccgccg gcgcccgctc cccagagcca    3540
tgattcgttc gcagtatttt tcatcctgtt cttttgcttc tctctctggc tacccatgta    3600
tatgagtttg gaagacgatg atttgatcta gtagcgcgtt accaagtttg cctagattcg    3660
agtagtagct gtggtactat gctgatgtct ctttgatcgc gtcgtctcta gagcgtccgc    3720 cgttttgat cgatcactag catggccgat gtgagtccag catgaaaagt ggtcgaggag    3780
aacattgttg ctaagttttt tttttgcttt ctatctccag tagctgaaca agtatgtcaa    3840
ctgaatgctg caatgaagtg aatggatgca gtcttaaatt tagccttttct gttgccaact    3900 tcttcctctg ttctgtacgg ttcagatgct gcttgttctg tttatgcgat ggtgttgcat    3960
tgttgtgatg tgtgaagtgc gcccaattct gggtgaactc tgcagtattg caagctctg    4020 atcgatacat aaagaactga aatgtgccgg cttctccgcc tcccgttgca tgctcttgtg    4080
cgcgagctgc acagcgcaac cgcgccctcc tctgcacatc catcgacaca aagtctcaag    4140
ttgttgcgcg tgtgctctac caggcaccgt ggctcctgcg ggcgtgcacg ggtcacattc    4200
acatcgcacc caagttgcgg acgtttcagc tgagcaccta ccatccgcaa tgtttgccca    4260
```

| | |
|---|---:|
| cagcttgctc gatgaaatga ctggttcatg tcaaaaggta aaaactgaca ttctcacgcg | 4320 |
| gtaaattccc ctaagcttca tagaccaccg cactgtcatc cactcgacct gccacgacac | 4380 |
| ccgccaccgc agaacgcgac accctgtgcc cacggccacc taccctggca cgcaccgagc | 4440 |
| cgaagccgga taagcacccg agttgatccc catgagacgt ggcgactcgg ctgccctctg | 4500 |
| ccac | 4504 |

<210> SEQ ID NO 9
<211> LENGTH: 687
<212> TYPE: DNA
<213> ORGANISM: Artificial Sequence
<220> FEATURE:
<223> OTHER INFORMATION: cDNA of OsMs1

<400> SEQUENCE: 9

| | |
|---|---:|
| atggagcgct cccacctcgc cgtcctgctc ggcctcctcg ccttcgccgc cggggtcccg | 60 |
| gccgcagcgg cggccaccgc cgtggaggga gcgcaggcgg ccacggcgga ggcgtcgtgc | 120 |
| gagccctcca tcctcgccac ccaggtctcg ctcttctgcg cgcccgacat gcccaccgcg | 180 |
| cagtgctgcg agccggtggt ggcctccgtc gacctcggcg gcggcgtacc ctgcctctgc | 240 |
| cgcgtcgccg ccgagccgca gctcatcatc tccggcctca acgccaccca cctcctcacg | 300 |
| ctgtacgccg cctgcggagg cctccgccct ggaggcgctc gcctcgccgc cgcctgtgaa | 360 |
| ggtcccgccc caccggcctc catcgtcact gccccgccgc ccccggttgc ttttcgccgc | 420 |
| aagccgccgg cacgcgaggc acctccccca ccgccggcgg ccgagaagct ctccccgccg | 480 |
| cctcagcagc acgacgactc cgaccacaac aagcgcgtcg gcccactccc gagaggctct | 540 |
| cctccccgt atgcccagtc cgtcccggtc ggccccgccg ccgctccccc gccaccacgc | 600 |
| tccggcgcct cctcgtcgct ccaggcgccc ctcgccgcca ccaccat cgttgccatc | 660 |
| accctcatcg ccgccgccca gtactga | 687 |

<210> SEQ ID NO 10
<211> LENGTH: 5291
<212> TYPE: DNA
<213> ORGANISM: Brachypodium distachyon

<400> SEQUENCE: 10

| | |
|---|---:|
| cccttaaaag ggggtaatga tggctcatat tgaggaattg acatgcaccc cttaaaggag | 60 |
| gtaatgatgg ctcatattga tttgaggaaa ctccttccat aaggacatct ccaacaagac | 120 |
| acagtcagcg gtactataaa gcacggcacc tggatcagtt ctcgtcgagg gtgcagacga | 180 |
| cgattgcagt gaatatgatg actatcgcgg cgacgaggag ggggggcagt ggggacggct | 240 |
| gaggtgcatc ctctgccaaa ttaaagcacg cgcgcgtgcc acgcgagtca gatcaaggac | 300 |
| acgcaaaaca gataacatat taacaggaag caacgcatag atttttagaa tcgagtaaaa | 360 |
| gaatagcagc agcatttttt ttagcgaaat agtagcagca attagatcaa gcgaaatgta | 420 |
| aaggttgttc ataccaac aagggcggcg gtgtggggcg ggacattgac ctccggggcc | 480 |
| tcctccaggg cctgcggcgc ctgctgggcc tcgacaaatg cagtcaggct gcaagatatg | 540 |
| agggtaaaaa aacagatgta cagtccggtc aagaaaaaca acaaacatgc agactactta | 600 |
| gatctgccaa gactaaatta cctaacgatt ccaagtccag tgatggttgc atcgcgatga | 660 |
| atttcagcca tgctgcgtgc ccgcctggtt accggacgcg cgggaagggg agcaagccca | 720 |
| atcagagcgg gtgcagccgg gcggcgtgtg ttattgcgat aatactcgac ggtatgcttc | 780 |
| caccgcaggt acagtctcag gaaggcatcc gattgaccca ccagatcatc tatcaccaag | 840 |

```
gtagccattc tgccacccat ctaaacacaa actgagagta agaaagcagt ttgaccgcga    900
ttgtttatca caaaaggcaa cacaaaaaaa ctgctagctt cgtgtcagaa aatcaacatg    960
catggtgcgc gacagtacaa cagaaacatg gggagacata gcagaaacgt ccaaaccaaa   1020
aatccaaaaa aagaaggaga tgcactgcgt aagaaaacag cacgggaagc gctcttcacc   1080
gtgtgagact gcacaagtcc aagagacgac aatagcagaa aagaactgca gaaaggagag   1140
ctgctttcgg gggtcaaagt actagcacgg cttcgatcaa tcggtcgatt aaatccctcg   1200
tgccaccgag atcctcacag tgctcgaggg gacactctaa gtcggctttg tcacatccaa   1260
cccaaacaac acgctcttgt ctaaggtgct caacaaaggt gatgtgttcg cacgcaggca   1320
cagtggaaca acaaactagc gtcgatcgac cacgtccctc ccccagaaaa gtgctcccaa   1380
catgatcgca tcgaagtaat cgtagagata gatcttacag aataaaaaat aaacccaaac   1440
caaaggagga gttctgcact actagatccg aaccaaagcc aggaaatagc aaactaaaca   1500
caaaagatat cgatgaaatc atacatcgtc caaacgtttc ggattacacc ttctggtcgc   1560
aactctcgtg ctcaccgcgc agacagatct tctgtacgta ccttggctcc agcccgagga   1620
gagcgagcac tccaggaaac ggcggtctcg agcgagcagt ctaggaaatg gcggtcgcga   1680
tggaaaagcc ttcaagagat atcgggtgat gccccctatt tctagagctc tggcctttac   1740
agttcaccac ttcaccctgc gccatcccga ttcccagtac ctatgacgag cgacgaccct   1800
cacgtgcctg gccagcatca cgggagagaa tcttgctcag catctcaacc gcccaaacag   1860
acagctgtcc ggtcccaccc aaatggacgc acaggatcga tcgggccgcc ggtggcctgt   1920
ccttggctaa cccttcacgc ctcttcgtcc cctccgccta tataatccca ccccgctccg   1980
cttcttcccc caccgcgctc tcttcctctg gactcacacc aactcgccta gcctagcgg    2040
taggaagcga aagcgagaga tcccacccat ggagagatcc caccacctcc tcctcgtgct   2100
cggcctcctc gccgcgctgc tcccggcggc cgcggctacc ttcgggacga cgcagccgga   2160
gcctgggggcc ccatgcgagc ccaccctcct cgccacccag gtctcgctct ctgcgcgcc    2220
ggacatgccg accgcgcagt gctgcgagcc tgtggtggcc tccgtcgacc tcggggggtgg    2280
cgtcccctgc ctctgccgtg tcgccgccga gccgcagctc gtcatggccg gcctcaacgc   2340
cacccacctc ctcacgctct acacctcctg cggtggactc cgccccggag gcgcccacct   2400
cgccgccgcc tgtgaaggta cgcgacgcct gcgtctctct ctctctctgc gtctctctct   2460
gcgtctctcc catgacgagc aactcgcgat acgccttact gccttatttt ttttgaagat   2520
atgtgtctgc ttggtccact gtatttgggt tcttctttcg agaagttcat ccgtaggcat   2580
ctataatccg acgagttcgg atgagatcaa acagtgacac gcgcgacacc aacgttttca   2640
acgatctctt gctgtttggt ttgatatttc ctgcttccca tgatctattt tcaacctttt   2700
ttgtatggct ttcgctccaa tctcgtgcag aaccatattt catcttgggt ttatgctgtt   2760
ctgtaagatc tagcgccatg cagaggtcat ttctgctgtt ccagaccccc tacgtgacat   2820
ttgctgttttt tcctctttgt tgccatggcc acgggttggt ttttacgaaa gatactttga   2880
tatgtcaaga tctgcgagca ctttgaaacc ccaacgcatt ttctatgtgt tttgtgctgt   2940
ttgatcgacc gattgatcga ggccgtgcta gtactttgac acccgaaagc atctctcctt   3000
tctgcagtat cttttctgtt cttgtcgtct cttgggcttg tgcagtttac catggtgaag   3060
agcgcttcat acacgatctg ccgcgaggcc agagcaaaag cttcccgtgc ttttttcttgc   3120
acagtgcatc tccttctttt ttgccttttt cgtttggacg tttctgcttc gtctcccat    3180
```

| | |
|---|---|
| gtttctgttg tactgtcgcg caccatgcat gttgattttc tgatacgaag ctagtactgc | 3240 |
| tctgcagttt ttgtgtagcc ttcctctttc gtgataaaga acgtggtcaa actgctctct | 3300 |
| gactctgttc gtctaaatct ttttctcgca ggaaaatttt cgttgcagat ctcctttacc | 3360 |
| ctcgtcctcc gcatctgttt gctttacctg ctgtagttgc gttcttcgtt tgaatcaaat | 3420 |
| tcttgtttcc ttcttttatc ccatcgctcg tttagttacc ttttcttttt attgaacttt | 3480 |
| agttcattgg tgtagtaggc agtagtatgc tttgcgttgt ttgcggagta gcaattgaat | 3540 |
| tgctctccgg tctctgcaga gcggcccgct gaacagatag ctggctgcag cagctttacc | 3600 |
| agaatcggtc ggttacgaac ttacgattat acccttcgtc ttgctttcat ttactggtag | 3660 |
| cctgctagtc ttttcttgtt gcgcacgtaa tcgtacccag tactgtacgc ttagataaaa | 3720 |
| tagacgggtc tggccttaaa ttatttcgtt gcgttttcga attttgaatt ccggaagtta | 3780 |
| actttatttt gtgctctgtt tggacgcatg tgcaggtcca gctcctcccg ccgccgtcgt | 3840 |
| cagtgcccct cccccctccg ccgcacctcg ccgcaagcag ccagcacgta cgaacaacct | 3900 |
| tttacacttc gcttgatcta attgctgctg ctatactctc ttactcgatt ctaaatctat | 3960 |
| gttttgctca ttattaatat gttgatctga ctcgtgtggc acgcgcgcgt gctttgattt | 4020 |
| cgcagacgag gcacctccgc ctccgccgtc gactgagaag ccgtcccgc cgcctcagca | 4080 |
| ggacaacgtc accgcccacg gcaaggcaat ccccacccat gcggccacat ccccgctcgc | 4140 |
| gccggctgct tccatgatcc acatgtcccc accgccgca tgcaatccat gctccggctc | 4200 |
| cgccgcttcc tcagccgagg ggcccctcct catcgccgcg ctcctcctcg tcatcaccgc | 4260 |
| catcatcgtc ggcaccctcg acgataagtg atccaggagc cgtccgcccc ctccgactca | 4320 |
| ccaacgtccg actatgatcc agttgcagta gtggtcttgt tctgtttcat gtttctcgcc | 4380 |
| atttggttcc gagatttcta tatcgtgcct agtcgtagct gtagcagtca gtatgttcat | 4440 |
| gtgtccacaa gatgtggtcg agtataacat tgggtttcat gattcctcta gcagatgaaa | 4500 |
| cactatgtga tgtgatctga atggatgcag ttttgctacc ttttctgctg ctatgatatg | 4560 |
| cttatccata tgtttatctt tcattccctt aatttgtgcg gtttagcgtt gtgttgccat | 4620 |
| gaatgcctct gctctgcttt gcgggttgc attttgtctt cgttctgctg tatatttgat | 4680 |
| tctgaatttg catgctgtga gtactaagta ctgactacaa tctctggatg gttttgaaat | 4740 |
| ttgaatgatg ttataaagga gagctagctg gggaattgcc tcacctctaa actccaaaac | 4800 |
| acagagcaga agttggcctc aagatccaac ttggtcactt tgcatgtcgg agcattgtag | 4860 |
| caattctgca ataaacggag tagttctgtt agcatgttgt ttttacactg tcagtacaag | 4920 |
| tagaggtcga tgattaatta tattccggtt gtttgctgct ggcttccag ttccctccag | 4980 |
| gtaggaagga accgtatccg ggtagtagcc agtagtagcc aggaagctac tagcagaaca | 5040 |
| gtcttctggt gctctttttt tggagtaacg tcttctcgcg atcttttcg agtaattcaa | 5100 |
| atccgggtat accgagcctt gtatcagtga gagccgatag tcttaattat ctccagcaca | 5160 |
| ggcacaggaa caaccacgtt tgttttcag aatgcacagc aacatttttt ttaagagcat | 5220 |
| ggcacagcta ctttttttt ttttaaggaa acatggcaca gctacatttt tttttagagg | 5280 |
| aacatggcac a | 5291 |

<210> SEQ ID NO 11
<211> LENGTH: 687
<212> TYPE: DNA
<213> ORGANISM: Artificial Sequence
<220> FEATURE:
<223> OTHER INFORMATION: cDNA of BdMs1

<400> SEQUENCE: 11

```
atggagagat cccaccacct cctcctcgtg ctcggcctcc tcgccgcgct gctcccggcg      60
gccgcggcta ccttcgggac gacgcagccg gagcctgggg ccccatgcga gcccaccctc     120
ctcgccaccc aggtctcgct cttctgcgcg ccggacatgc cgaccgcgca gtgctgcgag     180
cctgtggtgg cctccgtcga cctcgggggt ggcgtcccct gcctctgccg tgtcgccgcc     240
gagccgcagc tcgtcatggc cggcctcaac gccacccacc tcctcacgct ctacacctcc     300
tgcggtggac tccgccccgg aggcgcccac ctcgccgccg cctgtgaagg tccagctcct     360
cccgccgccg tcgtcagtgc ccctcccccc tccgccgcac ctcgccgcaa gcagccagca     420
cacgaggcac ctccgcctcc gccgtcgact gagaagccgt ccccgccgcc tcagcaggac     480
aacgtcaccg cccacggcaa ggcaatcccc acccatgcgg ccacatcccc gctcgcgccg     540
gctgcttcca tgatccacat gtccccaccg cccgcatgca atccatgctc cggctccgcc     600
gcttcctcag ccgaggggcc cctcctcatc gccgcgctcc tcctcgtcat caccgccatc     660
atcgtcggca ccctcgacga taagtga                                         687
```

<210> SEQ ID NO 12
<211> LENGTH: 1707
<212> TYPE: DNA
<213> ORGANISM: Artificial Sequence
<220> FEATURE:
<223> OTHER INFORMATION: cDNA of TpMYC4E

<400> SEQUENCE: 12

```
atgcgggaaa tagctactca gcggtgtggt aatcgatcaa tggcgctatc agctcctccc      60
agtcaggaac agccgtcggg gaagcaattc ggctaccagc tcgctgctgc tgtgaggagc     120
atcaactgga cttatggcat attttggtcc atttccgcca gccgcgcccc aggccactcc     180
tcagttctgg cgtggaagga tgggttctac aacggcgaga taaagactag aaagattacc     240
ggctcgacca ctacggagct tacagcgcgac gagcgcgtca tgcacagaag caagcaactg     300
agggagctct acgaatcgct cttgcccggc aactccaaca accgggcaag gcgaccaacc     360
gcctcactgt caccggagga tctcggggac ggcgagtggt attacaccat aagcatgact     420
tacaccttcc accctaatca agggttgcca ggcaaaagct ttgcgagcaa tcaacatgtt     480
tggctgtaca cgctcaata cgcaaacacc agagttttcc cccgcgcgct cttagcaaag     540
acaatcgttt gcattccctt catgggcggt gtgcttgagc tcggaacgtc ggatcaggtg     600
ttggaggacc cgagcatggt gaagcggatc agcacgtctt tctgggagct gcacttgccg     660
tcatccttgg agtcgaagga tccgagctcc agcacatcag caaacgatac cagggaggcc     720
accgacatca tcttgttcga ggatttcgac cacaacgaca cagttgaggg ggtgatctct     780
gagcaaaggg aggtccagtg cccgtccaac gtcaatctgg agcgcctcac aaagcagatg     840
gacgagttcc acagccttct cggtggactg gacgtgcatc ctctcgaaga cagatggatc     900
atggacgagc cctttgagtt tacgtttttcc ccagaagtgg cgccggctat ggatatgccg     960
agcaccgacg atgtcatcgt cactttaagt aggtccgaag gctctcgtcc atcctgcttc    1020
acagcgtgga agggatcatc cgagtcgaaa tacgtggctg gccaggtcgt tggggagtca    1080
cagaagttgc tgaataaagt tgtggctggt ggtgcatggg cgagcaatta tggcggtcgc    1140
accatggtga gagctcaggg aattaacagc aacacccatg tcatgacaga gagaagacgc    1200
cgggagaaac tcaacgagat gttcctggtt ctcaagtcac tggtcccgtc cattcacaag    1260
```

-continued

```
gtagacaaag catccatcct cacagaaacg ataggttatc ttagagaact gaagcaaagg   1320
gtagatcagc tagaatccag ccggtcaccg tctcacccaa agaaacaac aggaccgagc    1380 agaagccatg tcgtcggcgc taggaagaag atagtctcgg ccggatccaa gaggaaggcg   1440
ccagggctgg agagcccgag caatgtcgtg aacgtgacga tgctggacaa ggtggtgctg   1500
ttggaggtgc agtgcccgtg gaaggagctg ctgatgacac aagtgtttga cgccatcaag   1560
agcctctgtc tggacgttgt ctccgtgcag gcatccacat caggtggccg tcttgacctc   1620
aagatacgag ctaatcagca gcttgcggtc ggttctgcta tggtggcacc tggggcaatc   1680
accgaaacac ttcagaaagc tatatag                                       1707
```

<210> SEQ ID NO 13
<211> LENGTH: 568
<212> TYPE: PRT
<213> ORGANISM: Thinopyrum ponticum

<400> SEQUENCE: 13

```
Met Arg Glu Ile Ala Thr Gln Arg Cys Gly Asn Arg Ser Met Ala Leu
1               5                   10                  15

Ser Ala Pro Pro Ser Gln Glu Gln Pro Ser Gly Lys Gln Phe Gly Tyr
            20                  25                  30

Gln Leu Ala Ala Ala Val Arg Ser Ile Asn Trp Thr Tyr Gly Ile Phe
        35                  40                  45

Trp Ser Ile Ser Ala Ser Pro Arg Pro Gly His Ser Ser Val Leu Ala
    50                  55                  60

Trp Lys Asp Gly Phe Tyr Asn Gly Glu Ile Lys Thr Arg Lys Ile Thr
65                  70                  75                  80

Gly Ser Thr Thr Thr Glu Leu Thr Ala Asp Glu Arg Val Met His Arg
                85                  90                  95

Ser Lys Gln Leu Arg Glu Leu Tyr Glu Ser Leu Leu Pro Gly Asn Ser
            100                 105                 110

Asn Asn Arg Ala Arg Arg Pro Thr Ala Ser Leu Ser Pro Glu Asp Leu
        115                 120                 125

Gly Asp Gly Glu Trp Tyr Tyr Thr Ile Ser Met Thr Tyr Thr Phe His
    130                 135                 140

Pro Asn Gln Gly Leu Pro Gly Lys Ser Phe Ala Ser Asn Gln His Val
145                 150                 155                 160

Trp Leu Tyr Asn Ala Gln Tyr Ala Asn Thr Arg Val Phe Pro Arg Ala
                165                 170                 175

Leu Leu Ala Lys Thr Ile Val Cys Ile Pro Phe Met Gly Gly Val Leu
            180                 185                 190

Glu Leu Gly Thr Ser Asp Gln Val Leu Glu Asp Pro Ser Met Val Lys
        195                 200                 205

Arg Ile Ser Thr Ser Phe Trp Glu Leu His Leu Pro Ser Ser Leu Glu
    210                 215                 220

Ser Lys Asp Pro Ser Ser Ser Thr Ser Ala Asn Asp Thr Arg Glu Ala
225                 230                 235                 240

Thr Asp Ile Ile Leu Phe Glu Asp Phe Asp His Asn Asp Thr Val Glu
                245                 250                 255

Gly Val Ile Ser Glu Gln Arg Glu Val Gln Cys Pro Ser Asn Val Asn
            260                 265                 270

Leu Glu Arg Leu Thr Lys Gln Met Asp Glu Phe His Ser Leu Leu Gly
        275                 280                 285

Gly Leu Asp Val His Pro Leu Glu Asp Arg Trp Ile Met Asp Glu Pro
```

Phe Glu Phe Thr Phe Ser Pro Glu Val Ala Pro Ala Met Asp Met Pro
305                 310                 315                 320

Ser Thr Asp Asp Val Ile Val Thr Leu Ser Arg Ser Glu Gly Ser Arg
                325                 330                 335

Pro Ser Cys Phe Thr Ala Trp Lys Gly Ser Ser Glu Ser Lys Tyr Val
            340                 345                 350

Ala Gly Gln Val Val Gly Glu Ser Gln Lys Leu Leu Asn Lys Val Val
        355                 360                 365

Ala Gly Gly Ala Trp Ala Ser Asn Tyr Gly Gly Arg Thr Met Val Arg
    370                 375                 380

Ala Gln Gly Ile Asn Ser Asn Thr His Val Met Thr Glu Arg Arg Arg
385                 390                 395                 400

Arg Glu Lys Leu Asn Glu Met Phe Leu Val Leu Lys Ser Leu Val Pro
                405                 410                 415

Ser Ile His Lys Val Asp Lys Ala Ser Ile Leu Thr Glu Thr Ile Gly
                420                 425                 430

Tyr Leu Arg Glu Leu Lys Gln Arg Val Asp Gln Leu Glu Ser Ser Arg
            435                 440                 445

Ser Pro Ser His Pro Lys Glu Thr Thr Gly Pro Ser Arg Ser His Val
        450                 455                 460

Val Gly Ala Arg Lys Lys Ile Val Ser Ala Gly Ser Lys Arg Lys Ala
465                 470                 475                 480

Pro Gly Leu Glu Ser Pro Ser Asn Val Val Asn Val Thr Met Leu Asp
                485                 490                 495

Lys Val Val Leu Leu Glu Val Gln Cys Pro Trp Lys Glu Leu Leu Met
                500                 505                 510

Thr Gln Val Phe Asp Ala Ile Lys Ser Leu Cys Leu Asp Val Val Ser
            515                 520                 525

Val Gln Ala Ser Thr Ser Gly Gly Arg Leu Asp Leu Lys Ile Arg Ala
        530                 535                 540

Asn Gln Gln Leu Ala Val Gly Ser Ala Met Val Ala Pro Gly Ala Ile
545                 550                 555                 560

Thr Glu Thr Leu Gln Lys Ala Ile
                565

<210> SEQ ID NO 14
<211> LENGTH: 669
<212> TYPE: DNA
<213> ORGANISM: Artificial Sequence
<220> FEATURE:
<223> OTHER INFORMATION: cDNA of Ms1 derived from Triticum boeoticum

<400> SEQUENCE: 14
atggagagat cccgccgcct gctgctggtg gcgggcctgc tcgccgcgct gctcccggcg    60
gcggcggccg ccttcgggcc gcagccgggg gcgccgtgcg agcccacgct gctggcgacg   120
caggtggcgc tcttctgcgc gcccgacatg cccaccgcgc agtgctgcga gcccgtcgtc   180
gccgccgtcg acctcggcgg cggggtcccc tgcctctgcc cgtcgccgc ggagccgcag   240 ctcgtcatgg cgggcctcaa cgccacccac ctcctcacgc tctacagctc ctgcggcggc   300
ctccgtcccg cggcgcccca cctcgccgcc gcctgcgaag acccgctcc cggccgcc    360 gtcgtcagca gccccgcc ccgccaccg tcgaccgcac ctcgccgcaa gcagccagcg    420
cacgacgcac accgccgcc gccgccgtcc agcgacaagc cgtcgtcccc gccgccgtcc    480

-continued

```
caggagcacg acggcgccgc ccccacgcc aaggccgccc ccgcccaggc ggctacctcc    540
ccgctcgcgc ccgctgctgc catcgccccg ccgcccagg cgccacactc cgccgcggcg    600
acctcgtcgt ccaaggcggc cttcttcttc gtcgccacgg ccatgatcgg cctctacctc    660
atcctctga                                                           669
```

<210> SEQ ID NO 15
<211> LENGTH: 222
<212> TYPE: PRT
<213> ORGANISM: Triticum boeoticum

<400> SEQUENCE: 15

```
Met Glu Arg Ser Arg Arg Leu Leu Leu Val Ala Gly Leu Leu Ala Ala
1               5                   10                  15

Leu Leu Pro Ala Ala Ala Ala Phe Gly Pro Gln Pro Gly Ala Pro
            20                  25                  30

Cys Glu Pro Thr Leu Leu Ala Thr Gln Val Ala Leu Phe Cys Ala Pro
            35                  40                  45

Asp Met Pro Thr Ala Gln Cys Cys Glu Pro Val Val Ala Ala Val Asp
        50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Leu Thr Leu Tyr Ser
                85                  90                  95

Ser Cys Gly Gly Leu Arg Pro Gly Gly Ala His Leu Ala Ala Ala Cys
            100                 105                 110

Glu Gly Pro Ala Pro Pro Ala Val Val Ser Pro Pro Pro Pro
            115                 120                 125

Pro Pro Ser Thr Ala Pro Arg Arg Lys Gln Pro Ala His Asp Ala Pro
        130                 135                 140

Pro Pro Pro Pro Ser Ser Asp Lys Pro Ser Ser Pro Pro Ser
145                 150                 155                 160

Gln Glu His Asp Gly Ala Ala Pro His Ala Lys Ala Ala Pro Ala Gln
                165                 170                 175

Ala Ala Thr Ser Pro Leu Ala Pro Ala Ala Ile Ala Pro Pro
            180                 185                 190

Gln Ala Pro His Ser Ala Ala Thr Ser Ser Ser Lys Ala Ala Phe
        195                 200                 205

Phe Phe Val Ala Thr Ala Met Ile Gly Leu Tyr Leu Ile Leu
    210                 215                 220
```

<210> SEQ ID NO 16
<211> LENGTH: 19
<212> TYPE: DNA
<213> ORGANISM: Artificial Sequence
<220> FEATURE:
<223> OTHER INFORMATION: primer 5565329F

<400> SEQUENCE: 16

```
tgcagtgatc ccgatgccg                                                 19
```

<210> SEQ ID NO 17
<211> LENGTH: 17
<212> TYPE: DNA
<213> ORGANISM: Artificial Sequence
<220> FEATURE:
<223> OTHER INFORMATION: primer 5565329R

<400> SEQUENCE: 17

```
ctcggtgcga tgtgtgg                                                     17
```

<210> SEQ ID NO 18
<211> LENGTH: 23
<212> TYPE: DNA
<213> ORGANISM: Artificial Sequence
<220> FEATURE:
<223> OTHER INFORMATION: primer 5570804F

<400> SEQUENCE: 18

```
tgcaggattt tccactgatt aac                                              23
```

<210> SEQ ID NO 19
<211> LENGTH: 18
<212> TYPE: DNA
<213> ORGANISM: Artificial Sequence
<220> FEATURE:
<223> OTHER INFORMATION: primer 5570804R

<400> SEQUENCE: 19

```
cggaggtggt acgcggtg                                                    18
```

<210> SEQ ID NO 20
<211> LENGTH: 26
<212> TYPE: DNA
<213> ORGANISM: Artificial Sequence
<220> FEATURE:
<223> OTHER INFORMATION: primer 5564956F

<400> SEQUENCE: 20

```
tgcagaacta ccagaatctt tatcgg                                           26
```

<210> SEQ ID NO 21
<211> LENGTH: 24
<212> TYPE: DNA
<213> ORGANISM: Artificial Sequence
<220> FEATURE:
<223> OTHER INFORMATION: primer 5564956R

<400> SEQUENCE: 21

```
ctgtgaaacc aagcacccat aatc                                             24
```

<210> SEQ ID NO 22
<211> LENGTH: 23
<212> TYPE: DNA
<213> ORGANISM: Artificial Sequence
<220> FEATURE:
<223> OTHER INFORMATION: primer 5008421F

<400> SEQUENCE: 22

```
tgcagagcaa gagcaacatt caa                                              23
```

<210> SEQ ID NO 23
<211> LENGTH: 23
<212> TYPE: DNA
<213> ORGANISM: Artificial Sequence
<220> FEATURE:
<223> OTHER INFORMATION: primer 5008421R

<400> SEQUENCE: 23

```
cggtcaatgt ataaccacg tgc                                               23
```

<210> SEQ ID NO 24
<211> LENGTH: 19
<212> TYPE: DNA

```
<213> ORGANISM: Artificial Sequence
<220> FEATURE:
<223> OTHER INFORMATION: primer 3573220F

<400> SEQUENCE: 24
tgcagtcagt caacgatgg                                                      19

<210> SEQ ID NO 25
<211> LENGTH: 17
<212> TYPE: DNA
<213> ORGANISM: Artificial Sequence
<220> FEATURE:
<223> OTHER INFORMATION: primer 3573220R

<400> SEQUENCE: 25
gtctcacgtg cagcgca                                                        17

<210> SEQ ID NO 26
<211> LENGTH: 22
<212> TYPE: DNA
<213> ORGANISM: Artificial Sequence
<220> FEATURE:
<223> OTHER INFORMATION: primer 5565375F

<400> SEQUENCE: 26
tgcagtttct atcatgtcca cg                                                  22

<210> SEQ ID NO 27
<211> LENGTH: 21
<212> TYPE: DNA
<213> ORGANISM: Artificial Sequence
<220> FEATURE:
<223> OTHER INFORMATION: primer 5565375R

<400> SEQUENCE: 27
atctcgggtt tatcttcagg g                                                   21

<210> SEQ ID NO 28
<211> LENGTH: 21
<212> TYPE: DNA
<213> ORGANISM: Artificial Sequence
<220> FEATURE:
<223> OTHER INFORMATION: primer 1861695F

<400> SEQUENCE: 28
tgcaggtgtg ctacttaggg c                                                   21

<210> SEQ ID NO 29
<211> LENGTH: 19
<212> TYPE: DNA
<213> ORGANISM: Artificial Sequence
<220> FEATURE:
<223> OTHER INFORMATION: primer 1861695R

<400> SEQUENCE: 29
cggaccttgc cctgaggag                                                      19

<210> SEQ ID NO 30
<211> LENGTH: 18
<212> TYPE: DNA
<213> ORGANISM: Artificial Sequence
<220> FEATURE:
<223> OTHER INFORMATION: primer 5571044F

<400> SEQUENCE: 30
tgcagtggaa agtgcggc                                                       18
```

```
<210> SEQ ID NO 31
<211> LENGTH: 26
<212> TYPE: DNA
<213> ORGANISM: Artificial Sequence
<220> FEATURE:
<223> OTHER INFORMATION: primer 5571044R

<400> SEQUENCE: 31
cggtagatag aagatgagac tttacc                                      26

<210> SEQ ID NO 32
<211> LENGTH: 23
<212> TYPE: DNA
<213> ORGANISM: Artificial Sequence
<220> FEATURE:
<223> OTHER INFORMATION: primer 5565269F

<400> SEQUENCE: 32
tgcaggtgga cctcatggac tac                                         23

<210> SEQ ID NO 33
<211> LENGTH: 20
<212> TYPE: DNA
<213> ORGANISM: Artificial Sequence
<220> FEATURE:
<223> OTHER INFORMATION: primer 5565269R

<400> SEQUENCE: 33
ctcaggcaca ccgcgcagtc                                             20

<210> SEQ ID NO 34
<211> LENGTH: 20
<212> TYPE: DNA
<213> ORGANISM: Artificial Sequence
<220> FEATURE:
<223> OTHER INFORMATION: primer 5570850F

<400> SEQUENCE: 34
tgcaggcggt cctggacagg                                             20

<210> SEQ ID NO 35
<211> LENGTH: 18
<212> TYPE: DNA
<213> ORGANISM: Artificial Sequence
<220> FEATURE:
<223> OTHER INFORMATION: primer 5570850R

<400> SEQUENCE: 35
cggccgccct caccacac                                               18

<210> SEQ ID NO 36
<211> LENGTH: 21
<212> TYPE: DNA
<213> ORGANISM: Artificial Sequence
<220> FEATURE:
<223> OTHER INFORMATION: primer 5565089F

<400> SEQUENCE: 36
tgcagcattg gcaaataaca c                                           21

<210> SEQ ID NO 37
<211> LENGTH: 22
<212> TYPE: DNA
<213> ORGANISM: Artificial Sequence
<220> FEATURE:
```

```
<223> OTHER INFORMATION: primer 5565089R

<400> SEQUENCE: 37
ggttgcattc tctgtgtatc ac                                              22

<210> SEQ ID NO 38
<211> LENGTH: 17
<212> TYPE: DNA
<213> ORGANISM: Artificial Sequence
<220> FEATURE:
<223> OTHER INFORMATION: primer RfF1

<400> SEQUENCE: 38
gccgccgcct gcgaagg                                                    17

<210> SEQ ID NO 39
<211> LENGTH: 17
<212> TYPE: DNA
<213> ORGANISM: Artificial Sequence
<220> FEATURE:
<223> OTHER INFORMATION: primer RfR1

<400> SEQUENCE: 39
gggggagcgg gtcctgc                                                    17

<210> SEQ ID NO 40
<211> LENGTH: 18
<212> TYPE: DNA
<213> ORGANISM: Artificial Sequence
<220> FEATURE:
<223> OTHER INFORMATION: primer ThMYC4ESpF

<400> SEQUENCE: 40
ctcccagtca ggaacagc                                                   18

<210> SEQ ID NO 41
<211> LENGTH: 18
<212> TYPE: DNA
<213> ORGANISM: Artificial Sequence
<220> FEATURE:
<223> OTHER INFORMATION: primer TaMYC4SpR

<400> SEQUENCE: 41
ggtgacagtg aggcggtt                                                   18

<210> SEQ ID NO 42
<211> LENGTH: 228
<212> TYPE: PRT
<213> ORGANISM: Oryza sativa

<400> SEQUENCE: 42
```

Met Glu Arg Ser His Leu Ala Val Leu Leu Gly Leu Leu Ala Phe Ala
1               5                   10                  15

Ala Gly Val Pro Ala Ala Ala Ala Thr Ala Val Glu Gly Ala Gln
            20                  25                  30

Ala Ala Thr Ala Glu Ala Ser Cys Glu Pro Ser Ile Leu Ala Thr Gln
        35                  40                  45

Val Ser Leu Phe Cys Ala Pro Asp Met Pro Thr Ala Gln Cys Cys Glu
    50                  55                  60

Pro Val Val Ala Ser Val Asp Leu Gly Gly Gly Val Pro Cys Leu Cys
65                  70                  75                  80

Arg Val Ala Ala Glu Pro Gln Leu Ile Ile Ser Gly Leu Asn Ala Thr
                85                  90                  95

```
His Leu Leu Thr Leu Tyr Ala Ala Cys Gly Gly Leu Arg Pro Gly Gly
                100                 105                 110

Ala Arg Leu Ala Ala Ala Cys Glu Gly Pro Ala Pro Pro Ala Ser Ile
            115                 120                 125

Val Thr Ala Pro Pro Pro Val Ala Phe Arg Arg Lys Pro Pro Ala
        130                 135                 140

Arg Glu Ala Pro Pro Pro Pro Ala Ala Glu Lys Leu Ser Pro Pro
145                 150                 155                 160

Pro Gln Gln His Asp Asp Ser Asp His Asn Lys Arg Val Gly Pro Leu
                165                 170                 175

Pro Arg Gly Ser Pro Pro Tyr Ala Gln Ser Val Pro Val Gly Pro
            180                 185                 190

Ala Ala Ala Pro Pro Pro Arg Ser Gly Ala Ser Ser Ser Leu Gln
            195                 200                 205

Ala Pro Leu Ala Ala Thr Thr Thr Ile Val Ala Ile Thr Leu Ile Ala
        210                 215                 220

Ala Ala Gln Tyr
225

<210> SEQ ID NO 43
<211> LENGTH: 228
<212> TYPE: PRT
<213> ORGANISM: Brachypodium distachyon

<400> SEQUENCE: 43

Met Glu Arg Ser His His Leu Leu Val Leu Gly Leu Leu Ala Ala
1               5                   10                  15

Leu Leu Pro Ala Ala Ala Ala Thr Phe Gly Thr Thr Gln Pro Glu Pro
                20                  25                  30

Gly Ala Pro Cys Glu Pro Thr Leu Leu Ala Thr Gln Val Ser Leu Phe
            35                  40                  45

Cys Ala Pro Asp Met Pro Thr Ala Gln Cys Cys Glu Pro Val Val Ala
        50                  55                  60

Ser Val Asp Leu Gly Gly Gly Val Pro Cys Leu Cys Arg Val Ala Ala
65                  70                  75                  80

Glu Pro Gln Leu Val Met Ala Gly Leu Asn Ala Thr His Leu Leu Thr
                85                  90                  95

Leu Tyr Thr Ser Cys Gly Gly Leu Arg Pro Gly Gly Ala His Leu Ala
                100                 105                 110

Ala Ala Cys Glu Gly Pro Ala Pro Pro Ala Ala Val Val Ser Ala Pro
            115                 120                 125

Pro Pro Ser Ala Ala Pro Arg Arg Lys Gln Pro Ala His Glu Ala Pro
        130                 135                 140

Pro Pro Pro Ser Thr Glu Lys Pro Ser Pro Pro Gln Gln Asp
145                 150                 155                 160

Asn Val Thr Ala His Gly Lys Ala Ile Pro Thr His Ala Ala Thr Ser
                165                 170                 175

Pro Leu Ala Pro Ala Ala Ser Met Ile His Met Ser Pro Pro Ala
            180                 185                 190

Cys Asn Pro Cys Ser Gly Ser Ala Ala Ser Ser Ala Glu Gly Pro Leu
            195                 200                 205

Leu Ile Ala Ala Leu Leu Val Ile Thr Ala Ile Ile Val Gly Thr
        210                 215                 220

Leu Asp Asp Lys
225
```

<210> SEQ ID NO 44
<211> LENGTH: 1722
<212> TYPE: DNA
<213> ORGANISM: Artificial Sequence
<220> FEATURE:
<223> OTHER INFORMATION: cDNA

<400> SEQUENCE: 44

| | | | | | |
|---|---|---|---|---|---|
| atgcgggaaa | tagctactca | gcggtgtggt | aatcgatcaa | tggcgctatc | agctcctccc | 60 |
| agtcaggaac | agccgtcggg | gaagcaattc | ggctaccagc | tcgctgctgc | tgtgaggagc | 120 |
| atcaactgga | cttatggcat | attttggtcc | atttccgcca | gcccgcgccc | aggccactcc | 180 |
| tcagttctgg | cgtggaagga | tgggttctac | aacggcgaga | taaagactag | aaagattacc | 240 |
| ggctcgacca | ctacggagct | tacagcggac | gagcgcgtca | tgcacagaag | caagcaactg | 300 |
| agggagctct | acgaatcgct | cttgcccggc | aactccaaca | ccgggcaag | gcgaccaacc | 360 |
| gcctcactgt | caccggagga | tctcggggac | ggcgagtggt | attacaccat | aagcatgact | 420 |
| tacaccttcc | accctaatca | agggttgcca | ggcaaaagct | tgcgagcaa | tcaacatgtt | 480 |
| tggctgtaca | acgctcaata | cgcaaacacc | agagttttcc | cccgcgcgct | cttagcaaag | 540 |
| actgcttcta | ttcagacaat | cgtttgcatt | cccttcatgg | gcggtgtgct | tgagctcgga | 600 |
| acgtcggatc | aggtgttgga | ggacccgagc | atggtgaagc | ggatcaacac | gtctttctgg | 660 |
| gagctgcact | tgccgtcatc | cttggagtcg | aaggatccga | gctccagcac | atcagcaaac | 720 |
| gataccaggg | aggccaccga | catcatcttg | ttcgaggatt | tcgaccacaa | cgacacagtt | 780 |
| gaggggtga | tctctgagca | agggaggtc | cagtgcacgt | ccaacgtcaa | tctggagcgc | 840 |
| ctcacaaagc | agatggacga | gttccacagc | cttctcggtg | gactggacgt | gcatcctctc | 900 |
| aaagacagat | ggatcatgga | cgagccctt | gagtttacgt | tttccccaga | agtggcgccg | 960 |
| gctatggata | tgccgagcac | cgacgatgtc | atcgtcactt | taagtaggtc | cgaaggctct | 1020 |
| cgtccatcct | gcttcacagc | gtggaaggga | tcatccgagt | cgaaatacgt | ggctggccag | 1080 |
| gtcgttgggg | agtcacagaa | gttgctgaat | aaagttgtgg | ctggtggtgc | atgggcgagc | 1140 |
| aattatggcg | gtcgcaccat | ggtgagagct | cagggaatta | acagcaacac | ccatgtcatg | 1200 |
| acagagagaa | gacgccggga | gaaactcaac | gagatgttcc | tggttctcaa | gtcactggtc | 1260 |
| ccgtccattc | acaaggtaga | caaagcatcc | atcctcacag | aaacgatagg | ttatcttaga | 1320 |
| gaactgaagc | aaagggtaga | tcagctagaa | tccagccggt | caccgtctca | cccaaaagaa | 1380 |
| acaacaggac | cgagcagaag | ccatgtcgtc | ggcgctagga | agaagatagt | ctcggccgga | 1440 |
| tccaagagga | aggcgccagg | gctggagagc | ccgagcaatg | tcgtgaacgt | gacgatgctg | 1500 |
| gacaaggtgg | tgctgttgga | ggtgcagtgc | ccgtggaagg | agctgctgat | gacacaagtg | 1560 |
| tttgacgcca | tcaagagcct | ctgtctggac | gttgtctccg | tgcaggcatc | cacatcaggt | 1620 |
| ggccgtcttg | acctcaagat | acgagctaat | cagcagcttg | cggtcggttc | tgctatggtg | 1680 |
| gcacctgggg | caatcaccga | aacacttcag | aaagctatat | ag | | 1722 |

<210> SEQ ID NO 45
<211> LENGTH: 573
<212> TYPE: PRT
<213> ORGANISM: Thinopyrum ponticum

<400> SEQUENCE: 45

Met Arg Glu Ile Ala Thr Gln Arg Cys Gly Asn Arg Ser Met Ala Leu

```
1               5                   10                  15
Ser Ala Pro Pro Ser Gln Glu Gln Pro Ser Gly Lys Gln Phe Gly Tyr
                20                  25                  30
Gln Leu Ala Ala Val Arg Ser Ile Asn Trp Thr Tyr Gly Ile Phe
                35                  40                  45
Trp Ser Ile Ser Ala Ser Pro Arg Pro Gly His Ser Ser Val Leu Ala
50                      55                  60
Trp Lys Asp Gly Phe Tyr Asn Gly Glu Ile Lys Thr Arg Lys Ile Thr
65                      70                  75                  80
Gly Ser Thr Thr Thr Glu Leu Thr Ala Asp Glu Arg Val Met His Arg
                    85                  90                  95
Ser Lys Gln Leu Arg Glu Leu Tyr Glu Ser Leu Leu Pro Gly Asn Ser
            100                 105                 110
Asn Asn Arg Ala Arg Arg Pro Thr Ala Ser Leu Ser Pro Glu Asp Leu
            115                 120                 125
Gly Asp Gly Glu Trp Tyr Tyr Thr Ile Ser Met Thr Tyr Thr Phe His
        130                 135                 140
Pro Asn Gln Gly Leu Pro Gly Lys Ser Phe Ala Ser Asn Gln His Val
145                 150                 155                 160
Trp Leu Tyr Asn Ala Gln Tyr Ala Asn Thr Arg Val Phe Pro Arg Ala
                165                 170                 175
Leu Leu Ala Lys Thr Ala Ser Ile Gln Thr Ile Val Cys Ile Pro Phe
                180                 185                 190
Met Gly Gly Val Leu Glu Leu Gly Thr Ser Asp Gln Val Leu Glu Asp
            195                 200                 205
Pro Ser Met Val Lys Arg Ile Asn Thr Ser Phe Trp Glu Leu His Leu
210                 215                 220
Pro Ser Ser Leu Glu Ser Lys Asp Pro Ser Ser Ser Thr Ser Ala Asn
225                 230                 235                 240
Asp Thr Arg Glu Ala Thr Asp Ile Ile Leu Phe Glu Asp Phe Asp His
                245                 250                 255
Asn Asp Thr Val Glu Gly Val Ile Ser Glu Gln Arg Glu Val Gln Cys
            260                 265                 270
Thr Ser Asn Val Asn Leu Glu Arg Leu Thr Lys Gln Met Asp Glu Phe
        275                 280                 285
His Ser Leu Leu Gly Gly Leu Asp Val His Pro Leu Lys Asp Arg Trp
        290                 295                 300
Ile Met Asp Glu Pro Phe Glu Phe Thr Phe Ser Pro Glu Val Ala Pro
305                 310                 315                 320
Ala Met Asp Met Pro Ser Thr Asp Asp Val Ile Val Thr Leu Ser Arg
                325                 330                 335
Ser Glu Gly Ser Arg Pro Ser Cys Phe Thr Ala Trp Lys Gly Ser Ser
            340                 345                 350
Glu Ser Lys Tyr Val Ala Gly Gln Val Val Gly Glu Ser Gln Lys Leu
        355                 360                 365
Leu Asn Lys Val Val Ala Gly Ala Trp Ala Ser Asn Tyr Gly Gly
        370                 375                 380
Arg Thr Met Val Arg Ala Gln Gly Ile Asn Ser Asn Thr His Val Met
385                 390                 395                 400
Thr Glu Arg Arg Arg Arg Glu Lys Leu Asn Glu Met Phe Leu Val Leu
                405                 410                 415
Lys Ser Leu Val Pro Ser Ile His Lys Val Asp Lys Ala Ser Ile Leu
                420                 425                 430
```

```
Thr Glu Thr Ile Gly Tyr Leu Arg Glu Leu Lys Gln Arg Val Asp Gln
    435                 440                 445

Leu Glu Ser Ser Arg Ser Pro Ser His Pro Lys Glu Thr Thr Gly Pro
    450                 455                 460

Ser Arg Ser His Val Val Gly Ala Arg Lys Lys Ile Val Ser Ala Gly
465                 470                 475                 480

Ser Lys Arg Lys Ala Pro Gly Leu Glu Ser Pro Ser Asn Val Val Asn
                485                 490                 495

Val Thr Met Leu Asp Lys Val Val Leu Leu Glu Val Gln Cys Pro Trp
            500                 505                 510

Lys Glu Leu Leu Met Thr Gln Val Phe Asp Ala Ile Lys Ser Leu Cys
    515                 520                 525

Leu Asp Val Val Ser Val Gln Ala Ser Thr Ser Gly Gly Arg Leu Asp
    530                 535                 540

Leu Lys Ile Arg Ala Asn Gln Gln Leu Ala Val Gly Ser Ala Met Val
545                 550                 555                 560

Ala Pro Gly Ala Ile Thr Glu Thr Leu Gln Lys Ala Ile
                565                 570
```